(12) United States Patent
Schieke

(10) Patent No.: US 11,232,853 B2
(45) Date of Patent: Jan. 25, 2022

(54) SYSTEM AND METHOD FOR CREATING, QUERYING, AND DISPLAYING A MIBA MASTER FILE

(71) Applicant: Cubisme, Inc., Milwaukee, WI (US)

(72) Inventor: Moira F. Schieke, Milwaukee, WI (US)

(73) Assignee: CUBISME, INC., Milwaukee, WI (US)

( * ) Notice: Subject to any disclaimer, the term of this patent is extended or adjusted under 35 U.S.C. 154(b) by 713 days.

(21) Appl. No.: 15/959,142

(22) Filed: Apr. 20, 2018

(65) Prior Publication Data

US 2019/0102516 A1 Apr. 4, 2019

Related U.S. Application Data

(60) Provisional application No. 62/488,581, filed on Apr. 21, 2017, provisional application No. 62/580,543, filed on Nov. 2, 2017.

(51) Int. Cl.
*G16B 40/00* (2019.01)
*G16H 30/40* (2018.01)
(Continued)

(52) U.S. Cl.
CPC ............ *G16B 40/00* (2019.02); *G06T 7/0012* (2013.01); *G06T 7/11* (2017.01); *G06T 7/143* (2017.01);
(Continued)

(58) Field of Classification Search
CPC ........... G16B 40/00; G16B 25/00; G06T 7/11; G06T 7/0012; G06T 2207/10088;
(Continued)

(56) References Cited

U.S. PATENT DOCUMENTS 6,567,684 B1 5/2003 Chenevert et al.
6,956,373 B1 10/2005 Brown et al.
(Continued)

FOREIGN PATENT DOCUMENTS

EP  3 043 318      7/2016
EP  3 117 771 A2   1/2017
(Continued)

OTHER PUBLICATIONS

Extended European Search Report in EP 17821418.5 dated Jul. 17, 2020 (10 pages).
(Continued)

*Primary Examiner* — Vu Le
*Assistant Examiner* — Julius Chai
(74) *Attorney, Agent, or Firm* — Foley & Lardner LLP

(57) ABSTRACT

A system and method for creating and using a medical imaging bioinformatics annotated ("MIBA") master file is disclosed. Creating the MIBA master file includes receiving image data, performing a first registration on the image data for obtaining in-slice registered data, and performing a second registration for registering the in-slice registered data to a three-dimensional (3D) model for obtaining source data. Creating also includes extracting voxel data from the source data and storing the voxel data in a MIBA database, receiving selection of a volume of interest, and extracting a portion of the voxel data corresponding to the volume of interest. The MIBA master file is created from the portion of the voxel data, which is stored in the MIBA database. The MIBA system receives a query, extracts data from the MIBA master file in response to the query, and presents the extracted data on an output interface.

18 Claims, 49 Drawing Sheets

(51) Int. Cl.
*G16H 50/70* (2018.01)
*G06T 7/143* (2017.01)
*G06T 7/11* (2017.01)
*G16B 5/00* (2019.01)
*G06T 7/00* (2017.01)
*G16B 25/00* (2019.01)

(52) U.S. Cl.
CPC .............. *G16B 5/00* (2019.02); *G16H 30/40* (2018.01); *G16H 50/70* (2018.01); *G06T 2207/10088* (2013.01); *G06T 2207/30004* (2013.01); *G16B 25/00* (2019.02)

(58) Field of Classification Search
CPC .......... G06T 2207/30004; G16H 50/70; G16H 30/40; G16B 5/00
See application file for complete search history.

(56) References Cited

U.S. PATENT DOCUMENTS

| | | | |
|---|---|---|---|
| 8,509,570 B2 | 8/2013 | Degani et al. | |
| 8,605,980 B2 | 12/2013 | Li et al. | |
| 8,768,431 B2 | 7/2014 | Ross et al. | |
| 8,781,214 B2 | 7/2014 | Davis et al. | |
| 8,805,619 B2 | 8/2014 | Sorensen et al. | |
| 8,818,484 B2 | 8/2014 | Liew et al. | |
| 8,873,836 B1 | 10/2014 | Dietrich et al. | |
| 9,092,691 B1 | 7/2015 | Beaumont et al. | |
| 9,165,362 B2 | 10/2015 | Siewerdsen et al. | |
| 9,424,639 B2 | 8/2016 | Jacob | |
| 9,615,028 B2 | 4/2017 | Mizutani et al. | |
| 10,452,813 B2* | 10/2019 | Sorenson | G16H 10/60 |
| 10,762,627 B2* | 9/2020 | Strommer | G06T 7/0012 |
| 2002/0186818 A1 | 12/2002 | Arnaud et al. | |
| 2002/0193677 A1 | 12/2002 | Thornton | |
| 2003/0072479 A1 | 4/2003 | Sofia Totterman et al. | |
| 2006/0262970 A1* | 11/2006 | Boese | G06T 7/38 382/131 |
| 2006/0269476 A1 | 11/2006 | Kuo | |
| 2008/0097186 A1 | 4/2008 | Biglieri et al. | |
| 2009/0161928 A1 | 6/2009 | Khamene et al. | |
| 2009/0208075 A1 | 8/2009 | Fischer et al. | |
| 2010/0158332 A1 | 6/2010 | Rico et al. | |
| 2010/0284927 A1 | 11/2010 | Lu et al. | |
| 2011/0243417 A1 | 10/2011 | Madabhushi et al. | |
| 2011/0312520 A1 | 12/2011 | Kennedy et al. | |
| 2013/0004044 A1 | 1/2013 | Ross et al. | |
| 2013/0197349 A1 | 8/2013 | Blumhagen et al. | |
| 2013/0329973 A1 | 12/2013 | Cao et al. | |
| 2014/0003697 A1 | 1/2014 | Qian et al. | |
| 2014/0010429 A1 | 1/2014 | Highnam et al. | |
| 2014/0010430 A1 | 1/2014 | Chandelier et al. | |
| 2014/0037172 A1 | 2/2014 | Madabhushi et al. | |
| 2014/0064580 A1 | 3/2014 | Madabhushi et al. | |
| 2014/0079302 A1 | 3/2014 | Sato et al. | |
| 2014/0086836 A1 | 3/2014 | Burnham et al. | |
| 2014/0101080 A1 | 4/2014 | Lee et al. | |
| 2014/0126794 A1 | 5/2014 | Ahn et al. | |
| 2014/0153795 A1 | 6/2014 | Lenox | |
| 2014/0185888 A1 | 7/2014 | Kelm et al. | |
| 2014/0185900 A1 | 7/2014 | Lee et al. | |
| 2014/0195472 A1 | 7/2014 | Kawagishi | |
| 2014/0205163 A1 | 7/2014 | Stark et al. | |
| 2014/0219535 A1 | 8/2014 | Chen et al. | |
| 2014/0228667 A1 | 8/2014 | Dankerl et al. | |
| 2014/0233826 A1 | 8/2014 | Agaian et al. | |
| 2014/0241606 A1 | 8/2014 | Park et al. | |
| 2014/0309511 A1 | 10/2014 | Stal | |
| 2015/0003706 A1 | 1/2015 | Eftestol et al. | |
| 2015/0093007 A1 | 4/2015 | Beaumont et al. | |
| 2015/0198688 A1 | 7/2015 | Cetingul | |
| 2015/0352363 A1 | 12/2015 | Mcintyre et al. | |
| 2016/0019693 A1* | 1/2016 | Silbersweig | G16H 50/20 382/128 |
| 2016/0038095 A1* | 2/2016 | Schieke | A61B 5/7485 600/410 |
| 2016/0086326 A1 | 3/2016 | Raschke et al. | |
| 2016/0117816 A1 | 4/2016 | Taylor | |
| 2016/0203263 A1* | 7/2016 | Maier | G06T 7/0016 705/2 |
| 2016/0217576 A1 | 7/2016 | Kabus et al. | |
| 2016/0292194 A1 | 10/2016 | Farkash | |
| 2016/0350933 A1 | 12/2016 | Schieke | |
| 2016/0350946 A1* | 12/2016 | Schieke | G16H 30/40 |
| 2017/0046839 A1 | 2/2017 | Paik et al. | |
| 2017/0261584 A1 | 9/2017 | James et al. | |
| 2017/0263023 A1* | 9/2017 | Zhou | G06T 19/00 |
| 2017/0358079 A1* | 12/2017 | Gillies | A61B 6/032 |
| 2018/0114312 A1 | 4/2018 | Palma | |
| 2018/0165867 A1* | 6/2018 | Kuhn | G06T 7/0012 |
| 2020/0281539 A1 | 9/2020 | Hoernig et al. | |

FOREIGN PATENT DOCUMENTS

| | | | |
|---|---|---|---|
| WO | WO-2015/175746 A1 | 11/2015 | |
| WO | WO-2016/206942 A1 | 12/2016 | |
| WO | WO-2017151757 A1 * | 9/2017 | ........... G06N 3/0454 |

OTHER PUBLICATIONS

Final Office Action on U.S. Appl. No. 14/821,700 dated Mar. 18, 2019.
International Search Report and Written Opinion in PCT/US2018/028679 dated Jan. 29, 2019 (14 pages).
Notice of Allowance on U.S. Appl. No. 15/925,082 dated Feb. 27, 2019.
"Determining Single Voxel Value from Larger Region of Interest (ROI)," Dec. 18, 2014, 21 pages.
Antipolis, "MEDIAN Technologies strengthens IP portfolio with US patent," MEDIAN Technologies (ALMDT), Sep. 10, 2015, 4 pages.
Ashraf, et al., "Identification of Intrinsic Imaging Phenotypes for Breast Cancer Tumors: Preliminary Associations with Gene Expression Profiles," Radiology, Aug. 2014, pp. 374-384, vol. 272, No. 2.
Baselga, et al., "Everolimus in Postmenopausal Hormone-Receptor 2013 Positive Advanced Breast Cancer," New England Journal of Medicine, Feb. 9, 2012, pp. 520-529, vol. 366, No. 6.
Boes, et al., "Image Registration for Quantitative Parametric Response Mapping of Cancer Treatment Response," Translational Oncology, Feb. 2014, pp. 101-110, vol. 7, No. 1.
Buckley,"Uncertainty in the Analysis of Tracer Kinetics Using Dynamic Contrast-Enhanced T1-Weighted MRI," Magnetic Resonance in Medicine, Feb. 20, 2002, pp. 601-606, vol. 47.
Chan, et al., "Detection of Prostate Cancer by Integration of Line-Scan Diffusion, T2-Mapping and T2-Weighted Magnetic Resonance Imagine; a Multichannel Statistical Classifier," Medical Physics, Sep. 2003, pp. 2390-2398, vol. 30, No. 9.
Colen, et al., "NCI Workshop Report: Clinical and Computational Requirements for Correlating Imaging Phenotypes with Genomics Signatures," Translational Oncology, Oct. 2014, pp. 565-569, vol. 7, No. 5.
Ellingson, et al., "Volumetric Analysis of Functional Diffusion Maps is a Predictive Imaging Biomarker for Cytotoxic and Anti-Angiogenic Treatments in Malignant Gliomas," Journal of Neuro-Oncology, Mar. 2011, pp. 95-103, vol. 102, Issue 1.
Ellingson, et al.."Graded Functional Diffusion Map 2013 Defined Characteristics of Apparent Diffusion Coefficients Predict Overall Survival in Recurrent Glioblastoma Treated with Bevacizumab," Neuro-Oncology, Oct. 2011, pp. 1151-1161, vol. 13, No. 10.
Galavis, et al.,"Variability of Textural Features in FDG PET Images Due to Different Acquisition Modes and Reconstruction Parameters," Acta Oncologica, Sep. 2010, pp. 1012-1016, vol. 49, Issue 7.
Galban, et al., "The Parametric Response Map: An Imaging Biomarker for Early Cancer Treatment Outcome," Nature Medicine, 2009, pp. 572-576, vol. 15, No. 5.
Galbraith, et al., Reproducibility of Dynamic Contrast-Enhanced MRI in Human Muscle and Tumours: Comparison of Quantitative and Semi-Quantitative Analysis, NMR in Biomedicine, Apr. 2002, pp. 132-142, vol. 15, Issue 2.

(56) References Cited

OTHER PUBLICATIONS

Gillies, et al., "MRI of the Tumor Microenvironment," Journal of Magnetic Resonance Imaging, Oct. 2002, pp. 430-450, vol. 16, Issue 4.
Haq, et al., "A Data-Driven Approach to Prostate Cancer Detection From Dynamic Contrast Enhanced MRI," Computerized Medical Imaging and Graphics, Apr. 2015, pp. 37-45, vol. 41.
International Search Report and Written Opinion in International Application No. PCT/US2017/040456 dated Oct. 19, 2017 (14 pages).
Irani, et al., "Motion Analysis for Image Enhancement: Resolution Occlusion, and Transparency," Journal of Visual Communication and Image Representation, Dec. 1993, pp. 324-335, vol. 4, No. 4.
Kwak, et al., "Automated Prostate Cancer Detection Using T2-Weighted and High-B-Value Diffusion-Weighted Magnetic Resonance Imaging," The International Journal of Medical Physics Research and Practice, May 2015, pp. 2368-2378, vol. 42, Issue 5.
Kwak, et al., "Correlation of Magnetic Resonance Imaging With Digital Histopathology in Prostate," International Journal of Computer Assisted Radiology and Surgery, Apr. 2016, pp. 657-666, vol. 11, Issue 4.
Kwak, et al., "Prostate Cancer: A Correlative Study of Multiparametric MR Imaging and Digital Histopathology," Radiology, Oct. 2017, pp. 1-10, vol. 285, Issue 1.
Langer, et al., "Prostate Cancer Detection With Multi-parametric MRI: Logistic Regression Analysis of Quantitative T2, Diffusion-Weighted Imaging, and Dynamic Contrast-Enhanced MRI," Journal of Magnetic Resonance Imaging, Aug. 2009, pp. 327-334, vol. 30, Issue 2.
Li, et al., "Cell Membrane Water Exchange Effects in Prostate DCE-MRI," Journal of Magnetic Resonance, May 2012, pp. 77-85, vol. 218.
Maani, et al., "Voxel-Based Texture Analysis of the Brain," PLOS ONE, Mar. 10, 2015, pp. 1-19.
Maenpaa, et al., "Texture Analysis With Local Binary Patterns," WSPC, May 13, 2004, pp. 1-20, vol. 8, Issue 19.
Method for Determining In Vivo Tissue Biomarker Characteristics Using Multiparameter MRI Matrix Creation and Big Data Analytics (Draft application), 22 pages.
Moffat, et al., "Functional Diffusion Map: A Noninvasive MRI Biomarker for Early Stratification of Clinical Brain Tumor Response," Proceedings of the National Academy of Sciences, Apr. 2005, pp. 5524-5529, vol. 102, Issue 15.
Moradi, et al., "Multiparametric MRI Maps for Detection and Grading of Dominant Prostate Tumors," Journal of Magnetic Resonance Imaging, Jun. 2012, pp. 1403-1413 vol. 35, Issue 6.
Nasrollahi, et al., "Super-resolution: A Comprehensive survey," Machine Vision & Applications, Aug. 2014, pp. 1423-1468, vol. 25, Issue 6.
Niaf, et al., "Computer-Aided Diagnosis of Prostate Cancer in the Peripheral Zone Using Multiparametric MRI," Physics in Medicine Biology, May 2012, pp. 3833-3851, vol. 57, No. 12.
Non-Final Office Action on U.S. Appl. No. 15/640,107 dated Jan. 23, 2019.
Non-Final Office Action on U.S. Appl. No. 15/925,082 dated Jul. 24, 2018.
Non-Final Rejection Office Action in U.S. Appl. No. 14/821,703 dated Mar. 22, 2017 (56 pages).
Non-Final Rejection Office Action on U.S. Appl. No. 15/165,644 dated Nov. 30, 2017 (40 pages).
Notice of Allowance in U.S. Appl. No. 14/821,703 dated Oct. 5, 2017 (11 pages).
Oto, et al., "Diffusion-Weighted and Dynamic Contrast-Enhanced MRI of Prostate Cancer: Correlation of Quantitative MR Parameters With Gleason Score and Tumor Angiogenesis," American Journal of Roentgenology, Dec. 2011, pp. 1382-1390, vol. 197, No. 6.
Padhani, et al., "Reproducibility of Quantitative Dynamic MRI of Normal Human Tissues," NMR in Biomedicine, Apr. 2002, pp. 143-153, vol. 15, Issue 2.
Peng, et al., "Quantitative Analysis of Multiparametric Prostate MR Images: Differentiation Between Prostate Cancer and Normal Tissue and Correlation with Gleason Score—A Computer-aided Diagnosis Developmental Study," Radiology, Jun. 2013, pp. 787-796, vol. 267, No. 3.
Purysko, et al., "LI-RADS: A Case-based Review of the New Categorization of Liver Findings in Patients With End-Stage Liver Disease," RadioGraphics, Nov.-Dec. 2012, pp. 1977-2012, vol. 32, Issue 7.
Rijpkema, et al., "Method for Quantitative Mapping of Dynamic MRI Contrast Agent Uptake in Human Tumors," Journal of Magnetic Resonance Imaging, Oct. 2001, pp. 457-463, vol. 14, Issue 4.
Roberts, et al., "The Effect of Blood Inflow and B1-Field Inhomogeneity on Measurement of the Arterial Input Function in Axial3D Spoiled Gradient Echo Dynamic Contrast-Enhanced MRI," Magnetic Resonance in Medicine, Jan. 2010, pp. 108-119, vol. 65, Issue 1.
Senseney, et al., "Tumor Treatment Response Identification Using Combination Post-Treatment Mapping to Quantify Voxel-Wise Multiparameter MRI Biomarker Changes: A Simulation Study," International Symposium on Biomedical Imaging, May 2012, Barcelona, Spain.
Shah, et al., "Decision Support System for Localizing Prostate Cancer based on Multiparametric Magnetic Resonance Imaging," Medical Physics, Jul. 2012, pp. 4093-4103, vol. 39, No. 7.
US Office Action on U.S. Appl. No. 14/821,700 dated May 31, 2018.
Wang, et al., "Computer Aided-Diagnosis of Prostate Cancer on Multiparametric MRI: A Technical Review of Current Research," BioMed Research International, Aug. 2014, pp. 1-12, vol. 2014.
Yang, et al., "Comparison of Quantitative Parameters in Cervix Cancer Measured by Dynamic Contrast 2013 Enhanced MRI and CT," Magnetic Resonance in Medicine, Jun. 2010, pp. 1601-1609, vol. 63, Issue 6.
Yang, et al., "Reproducibility Assessment of a Multiple Reference Tissue Method for Quantitative Dynamic Contrast Enhanced 2013 MRI Analysis," Magnetic Resonance in Medicine, Apr. 2009, pp. 851-859, vol. 61, Issue 4.
Non-Final Office Action on U.S. Appl. No. 14/821,700 dated Apr. 28, 2020.
Notice of Allowance on U.S. Appl. No. 15/640,107 dated Mar. 10, 2020.
3D Human Models from 1D, 2D & 3D Inputs @3DBODY.TECH Oct. 17, 2018. Retrieved from the Internet on Feb. 17, 2021 URL: https://www.slideshare.net/AlfredoBallesterFern/3-dbt2018-id36ballesterv04pdf.
CORADS-AI—Grand Challenge. Retrieved from the Internet on Feb. 17, 2021 URL: https://github.com/microsoft/InnerEye-DeepLearning.
Extended European Search Report in EP 18788304.6 dated Jan. 13, 2021 (9 pages).
GitHub—Microsoft InnerEye DeepLearning Medical Imaging Deep Learning library to train and deploy models on Azure Machine Learning and Azure Stack. Retrieved from the Internet on Feb. 17, 2021 URL: https://grand-challenge.org/algorithms/corads-ai/.
Lessmann et al., Automated Assessment of COVID-19 Reporting and Data System and Chest CT Severity Scores in Patients Suspected of Having COVID-19 Using Artificial Intelligence. Radiology: vol. 298: No. 1—Jan. 2021, https://pubs.rsna.org/doi/10.1148/radiol.2020202439.
MedSeg—free medical segmentation online. Retrieved from the Internet on Feb. 17, 2021 URL: https://www.medseg.ai.
Photo Tourism: Exploring Photo Collections in 3D. Retrieved from the Internet on Feb. 17, 2021 URL: http://phototour.cs.washington.edu/Photo_Tourism.pdf.
Point set registration—Wikipedia. Retrieved from the Internet on Feb. 17, 2021 URL: https://en.wikipedia.org/wiki/Point_set_registration.
Project InnerEye—Democratizing Medical Imaging AI—Microsoft Research. Retrieved from the Internet on Feb. 17, 2021 URL:

(56) References Cited

OTHER PUBLICATIONS https://www.microsoft.com/en-us/research/project/medical-image-analysis/.

\* cited by examiner

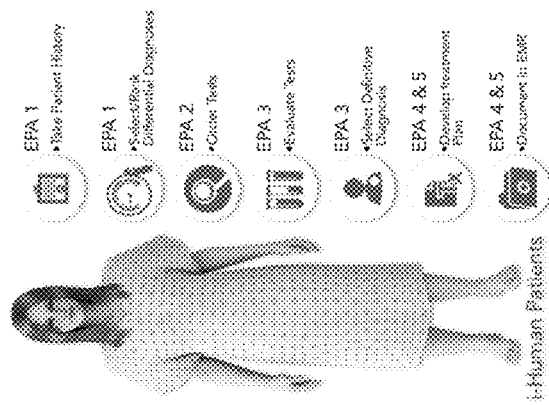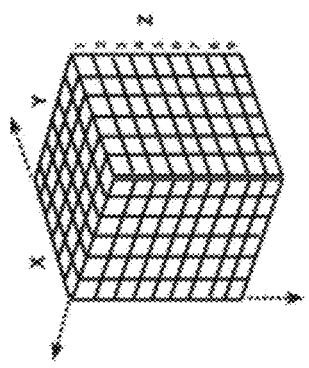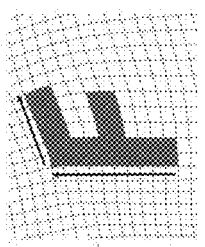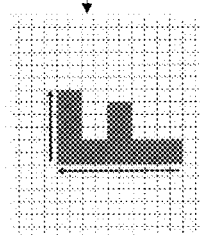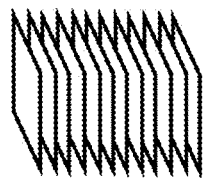
Fig. 1 (Prior Art)

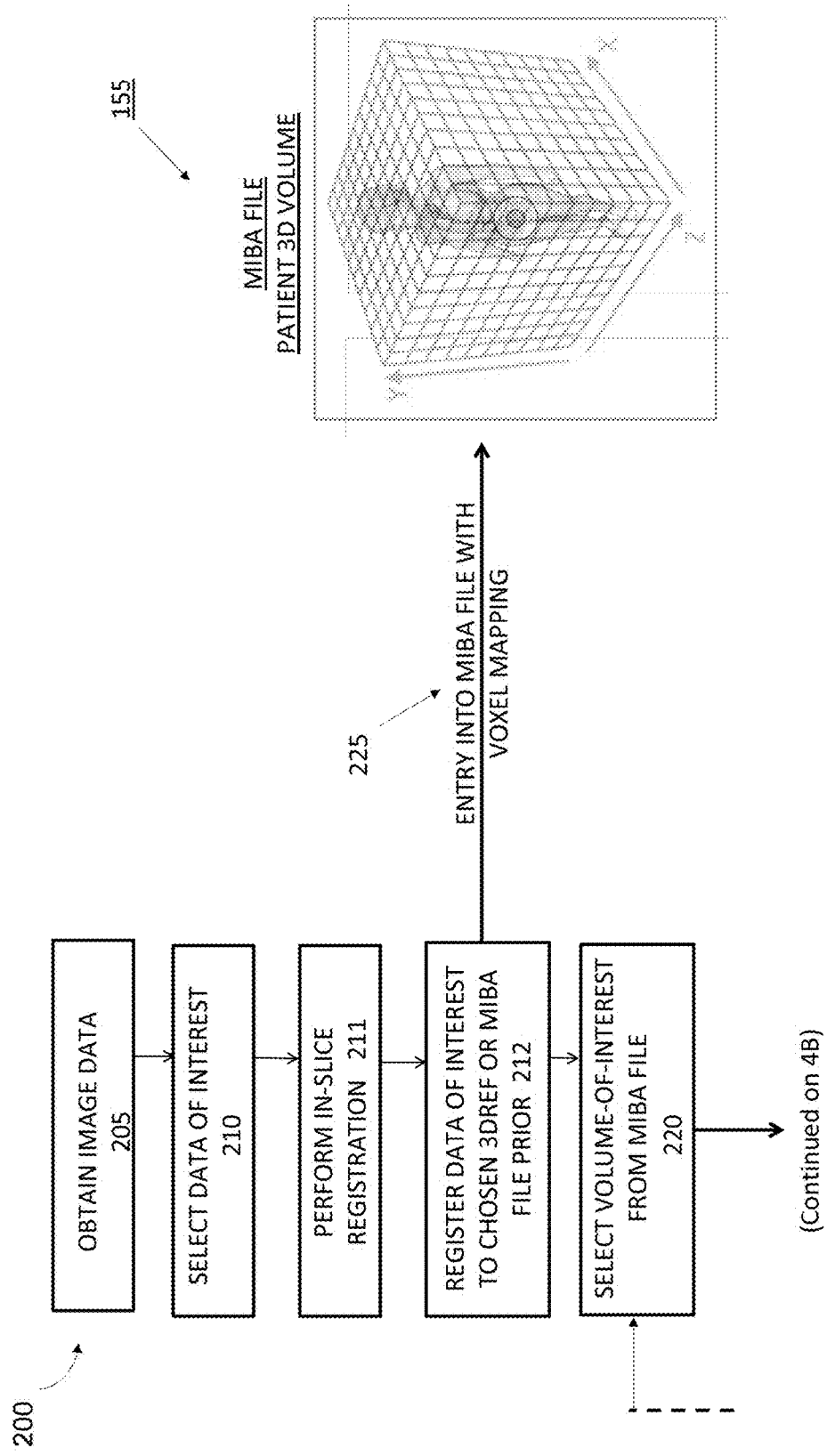

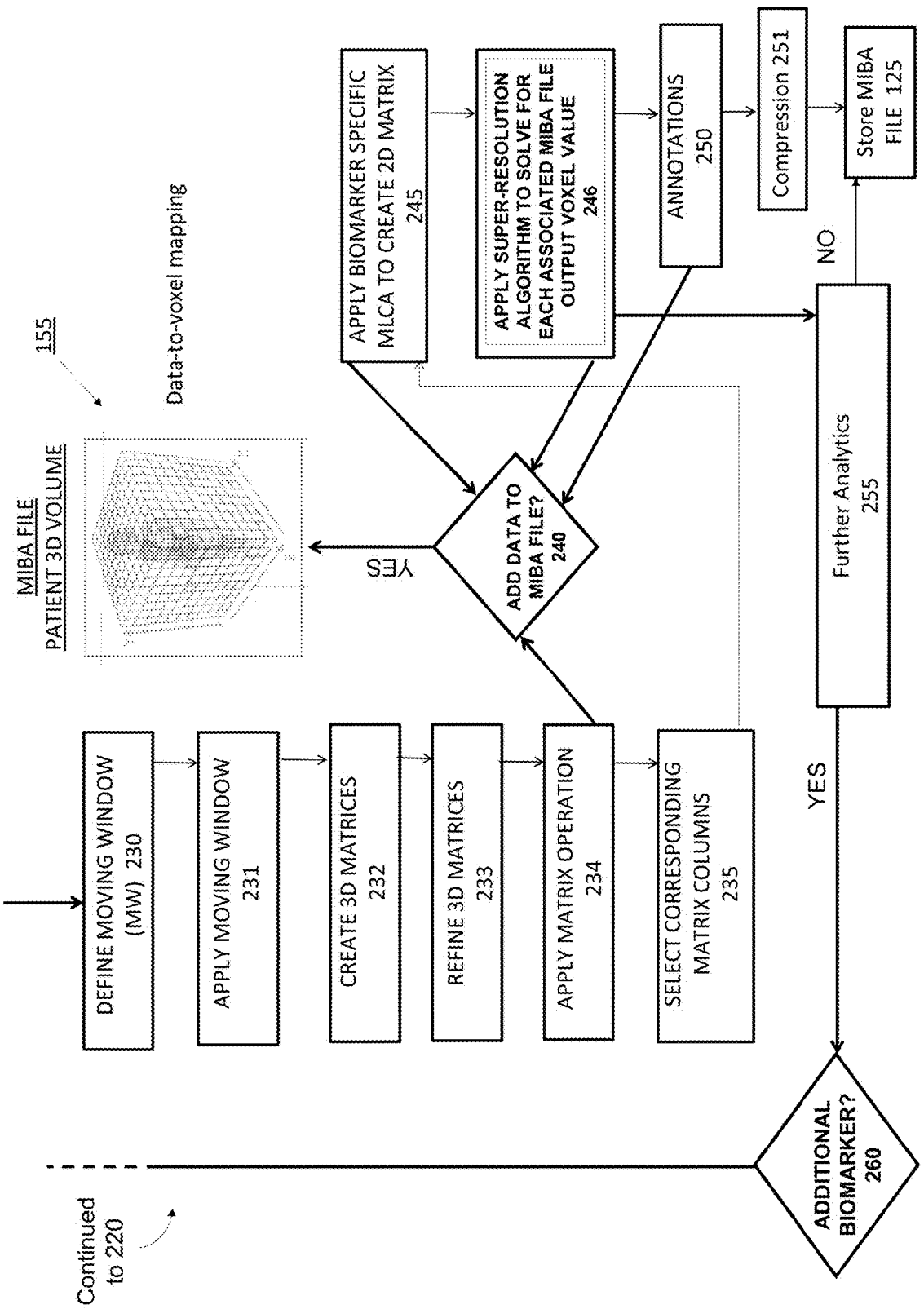

| VOXEL_CODE (X,Y,Z) | A_SoD_T1 | A_SoD_T2 | A_SoD_DWI | B_SoD_T1 | B_SoD_T2 | B_SoD_DWI | C_SoD_T1 | etc... |
|---|---|---|---|---|---|---|---|---|
| 1,1,1 | 500 | 2000 | 453 | | | | | |
| 2,1,1 | 345 | 1456 | 123 | | | | | |
| 3,1,1 | 453 | 3421 | 345 | | | | | |
| 4,1,1 | 564 | 1432 | 234 | | | | 564 | |
| 5,1,1 | 123 | 2341 | 654 | | | | 123 | |
| 6,1,1 | 765 | 1231 | 765 | | | | 765 | |
| 1,2,1 | 453 | 560 | 345 | | | | 564 | |
| 2,2,1 | 123 | 1234 | 254 | 345 | 1234 | 2351 | 123 | |
| 3,2,1 | 345 | 2351 | 334 | 254 | 1654 | 1545 | 765 | |
| 4,2,1 | 234 | 1545 | 1231 | 334 | 1345 | 1323 | 453 | |
| 5,2,1 | 654 | 1323 | 560 | 234 | 1432 | 1454 | 567 | |
| 6,2,1 | 765 | 1454 | 1234 | 567 | 1653 | 345 | 435 | |
| 1,3,1 | | | | 435 | 1324 | 254 | 322 | |
| 2,3,1 | | | | 322 | 1456 | 334 | 234 | |
| 3,3,1 | | | | 234 | 1545 | 1231 | 654 | |
| 4,3,1 | | | | 654 | 1323 | 560 | | |
| 5,3,1 | | | | 765 | 1454 | 1234 | | |
| 6,3,1 | | | | 123 | 2341 | 654 | | |
| 1,4,1 | | | | 765 | 1231 | 765 | | |
| etc... | | | | | | | | |

Fig. 10

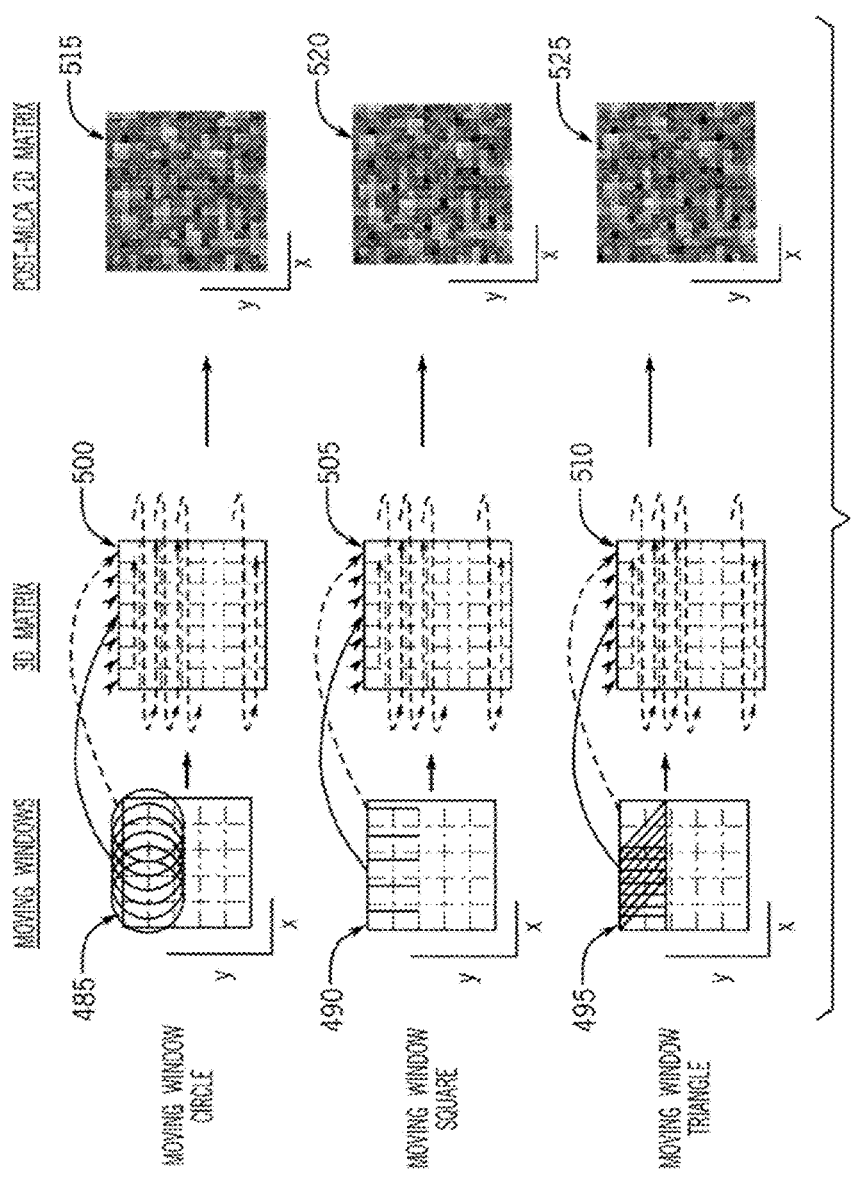

Fig. 22

← 155a  mark for database collection image annotation data

| VOXEL CODE (X,Y,Z) | DICOM_m eta | age | ROI | ROI | ROI | single parameter | physician note | survey date |
|---|---|---|---|---|---|---|---|---|
| 1,1,1 | embed | 34 | a_roi | | | 400 | Surveillance 6 months | june 2019 |
| 2,1,1 | embed | 34 | a_roi | | | 400 | Surveillance 6 months | june 2019 |
| 3,1,1 | embed | 34 | a_roi | | | 400 | Surveillance 6 months | june 2019 |
| 4,1,1 | embed | 34 | a_roi | b_roi | | 400 | Upload to population database | june 2019 |
| 5,1,1 | embed | 34 | a_roi | b_roi | | 400 | | june 2019 |
| 6,1,1 | embed | 34 | a_roi | b_roi | | 400 | | june 2019 |
| 1,2,1 | embed | 34 | a_roi | b_roi | | 400 | | june 2019 |
| 2,2,1 | embed | 34 | a_roi | b_roi | | 400 | | june 2019 |
| 3,2,1 | embed | 34 | a_roi | b_roi | | 400 | | june 2019 |
| 4,2,1 | embed | 34 | | b_roi | | | | june 2019 |
| 5,2,1 | embed | 34 | | b_roi | | | | june 2019 |
| 6,2,1 | embed | 34 | | b_roi | | | | june 2019 |

155 →

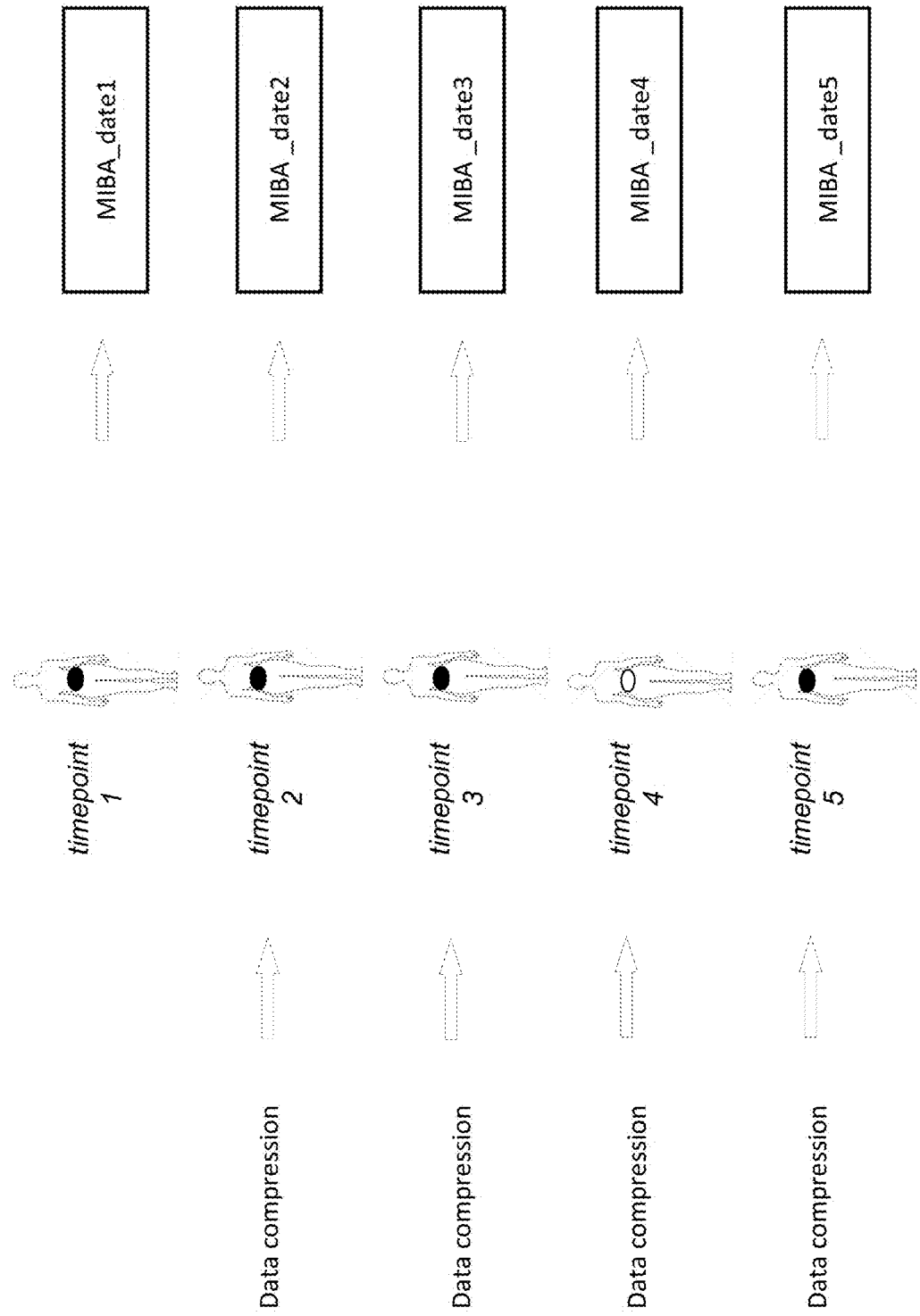

Fig. 24

MIBA_date5

| VOXEL CODE (X,Y,Z) | | SR | DICOM_meta | age | ROI | ROI | ROI | single parameter | physician note | survey date |
|---|---|---|---|---|---|---|---|---|---|---|
| 1,1,1 | ... source image and MW data ... | ... | | | | | | | | |
| 2,1,1 | ... | 0.9 | embed | 34 | a_roi | | | 400 | Surveillance 6 months | june 2019 |
| 3,1,1 | ... | 0.75 | embed | 34 | a_roi | | | 400 | Surveillance 6 months | june 2019 |
| 4,1,1 | ... | 0.8 | embed | 34 | a_roi | b_roi | | 400 | Surveillance 6 months | june 2019 |
| 5,1,1 | ... | 0.9 | embed | 34 | a_roi | b_roi | | 400 | Upload to population database | june 2019 |
| 6,1,1 | ... | 0.9 | embed | 34 | a_roi | b_roi | | 400 | | june 2019 |
| 1,2,1 | ... | 0.8 | embed | 34 | a_roi | b_roi | | 400 | | june 2019 |
| 2,2,1 | ... | 0.75 | embed | 34 | a_roi | b_roi | | 400 | | june 2019 |
| 3,2,1 | ... | 0.75 | embed | 34 | a_roi | b_roi | | 400 | | june 2019 |
| 4,2,1 | ... | 0.75 | embed | 34 | | b_roi | | | | |
| 5,2,1 | ... | 0.65 | embed | 34 | | b_roi | | | | |
| 6,2,1 | ... | 0.65 | embed | 34 | | b_roi | | | | |
| 1,3,1 | ... | 0.8 | embed | 34 | | b_roi | c_roi | | | |
| 2,3,1 | ... | 0.8 | embed | 34 | | b_roi | c_roi | | | |
| 3,3,1 | ... | 0.8 | embed | 34 | | b_roi | c_roi | | | |
| 4,3,1 | ... | 0.8 | embed | 34 | | | c_roi | | | |
| 5,3,1 | ... | 0.65 | embed | 34 | | | c_roi | | | |
| 6,3,1 | ... | 0.65 | embed | 34 | | | c_roi | | | |
| 1,4,1 | ... | | | | | | | | | |
| etc.... | | | | | | | | | | |

Fig. 29
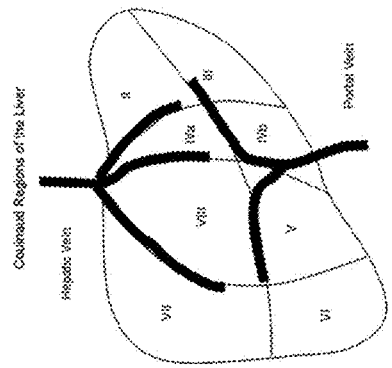
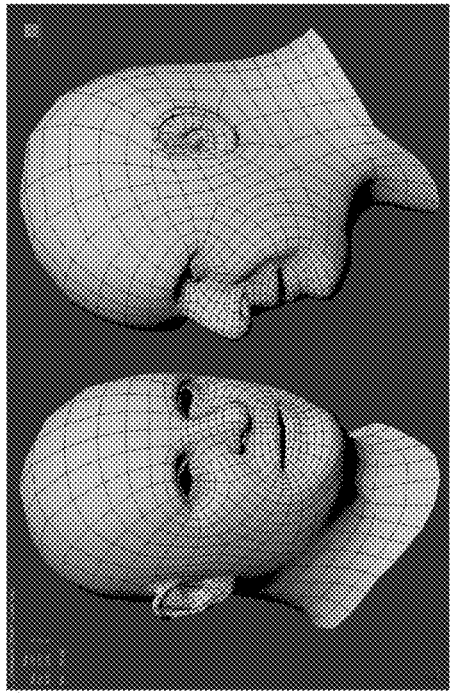
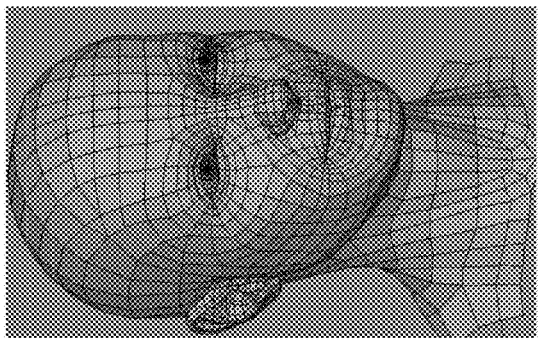
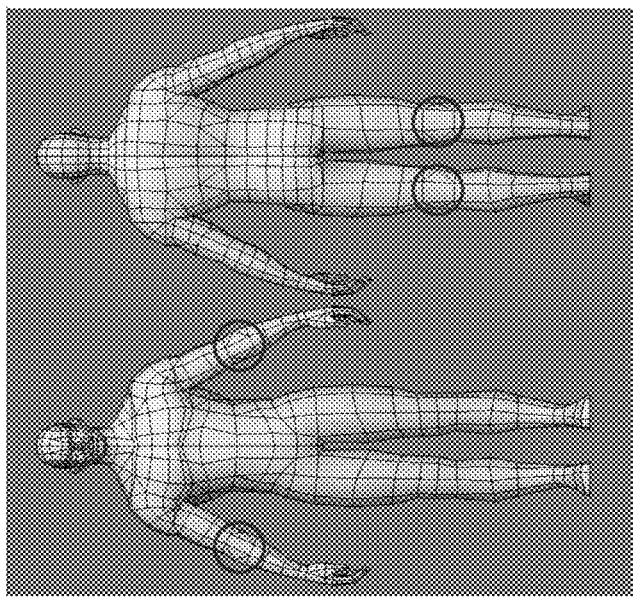
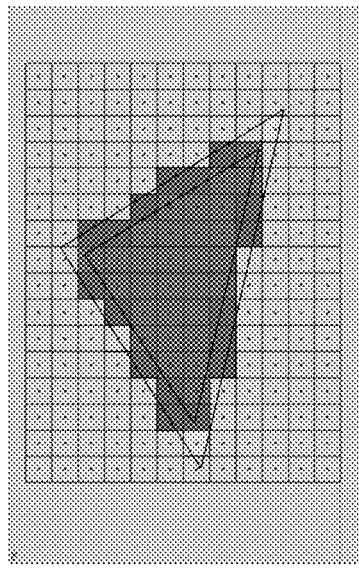

Parameter Descriptions

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| T1 | non-contrast | Spin-Lattice Relaxation Time = standard MRI "weighting" for T1, representing time constant for longitudinal relaxation | Decreased in tumors compared to normal tissue, but nonspecific | Various methods, spin echo methods provide excellent SNR and resolution | Standard MRI method with various methods including Spin Echo, Gradient Recall Echo, etc. | | T1 tumor < T1 normal |
| | T1-standard | | | | | Direct measures of signal at a given echo time (TE), signal strength is a function of shape of signal recovery (logarithmic) and TE | |
| | T1 mapping | | | Various techniques exist. Deoni is a more known method | Varies | Provides a direct measure of the T1 value of the tissue = a parameter which determines the shape of the T1 signal versus TE curve | |
| T1 post | | Signal on T1 images after intravenous contrast injection is increased | Allows great visualization of vessels containing contrast and tissues with contrast leakage | Various methods, spin echo methods provide excellent SNR and resolution | Standard MRI method with various methods including Spin Echo, gradient echo, etc. | | T1 post tumor > T1 post normal |
| | T1-post [C] | | | | | Measure of signal post contrast injection at a given TE | |
| [C] | T1-post [C] | Concentration of contrast is directly determined as a function of signal | Allows direct measures of MRI contrast concentration, used in DCE-MRI | Most often gradient recall echo (GRE) | Standard T1 methods | Mathematical modeling is used to determine [C] from known variables, including signal value | T1 post [C] > T1 post [C] normal |
| FLAIR | | "takes out" fluid signal | Mostly used in brain tumors and helps better delineate region of Tumor | Inversion recovery technique that eliminates signal from free fluid such as CSF | | | |

Fig. 30A

Parameter Descriptions

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| T2 | | Spin-Spin Relaxation Time ≈ standard MRI "weighting" for T2, representing time constant for transverse Relaxation | Increased in tumors compared to normal tissue, but nonspecific | Various methods, spin echo methods provide excellent SNR and resolution | Standard MRI method with various methods including Spin Echo, STIR, etc. | | T2 tumor > T2 normal |
| | T2-standard | | | | | Direct measures of signal at a given echo time TE, signal strength is a function of shape of signal recovery (exponential) and TE | |
| | T2 mapping | | | | | Provides a direct measure of the T2 value of the tissue ≈ a parameter which determines the shape of the T2 signal versus TE curve | |
| Ktrans | | Forward exchange constant ≈ index of vessel leakiness | Tumor vessels are more leaky than normal vessels | Dynamic Contrast-Enhanced MRI (DCE-MRI) | Contrast is injected into patient and serial T1 MRI images are obtained as contrast enters the tissue | Pharmacokinetic models are used that model motion of contrast molecules between vessel and the extracellular space | Ktrans tumor > Ktrans normal |
| | Ktrans "Tofts Model" (TM) | | | | | Different DCE-MRI software packages using TM include OHSU, VU, UP, ISM, BWH-GE, BWH-3D Slicer | |
| | Ktrans "Extended Tofts Model" (ETM) | | | | | Different DCE-MRI software packages using ETM include VU, UM, UW, BWH-GE | |
| | Ktrans "Shutterspeed Model" (SSM) | | | | | Different DCE-MRI software packages using SSM include OHSU, VU | |
| delta Ktrans (Δ Ktrans) | Delta Ktrans "Shutterspeed Model" (SSM) | Takes difference of Ktrans measured using SSM and TM | Research shows that this measure can be highly specific for cancers | DCE-MRI | Contrast is injected into patient and serial MRI images are obtained as contrast enters the tissue | Different DCE-MRI software packages using SSM include OHSU, VU | Δ Ktrans tumor > Δ Ktrans normal |

Fig. 30B

Parameter Descriptions

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| Ve | | Volume of Exchange = volume of the extracellular extravascular space | Contrast leak from vessels into the Ve and the size of this space can vary | DCE-MRI | Contrast is injected into patient and serial MRI images are obtained as contrast enters the tissue | Pharmacokinetic models are used that model motion of contrast molecules between vessel and the extracellular space | Varies |
| | Ve "Tofts Model" (TM) | | | | | Different DCE-MRI software packages using TM include OHSU, VU, UP, ISM, BWH-GE, BWH-3D Slicer | |
| | Ve "Extended Tofts Model" (ETM) | | | | | Different DCE-MRI software packages using ETM include VU, UM, UW, BWH-GE | |
| | Ve "Shutterspeed Model" (SSM) | | | | | Different DCE-MRI software packages using SSM include OHSU, VU | |
| Vb | | Volume of Blood in exchange with tissue | Vascularity varies with different tumors and can vary after treatment | DCE-MRI | Contrast is injected into patient and serial MRI images are obtained as contrast enters the tissue | Pharmacokinetic models are used that model motion of contrast molecules between vessel and the extracellular space | Varies |
| | Vb "Extended Tofts Model" (ETM) | Parameter only derived from the "Extended Tofts Model" (ETM) | | | | Different DCE-MRI software packages using ETM include VU, UM, UW, BWH-GE | |
| Dt | Dt IVIM | Measure of "true" diffusion without effects of "pseudodiffusion" and signal from moving blood | Cancers have higher water restriction than normal tissues | IVIM from Diffusion-Weighted Imaging (DWI) MRI | Gradients at various "b values" of weighting are applied and the signal in tissue is measured at each b value | Simple IVIM mathematical model is used to determine Dt from signal decay at various b values, b=0 and other low b values are used for calculation. | Dt tumor < Dt normal |

Fig. 30C

Parameter Descriptions

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| Dp | Dp IVIM | Measure of pseudodiffusion | | IVIM from DWI MRI | Gradients at various "b values" of weighting are applied and the signal in tissue is measured at each b value | Simple IVIM mathematical model is used to determine fp from signal decay at various b values. b=0 and other low b values are used for calculation. | Varies |
| fp | fp IVIM | Fractional plasma volume | Vascularity varies with different tumors and can vary after treatment | IVIM from DWI MRI | Gradients at various "b values" of weighting are applied and the signal in tissue is measured at each b value | Simple IVIM mathematical model is used to determine fp from signal decay at various b values. b=0 and other low b values are used for calculation. | Varies |
| tau | tau "Shutterspeed Model" (SSM) | Tau is an extra parameter added to the SSM to model time for protons to complex with MRI contrast | Research shows that this measure can be highly specific for cancers, likely related to Sodium levels | DCE-MRI | Contrast is injected into patient and serial MRI images are obtained as contrast enters the tissue | Different DCE-MRI software packages using SSM include OHSU, VU | tau tumor > tau normal |
| Hyperpolarized MRI | Various types of Hy MRI parameters | Hyperpolarized C13 substrates injected and imaged | Can image many metabolites, as well as quantify pH | | | | |
| ADC | | Measure of Restriction of Random Water Motion | Cancers have higher water restriction than normal tissues | DWI MRI | Gradients at various "b values" of weighting are applied and the signal in tissue is measured at each b value | | ADC tumor < ADC normal |
| | ADC standard | | | | | b value of "zero" is first measured = no gradient. Signal at various other b values are then also measured. ADC is the slope of the log of the signal decay. Signal does not decay as quickly in tumors. | |
| | ADC high b-values | | | | | ADC is measured only for high b values excluding b=0, typically high b values range up to 1000 | |

Fig. 30D

Parameter Descriptions

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| ADCo | ADCo Oscillating gradient spin echo (OGSE) | Better able to probe intracellular signal | Cancers have higher water restriction than normal tissues | Oscillating gradients with DWI MRI | OGSE at various "b values" of weighting, but the gradients are oscillated | ADC is measured in a similar manner to standard ADC | ADC tumor < ADC normal |
| kep | | Reverse exchange constant = index of vessel leakiness | Tumor vessels are more leaky than normal vessels | DCE-MRI | Contrast is injected into patient and serial MRI images are obtained as contrast enters the tissue | Pharmacokinetic models are used that model motion of contrast molecules between vessel and the extracellular space | kep tumor > kep normal |
| | kep "Tofts Model" (TM) | | | | | Different DCE-MRI software packages using TM include OHSU, VU, UP, ISM, BWHGE, BWH-3D Slicer | |
| | kep "Extended Tofts Model" (ETM) | | | | | Different DCE-MRI software packages using ETM include VU, UM, UW, BWH-GE | |
| | kep "Shutterspeed Model" (SSM) | | | | | Different DCE-MRI software packages using SSM include OHSU, VU | |
| AUC | | Area under the curve of signal from contrast entering tumor over time | Provides a "semi-quantitative" measure of tumor vessel leakage | DCE-MRI | Contrast is injected into patient and serial MRI images are obtained as contrast enters the tissue | Graphs are created of signal from contrast entering tumor over time for each voxel and AUC is calculated | AUC tumor > AUC normal |
| TTP | | Time to peak = measure of point of maximal contrast on tumor curve | Provides a "semi-quantitative" measure, mostly indicative of vascularity | DCE-MRI | Contrast is injected into patient and serial MRI images are obtained as contrast enters the tissue | Graphs are created of signal from contrast entering tumor over time for each voxel and TTP is calculated | TTP tumor > TTP normal |
| MPE | | Maximal peak enhancement = maximal concentration in tumor during tumor time curve | Provides a "semi-quantitative" measure, mostly indicative of vascularity | DCE-MRI | Contrast is injected into patient and serial MRI images are obtained as contrast enters the tissue | Graphs are created of signal from contrast entering tumor over time for each voxel and MPE is calculated | MPE tumor > MPE normal |

Fig. 30E

Parameter Descriptions

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| Df | Df biexponential | Fast diffusion component | Index of "fast" diffusion at low b values | DWI MRI | Gradients at various "b values" of weighting are applied and the signal in tissue is measured at each b value | A biexponential fit model is applied to the graph of signal decay | Varies |
|  | Ds biexponential | Slow diffusion component | Index of "slow" diffusion at high b values |  |  |  | Ds tumor > Ds normal |
| D |  | Diffusion Parameter "fit" from modeling of the signal decay | Cancers have higher water restriction than normal tissues | DWI MRI | Gradients at various "b values" of weighting are applied and the signal in tissue is measured at each b value |  |  |
|  | D stretched biexponential |  |  |  |  | A "stretched" biexponential fit model is applied to the graph of signal decay | D tumor > D normal |
|  | D kurtosis |  |  |  |  | A kurtosis fit model is applied to the graph of signal decay | D tumor > D normal |
| CBF |  | Measures os signal from moving blood | Tumors often have increased blood flow | Different MRI acquisitions are used for CBF measures |  |  |  |
|  | CBF-ASL |  |  | Various ASL pulse sequences exist | Arterial Spin Labeling (ASL) "tags" moving blood and measures signal in a volume of interest | Signal is directly measured |  |
|  | CBF-DSC | Only used for brain tumors, does not work in body imaging |  | Various DSC, but usually a Echo Planar sequence is used | T2* effects measure signal drop after a bolus injection of contrast, degree of drop correlates with amount of signal from blood | Models of signal changes are used to extract parameters, most interesting of which are CBF and CBV | CBF tumor > CBF normal |

Fig. 30F

Parameter Descriptions

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| $R^*$ | | Index of oxygenation, BOLD imaging | Hypoxic regions of cancers are most resistant to various treatments | Intrinsic Susceptibility Imaging (ISI) using various pulse sequences sensitive to $T2^*$ Effects | $T2^*$ effects measure signal in regions of relative decreased oxygenation | | $R^*$ tumor $<$ $R^*$ normal |
| RSI-CM | | Measure of Restriction of INTRACELLULAR Random Water Motion | Better differentiates tumor from normal and edema | Resonance Spectral Imaging (RSI) from DWI MRI | Gradients at various "b values" up to 4000 are applied and the signal in tissue is measured at each b value | A linear mixture model is used to model signal across b values, does not assume Gaussian like DTI (below) | RSI-CM tumor $>$ RSI-CM normal |
| Various DTI Tensor Parameters | tensor measure(s) | Various tensor parameters provide info on direction of water diffusion | Some good recent applications for tumors, but mainly used for tractography | Diffusion Tensor Imaging (DTI) from DWI MRI | Gradients are applied in many directions using a few b values | Models are applied to determine direction of water motion based an assumption of a gaussian distribution | Varies |
| Na | | Measures sodium (Na) content in tissues by exciting Na instead of H (protons) | Elevated sodium is very specific for cancer | Special coils etc for Sodium Imaging, Na imaging will improve with increasing field strength and new 7 Tesla MRI machines | Na is excited instead of H, and signal is detected | Signal is measured at each voxel and correlates to Na levels | Na tumor $>$ Na normal |
| Spectroscopy MRI | | Imaging of various peaks following excitation, for example can quantify increased lactate in tumors | | | | | |
| CEST | Various types of CEST parameters | Allows indirect detection of metabolites with exchangeable protons using special contrast agents | | T1 post contrast method | | | |
| MRI Fingerprinting | | New method that allows for simultaneous quantification of multiple MR properties in tissues during a single acquisition | Potentially faster, as well as more sensitive and specific MR method | | | | |

Fig. 30G

Parameter Descriptions

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| MRI contrast agents | | Various contrast agents available or being developed to complex with Gadolinium (the standard MRI contrast agent) | These developing techniques offer the potential for enormous variety in specific characterization of cancer receptors, metabolites, stem cell tracking etc. | Usually standard T1 sequences | Contrast agent injected and MRI images obtained | | |
| | Gadoxetate (Eovist) | Specific for uptake by liver hepatic cells | Great for sensitive identification of liver mets | Currently FDA approved and clinically used | | | E tumor < E normal |
| | Receptor Imaging | Various probes to target receptors overexposed in cancers | Examples include hormone receptors in breast cancer, EGFR important for mets, etc. | | | | |
| | USPIO | Very sensitive iron oxide agents, signal loss with uptake in normal lymph nodes | Great for identifying lymph nodes metastasis in vivo | | T2* effects | | |
| | F19 MRI | Used to label and track stem cells | | | | | |
| | nanoparticles/ theranostics | Huge area of research aimed at creating nanoparticles to enter cancer cells and deliver treatment | Usually complexed with MRI contrast agent for visualization | | | | |

Fig. 30H

Parameter Descriptions

| "Parent" Parameter | Subset Parameter | Brief Description | Why useful? | Brief Description of Data Processing |
|---|---|---|---|---|
| SUVmax from PET | | Standard PET/CT measures uptake of F18, a measure of glycolysis | In general, nuclear medicine techniques offer more signal from a "smaller" event – the disadvantage is poor resolution | CT or MRI and PET are registered and SUVmax is determined after calibration for CT attenuation etc. |
| | SUVmax F18-FDG | | Some tumor types and advanced tumors have increased uptake, but only for select cancers | |
| | SUVmax F18-Choline | | Has shown increased specificity for prostate cancer metastasis | |
| | SUVmax F18-PLT | | More sensitive for some cancers | |
| PET tracers | | Various PET tracers are under investigation for targeted specific receptors etc. | | |

Fig. 30I

Parameter Descriptions

| "Parent" Parameter | Subset Parameter | Brief Description | Why useful? | Brief Description of Analysis Technique | How do parameter measures compare to normal tissue? |
|---|---|---|---|---|---|
| Heterogeneity Features | | Measures of heterogeneity have shown strong correlation with tumor genetics = radiogenomics | Models can be applied to CT or MRI or PET | | Heterogeneity tumor > heterogeneity normal |
| | Hot Spot Measures | Regions of interest (ROIs) are placed only in mapping areas showing largest or smallest values | Better correlation: to tumor grading, staging, etc. | | |
| | Histogram methods | Provides info on histograms, for example value for peak height, standard deviation, skew, kurtosis, etc. | Some studies show this analysis correlates better to tumor characteristics than hot spot analysis | | |
| | Xf | Measures of fraction of a certain parameter, for example, fraction of enhancing voxels | Better correlation: to tumor grading, staging, etc. | | |
| | textural analysis | Haralick method most often used | | | |
| | fractal techniques | Imposing regular grids of a range of scales on a binary object in question and then counting the number of grid elements (boxes) that are occupied by the object at each scale | | | |
| | Minkowski functionals | Analyse binarized images over a range of thresholds and also quantify space-filling properties of tumors | | | |
| | Clustering Techniques | Multi-spectral analyses use pattern recognition techniques that simultaneously analyze images to identify voxel clusters in a multi-dimensional feature space. A classifier then groups individual voxels together based on their similarities and differences. | Starts to approach of techniques, limitation with these techniques is for demonstrating changes after treatment due to changing sizes of subregions. Other research (i.e., FDM) indicates that ROI before and after treatment should be held constant. | Group multiparameter data with clustering searches for voxels demonstrating certain patterns | |

AI ANALYTICS — Various methods allow use of neural networks using labelled image data to create automated annotations on images, such as automated segmentations of anatomy and automated diagnoses.

Fig. 30J

*Parameter Descriptions*

| "Parent" Parameter | Brief Description |
|---|---|
| Raman Imaging | Images based on Raman Spectrum, resolution to 25nm, human scale Raman Spectroscopy and contrast agents are being developed. |
| Micro_PET | Animal imaging only, with multiple probes with PET |
| Bioluminescence Optical Imaging | Animal imaging only, fluescent tags to markers in vivo |
| Ultrasound | US is generally only used for clinical identification. Some research with ultrasound "molecular imaging" tracers which could be married with treatment options such as High Intensity Focused Ultrasound. US is also used to identify biopsy location and to fuse images with other modalities such as MRI. US has a limited role for quantification of parameter measures. |
| nano-MRI | Evolving technology using MRI for nanoscale imaging. |

Fig. 30K

SYSTEM AND METHOD FOR CREATING, QUERYING, AND DISPLAYING A MIBA MASTER FILE

CROSS-REFERENCES TO RELATED PATENT APPLICATIONS

This present application claims priority from U.S. Provisional Patent Application No. 62/488,581, filed on Apr. 21, 2017, and U.S. Provisional Patent Application No. 62/580,543, filed on Nov. 2, 2017, both of which are incorporated by reference in their entirety herein.

TECHNICAL FIELD

The present disclosure relates to a system and method for creating highly embedded medical image files with high density bioinformatics and annotation data for use in patient medical care using image and data displays in multimedia devices.

BACKGROUND

The following description is provided to assist the understanding of the reader. None of the information provided or references cited is admitted to be prior art.

Precision medicine is a medical model that proposes the customization of healthcare practices by creating advancements in disease treatments and prevention by taking into account individual variability in genes, environment, and lifestyle for each person. In this model, diagnostic testing is often deployed for selecting appropriate and optimal therapies based on the context of a patient's genetic content or other molecular or cellular analysis. A biomarker is a characteristic that is objectively measured and evaluated as an indicator of normal biological processes, pathogenic processes, or pharmacologic responses to a treatment. Such biomarkers are particularly useful in cancer diagnosis and treatment, as well as radiogenomics. Radiogenomics is an emerging field of research where cancer imaging features are correlated with indices of gene expression. Identification of new biomarkers, such as for radiogenomics, will be facilitated by advancements in big data technology. Big data represents the information assets characterized by such a high volume, velocity and variety to require specific technology and analytical methods for its transformation into value. Big data is used to describe a wide range of concepts: from the technological ability to store, aggregate, and process data, to the cultural shift that is pervasively invading business and society, both drowning in information overload. Machine learning methods, such as classifiers, can be used to output probabilities of features in sets of individual patient medical data based on comparisons to population-based big data datasets.

Extrapolated over an entire population, these trends in clinical data volume explosion and fundamental data management reorganization represent both a tremendous opportunity and a significant challenge. Although the benefits of individual patient stewardship of their own medical data have clear advantages, these complex datasets cannot be safely interpreted by individuals without a substantial medical and technical background. Therefore, new basic organizational systems are needed to successfully deploy the data in a healthcare environment and assure proper recording and communication with the patient.

SUMMARY

In accordance with one aspect of the present disclosure, a method is disclosed. The method includes receiving, by a medical imaging bioinformatics annotated ("MIBA") system, image data from a sample, registering, by the MIBA system, the image data to a three-dimensional (3D) model selected from a population database for obtaining source data, and receiving selection, by the MIBA system, of a volume of interest. The method also includes extracting, by the MIBA system, a portion of the source data corresponding to the volume of interest, defining, by the MIBA system, a moving window, applying, by the MIBA system, the moving window to the portion of the source data for obtaining a dataset, and applying, by the MIBA system, a convolution algorithm to the dataset for obtaining convoluted data. The method further includes creating, by the MIBA system, a MIBA master file from the convoluted data and determining, by the MIBA system, a probability of a biomarker from the MIBA master file.

In accordance with another aspect of the present disclosure, a medical imaging bioinformatics annotated ("MIBA") system is disclosed. The MIBA system includes a database configured to store a MIBA master file and a MIBA creation unit. The MIBA creation unit is configured to receive image data from a sample, register the image data to a three-dimensional (3D) model selected from a population database for obtaining source data, and extract voxel data from the source data and enter the voxel data into the database. The MIBA creation unit is also configured to receive selection of a volume of interest, extract a portion of the voxel data from the database corresponding to the volume of interest, and create the MIBA master file from the portion of the voxel data. The MIBA creation unit is additionally configured to store the MIBA master file in the database. The MIBA system further includes a MIBA query system configured to receive the MIBA master file from the database, extract data from the MIBA master file in response to the query, and present the extracted data on an output interface.

In accordance with yet other aspects of the present disclosure, another method is disclosed. The method includes creating, by a medical imaging bioinformatics annotated ("MIBA") system, a MIBA master file. Creating the MIBA master file includes receiving, by the MIBA system, image data from a sample, performing, by the MIBA system, a first registration on the image data for obtaining in-slice registered data, and performing, by the MIBA system, a second registration for registering the in-slice registered data to a three-dimensional (3D) model selected from a population database for obtaining source data. Creating the MIBA master file also includes extracting, by the MIBA system, voxel data from the source data and storing the voxel data in a MIBA database, receiving, by the MIBA system, selection of a volume of interest, extracting, by the MIBA system, a portion of the voxel data corresponding to the volume of interest, creating, by the MIBA system, the MIBA master file from the portion of the voxel data, and storing, by the MIBA system, the MIBA master file in the MIBA database. The method further includes receiving, by the MIBA system, a query, extracting, by the MIBA system, data from the MIBA master file in response to the query, and presenting, by the MIBA system, the extracted data on an output interface.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF DRAWINGS

The foregoing and other features of the present disclosure will become more fully apparent from the following description and appended claims, taken in conjunction with the accompanying drawings. Understanding that these drawings depict only several embodiments in accordance with the disclosure and are therefore, not to be considered limiting of its scope, the disclosure will be described with additional specificity and detail through use of the accompanying drawings.

FIG. 1 illustrates at least some limitations of conventional DICOM images for medical imaging.

FIGS. 4A and 4B are example flowcharts outlining operations for creating the MIBA master file, in accordance with some embodiments of the present disclosure.

FIG. 10 illustrates another example of a portion of the MIBA database, in accordance with some embodiments of the present disclosure.

FIG. 17 shows multiple 2D matrices obtained for a particular region of interest from various moving windows, in accordance with some embodiments of the present disclosure.

FIG. 22 shows an example of an updated MIBA master file including the annotation data, in accordance with some embodiments of the present disclosure.

FIG. 23 shows multiple MIBA master files at varying time points, in accordance with some embodiments of the present disclosure.

FIG. 24 shows an example of the MIBA master file at one timepoint, in accordance with some embodiments of the present disclosure.

FIG. 29 shows examples of labeling anatomy in the MIBA master file, in accordance with some embodiments of the present disclosure.

FIGS. 30A-30K are charts of example matching parameters for use in analyzing image datasets, in accordance with some embodiments of the present disclosure.

DETAILED DESCRIPTION

Figure 2:
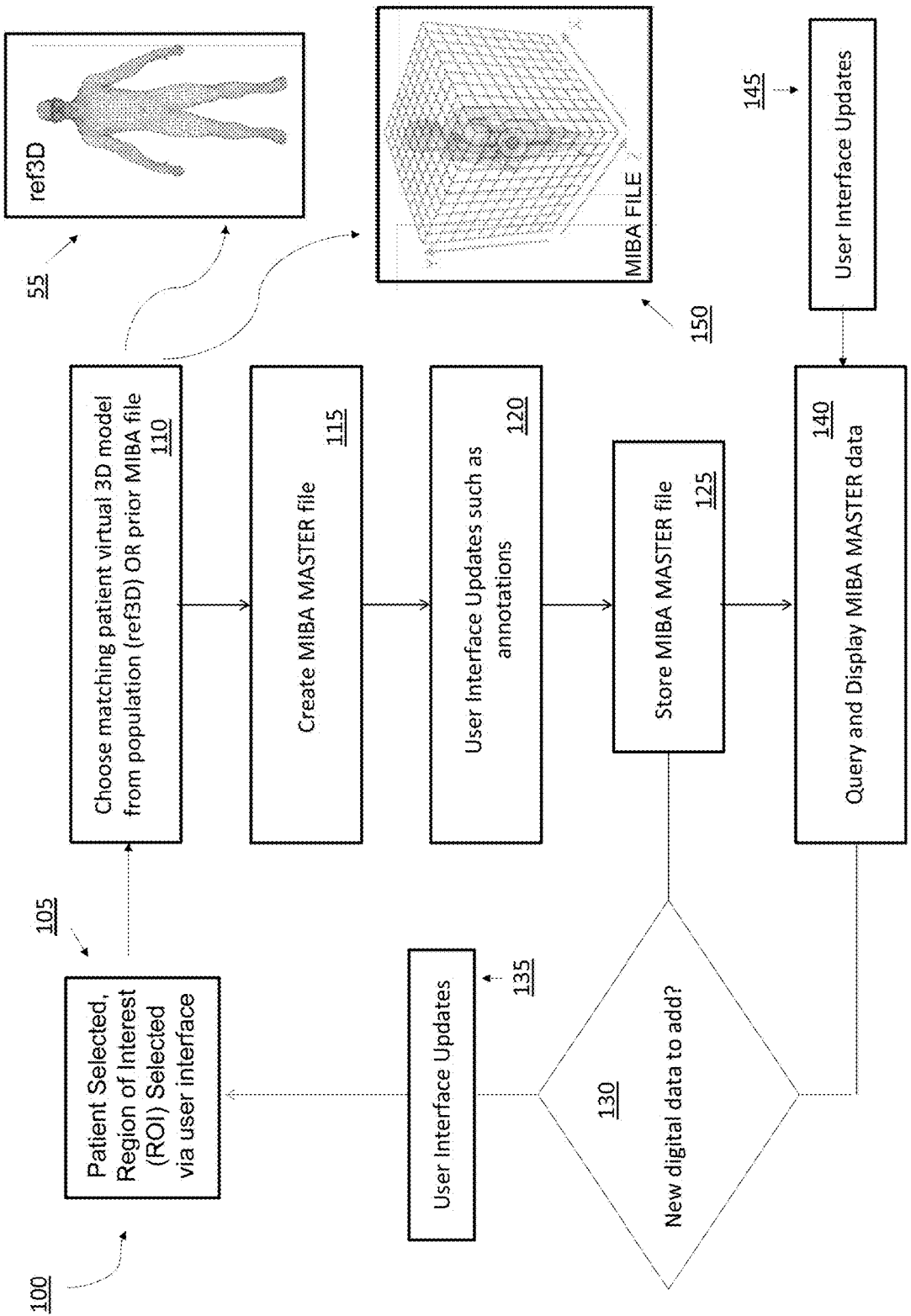
FIG. 2 is an example flowchart outlining operations for creating and using a Medical Imaging Bioinformatics Annotated master file" (MIBA master file), in accordance with some embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The present disclosure is directed to a new singular "rich data" medical imaging and biodata organizational system that is configured to power a new level of precision analytics and display of a patient's body for a new era of precision medicine. Therefore, systems and methods for creating and querying a new data structure, referred to herein as a "Medical Imaging Bioinformatics Annotated Master File" (MIBA master file), are described. The MIBA master file is a compilation of a variety of information pertaining to a sample (e.g., a patient, whether human or non-human). For example, in some embodiments, the MIBA master file may include a compilation of every voxel of the human body coded with multiple forms of metadata. The MIBA master file may additionally include information such as a date when the MIBA master file was created, any notes added by a user, specific information pertaining to one or more regions of interest of the sample, attributes of the sample (e.g., age, height, weight, etc.), type of image data collected from the sample, etc. The MIBA master file may include other types of data, as described herein, or as considered desirable to include in the MIBA master file. The MIBA master file is configured to be queried by associated computing systems and displayed in various forms, including for example, on virtual body maps, high resolution 3D displays of metadata, sparse data displayed on Avatars on smartphones, etc. Doctors may be able to edit MIBA master file, such as by creating markings of anatomical regions, text annotations, etc.

Conventionally, standard medical image files, called DICOM (Digital Imaging and Communications in Medicine) have been used for medical imaging purposes. FIG. 1 illustrates several limitations of using DICOM images for medical imaging. (A) DICOM images are individually acquired slices or anatomically segmented volumes of a human body. Each medical imaging study acquires a multitude of individual DICOM image files, akin to separate single pages in a book. A single medical imaging study today can take up memory roughly equivalent to 800 books, and experts predict each study memory will be roughly equivalent to 800,000 books, or 1 TB of memory, in the near future. Further, the number of DICOM images per patient study is increasing rapidly over time. For example, medical image DICOM volumes per patient study have been increasing, perhaps even exponentially, over the last years and these increases are projected to continue. If a single DICOM image is thought of as a single page in a book, past patient studies required the same memory as approximately 40 books, today's studies require approximately 800 books, and studies in the near future are projected to require approximately 800,000 books, or 1 TB, of memory. Further, DICOM images are stored in the PACS (Picture Archiving and Communication System)—a system that was developed in the 1980's when DICOM volumes were low and before widespread use of electronic health records (EHR). Although efforts have been pursued to integrate PACS with EHR, the systems suffer from core design limitations. These increasing volumes of non-collated DICOM, stored in an antiquated PACS, are causing increasing strains for healthcare professionals and limit needed progress for precision medicine. Thus, these DICOM image files are voluminous, non-collated (e.g., separated), and widely dispersed (e.g., in the form of individual slices or segmental volumes), and generally unsuitable for present day medical imaging purposes. Further, DICOM images consume a lot of memory, are not designed to be integrated with currently used systems, and are otherwise unmanageable. In addition, other digital medical data such as biopsy, genetics, and other clinical data is also exploding. DICOM image based systems are not able to keep pace with this exploding clinical data.

(B) State-of-the-art DICOM is based on a rigid Cartesian Coordinate System, which has limited multidimensionality (e.g., up to approximately 6 dimensions per voxel), such as those used for four dimensional (4D) flow MR imaging. A voxel is a unit of graphical information that defines a point in three-dimensional space, and here defined as a unit where all sides of the voxel form 90 degree angles. Thus, while current techniques using standard DICOM images allow for some advanced three-dimensional (3D) visualization, only limited current techniques integrates higher dimensions of imaging data into 3D files, such as time series flow information. With the advancement of precision medicine, core new medical imaging information technology solutions are needed to better integrate medical imaging files with other digital health information for many order higher dimensionality to create "rich data" datasets to optimize to power of precision analytics on human tissues. Human anatomy warping is a considerable challenge in medical imaging. For example, the liver may compress by 30% during breathing and edema surrounding a brain tumor may cause significant warping and lead to registration errors in trying to topologically map tumor tissue across various types of images and time-points. Thus, with limited multidimensionality, precise registrations remain a technical hurdle for medical imaging in attempts for precise image quantification using DICOM images. (C) Electronic Health Record (E.H.R.) companies may use "Patient Avatars" which create annotation on an artist-rendered likeness of the patient. These Avatars are anatomically incorrect and imprecisely topologically mapped. These Avatars also do not contain mapped patient precision medical imaging data which has been anatomically collated with the other digital health data. Thus, although patient avatars may be used in limited capacity to display patient medical data, no high-dimensionality precision virtual patient model system exists for integrated precision analytics and high-dimensionality virtual patient display.

Therefore, DICOM images, DICOM image based systems, and current avatar displays suffer from several disadvantages. The present disclosure provides solutions. For example, the present disclosure provides for the creation of a MIBA master file. The MIBA master file allows deployment of multiple new functionalities for clinical patient care. An encoding system is created which codes each individual voxel in a master file standardized volume with metadata including specific biomarker signature information generated in concert with big data population databases (such as early detection of cancer, tissue changes over time, and treatment effects), as well as data from annotations made by physicians and radiologists. Upon creation, the MIBA master file may be leveraged by multiple types of image processors and output interfaces, such as Query engines for data mining, database links for automatic uploads to pertinent big data databases, and output apps for output image viewing, information viewing, and annotation creation by radiologists, surgeons, interventionists, individual patients, and referring physicians.

New cloud-based systems will be a core for new informatics technology for seamless integration of massive datasets across large networks and deployment via a multitude of potential applications. In the future, by using MIBA master files, healthcare delivery systems will have the capacity to compare individual patient data to vast population databases at the speed of accumulation of new patient data. Patient care may be advanced by each patient having a transparent and holistic view of their entire medical status from full and complete proprietary datasets of their own records that are powered with informatics data. These new powerful systems form the basis for identification and use of a multitude of new imaging and other biomarkers, which will be the cornerstones for advancing patient care in a new era of precision medicine.

Turning now to FIG. 2, an example flowchart outlining a process 100 for creating and using a MIBA master file is shown, in accordance with some embodiments of the present disclosure. The process 100 provides an overview of various user interfaces used in the creation, storage, querying, and display of a MIBA master file. At operation 105, a MIBA system receives, from a user, a selection of a patient and a volume of interest (VOI) of the patient, for example "head." At operation 110, the MIBA system automatically selects or receives selection from the user of a matching (or substantially matching) virtual 3D patient model (referred to herein as "ref3D" (55)) from a population of previously compiled 3D patient models, which most closely resembles the patient (e.g., 35 yo female weighing 135 lbs, T1 type images). Alternately, if the patient has a prior MIBA file (155) of the matching volume of interest, it can be used instead of the ref3D. At operation 115, the MIBA system creates a MIBA master file for the patient based on the ref3D. Creation of the MIBA master file is discussed in greater detail below. Upon creation, the MIBA system stores the MIBA master file within database associated with the MIBA system and updates the MIBA master file, if necessary, at operations 120-135. Upon updating the MIBA master file (or if no updates are needed), the MIBA system makes the MIBA master file available to the user for querying (e.g., for extracting certain types of data or information) and the MIBA system may display the results on a display interface associated with the MIBA system at operation 140. As indicated at operation 145, the MIBA system may receive selection of additional new data from the user, and in response, the MIBA system may update the MIBA master file, as indicated as operations 120-135. At operation 120, a user decides whether to create updates to the created MIBA file. For example, a clinical Radiologist may place an annotation into the MIBA file stating that a lesion requires surveillance imaging in six months. At operation 125, the MIBA file is sent to storage. At operation 130, the MIBA file can be updated. For example, a patient returns for surveillance imaging of the prior annotated MIBA file. At operation 135, a user interface allows a user to allow the additional data to be added to the MIBA file, again starting at operation 105.

Figure 3:
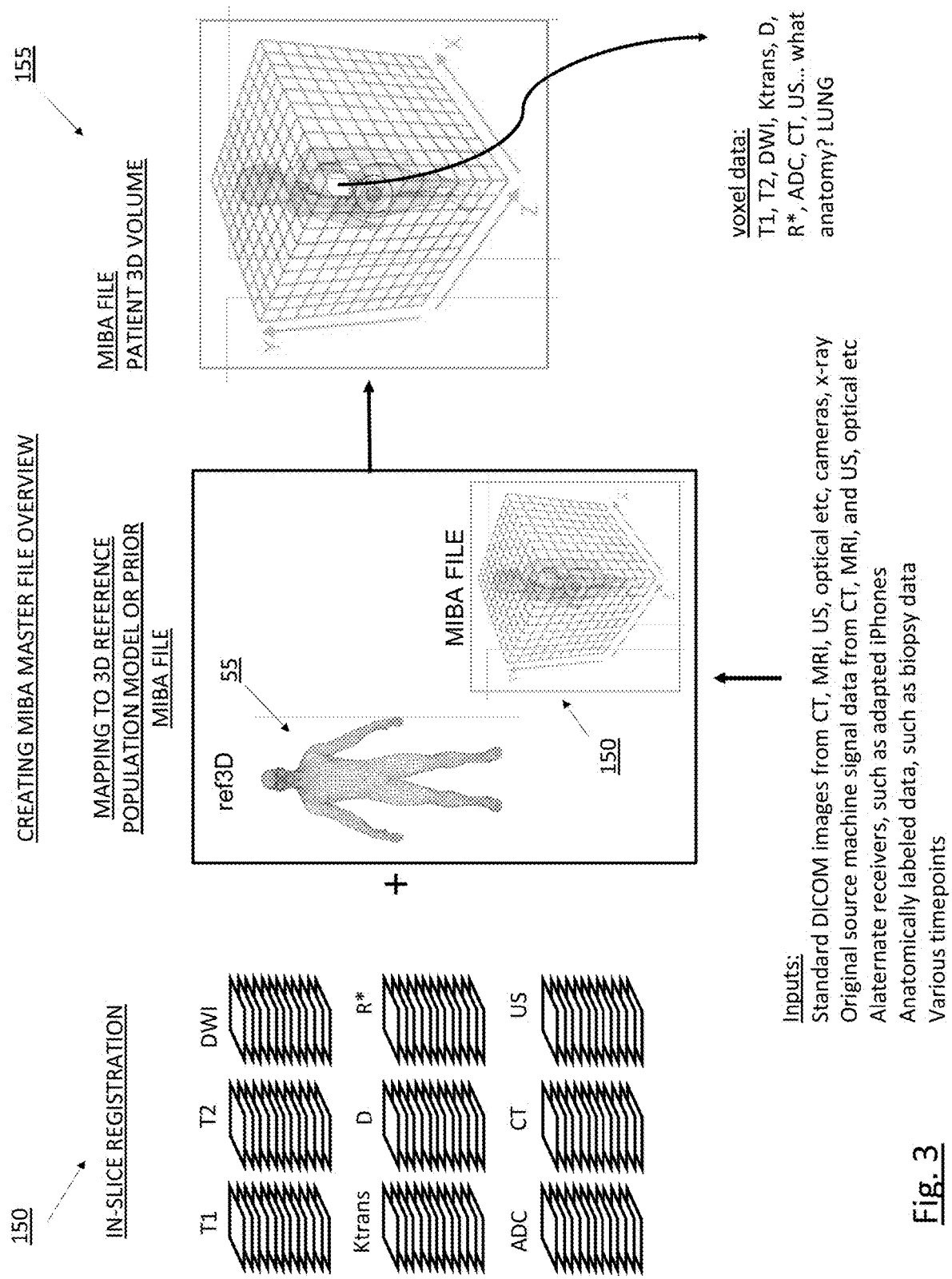
FIG. 3 illustrates an overview of creating the MIBA master file, in accordance with some embodiments of the present disclosure.

Referring now to FIG. 3, an overview diagram for creating a MIBA master file (also referred to herein as MIBA file, and the like) is shown, in accordance with some embodiments of the present disclosure. As indicated at 150, a multitude of stacks of patient image slices of various types of image modalities (Mill, CT, US, etc.), and various types of MRI sequences (T1, T2, DWI, etc.), are obtained. These patient image slices may be DICOM images or other types of medical images. The input image files are registered to a ref3D, as indicated via reference numeral 55, or alternately a prior matching MIBA file (150) if available. The registration may be rigid or non-rigid as needed for precision mapping but while maintaining anatomical correctness to the patient's true body proportions. As part of the registration, voxel values in the input image files are mapped to ref3D voxels or prior MIBA file. Biomarkers are also mapped to voxels either via encoding in the ref3D or prior MIBA file or via Moving Window Algorithms detailed below. In the example shown in FIG. 3, the voxel is identified as a voxel in the patient lung. The population ref3D can be made of any and all imaging modalities, and may contain metadata, including data on anatomical location.

Inputs to an anatomically organized MIBA file include standard DICOM images from CT, Mill, US, as well as any other file type such as tiff or jpeg files for optical cameras and other sources of images. These images can come from alternate sources other than machines directly, such as from iPhone interfaces.

FIGS. 4A and 4B are example flowcharts outlining a process 200 for forming a Medical Imaging Bioinformatics Annotated master file ("MIBA master file"). At operation 205, source images are obtained from a scanner (e.g., any type of medical imaging device, including imaging devices used for small animal studies (e.g., charts shown in FIGS. 30A-K)). The image data may be obtained from various imaging modalities such as magnetic resonance imaging (MRI), computed tomography (CT) imaging, positron emission tomography (PET) imaging, single-photon emission computed tomography (SPECT) imaging, micro-PET imaging, micro-SPECT imaging, Raman imaging, bioluminescence optical (BLO) imaging, ultrasound imaging, or any other suitable imaging technique. Further, when the imaging modalities includes Raman imaging, images may have a resolution of 25 nanometers or as desired, such that the created MIBA master file or a portion of it, has super high resolution on a nanometer scale allowing a user to "zoom in" to a very small structure. Standard post-processing may be used to generate parameter maps which are generated from simple image based calculations, such as ADC measures from multiple diffusion weighted images (DWI) or K trans measures from multiple images in dynamic contrast-enhanced MRI image sets. At operation 211, acquired images and maps are re-sliced in plane to match the x-y resolution of a reference standard 3D volume (ref3D). In-slice registrations are performed such that sets of images acquired during a single scanning session place each anatomical location in a matching position on each image in the image set. At operation 212, images obtained at multiple slice orientations are secondarily registered to a reference standard 3D volume (ref3D) or prior MIBA file of the specified body part, such as head, limb, or whole-body. A database to hold aggregate voxel data is started with standardized labels for each voxel in the ref3D or prior MIBA file at operation

225. Data is systematically entered into the database rows for each corresponding labelled voxel within that row with five general types of data: source values from source images, moving window (MW) data, MW classifier and parameter calculation output data, super-resolution (SR) solution output data, and annotation data. After all desired data is entered for each voxel in ref3D or prior MIBA file, data is compressed to eliminate unnecessary data, such as redundant normal tissue data. Further analytics and data compression can be performed before final MIBA file creation. After source data is entered at operation 225 to create the first data entry into the MIBA file (155), a volume of interest (VOI) is selected from the MIBA file dataset at operation 220 for further analytics to add biomarker information, either by user selection or computer software commands. As will be described in more detail, the further steps for adding biomarker data include defining moving windows (MW) at operation 230, applying MW at operation 231, creating 3D matrices at operation 232, refining 3D matrices at operation 233, applying matrix operations at operation 234, selecting user columns at operation 235, applying biomarker specific machine learning convolutional algorithm (MLCA) to create 2D matrices at operation 245, apply super-resolution algorithms to solve for each associated MIBA file output voxel value at operation 246, add annotations at operation 250, allow data compression at operation 251, storage of MIBA file at operation 125, versus further analytics at operation 255. Further analytics could include a multitude of possible algorithms in the future, but specifically can include adding new biomarker information at operation 260. If more biomarker data is to be added, the process repeats and loops back to operation 220. At various points along the process, voxelwise data can be added to the MIBA file in operation 240, as will be further described below.

Figure 5:
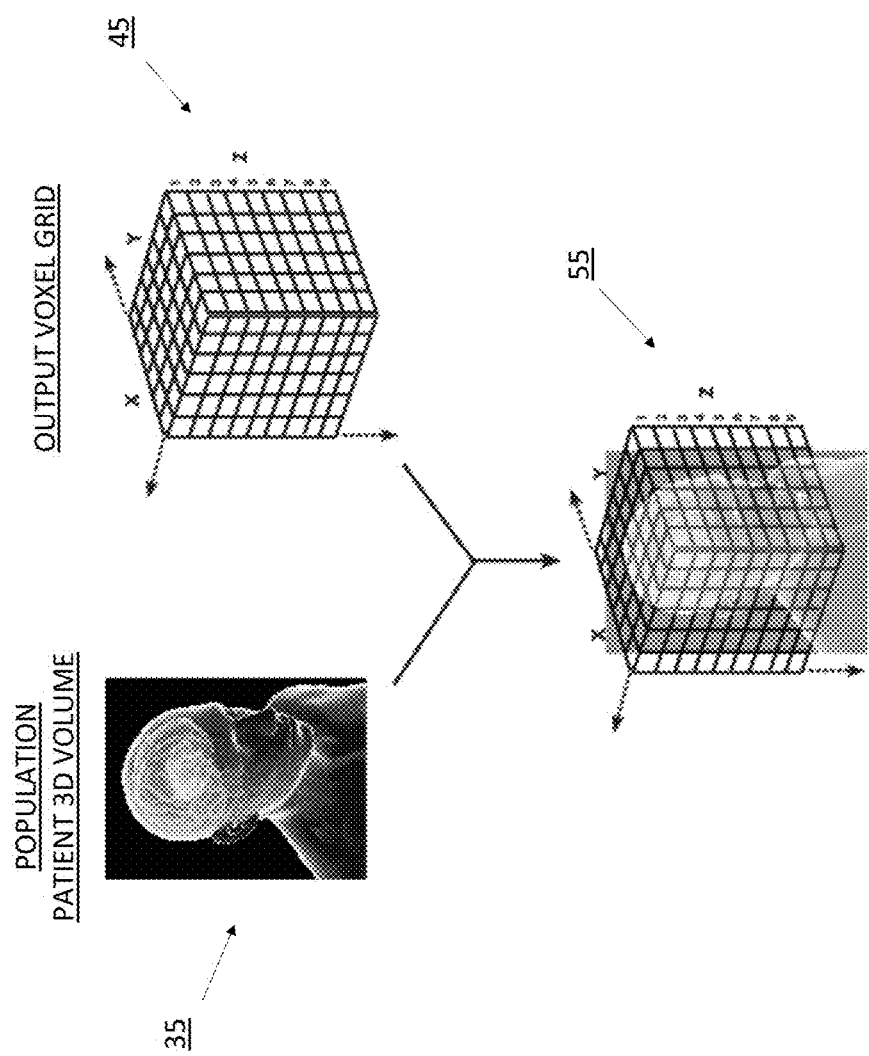
FIG. 5 illustrates selection of a 3D model for creating the MIBA master file, in accordance with some embodiments of the present disclosure.

FIG. 5 shows a schematic of the process for creating a reference 3D image volume 55, which is composed of a standard size high-resolution volume covering a reference patient anatomical volume 35 from a similar population as the patient (for example, man aged 50 years old, T1 type images). Any type of image modality or type or parameter maps may be used (e.g., see charts of FIGS. 30A-K) for obtaining the image volume 35. A 3D grid is selected with voxels of a desired resolution 45. FIG. 5 shows a sparse example with a total number of voxels of, for example, 324 voxels covering a reference head and neck of the image volume 35. It is to be noted that files may need to be much larger for clinical use. As an example, a 3D reference volume voxel grid resolution may be set at 0.5 mm×0.5 mm×0.5 mm, the X-Y-Z field of view (FOV) may be set at 30 cm×30 cm×30 cm for a total of 216,000,000 voxels when used for clinical purposes. A large population of ref3D may be required for inputs for the systems in order to obtain close matching with each individual patient and selected ref3D.

Figure 6:
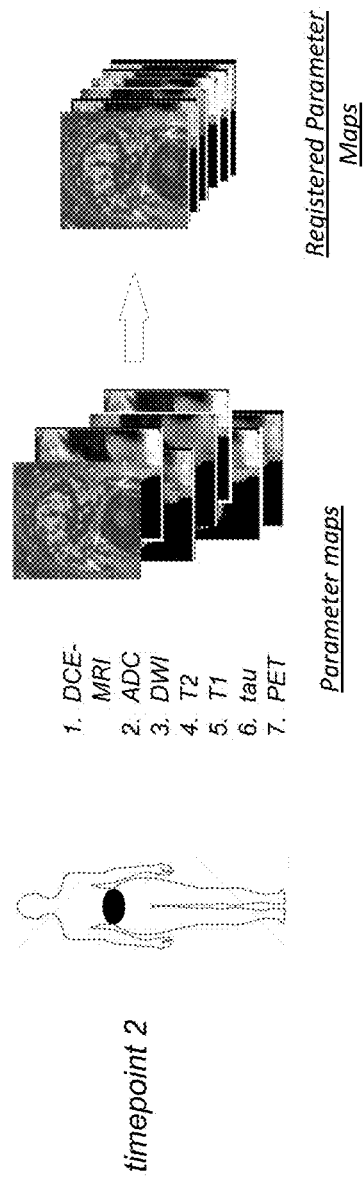
FIG. 6 illustrates an in-slice registration on image data for creating the MIBA master file, in accordance with some embodiments of the present disclosure.

Further, as indicated above, source images are registered in operation 211 to in-slice images obtained at the same timepoint on the same machine or on coordinated machines, such as registration of PET and CT on separate machines—as part of creating the MIBA master file. In some embodiments, as part of the registration, re-slicing of the images may be needed to obtain matching datasets with matching resolutions per modality across various time points. To facilitate more efficient image processing, such re-slicing may also be needed to align voxel boundaries when resolutions between modalities are different. As an example, FIG. 6 depicts registration of the image coordinates associated with the datasets of selected time point 2. Specifically, FIG. 6 illustrates a number of parameter maps for parameters associated with various imaging modalities (e.g., DCE-MRI, ADC, DWI, T2, T1, tau, and PET). The image coordinates for the various parameter maps are registered to enable the combined use of the various parameter maps in the creation of the MIBA master file. Registration may be performed using rigid marker based registration or any other suitable rigid or non-rigid registration technique. Example registration techniques may include B-Spline automatic registration, optimized automatic registration, Landmark least squares registration, midsagittal line alignment, or any other suitable registration technique.

Figure 7:
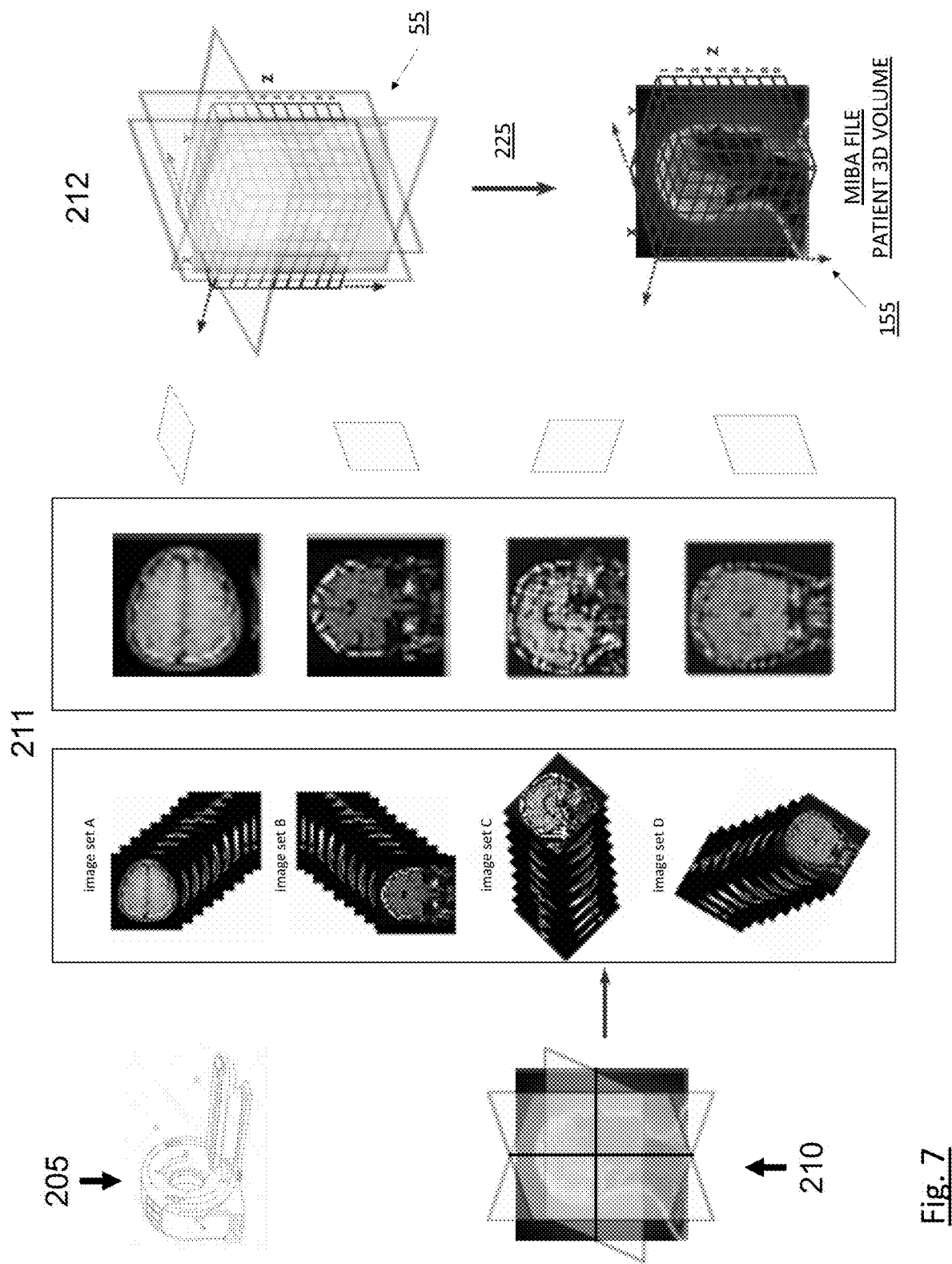
FIG. 7 illustrates a secondary registration on the in-sliced registered data for creating the MIBA master file, in accordance with some embodiments of the present disclosure.

FIG. 7 describes the secondary rigid registration of in-slice registered image sets 211 to a ref3D 55. The image sets may be acquired using a medical imaging scanner 205 at multiple slice angles to create a resultant patient specific volume MIBA file 155 with resolution matching the original ref3D volume. In this schematic example, four types of the image sets 211 (e.g., image sets A, B, C, D) after in-plane registration are shown, which are then registered to the ref3D volume using rigid registrations. For example, images from image set A are registered to ref3D volume 55 which may include the prior example image set of T1, T2, and DWI images. Similarly, images from the other image sets are registered to corresponding ref3D volumes. After registration of the image set A and entry of data at operation 255, the new registered pt3Dvol MIBA file 155 would contain source voxel data with matching resolution (for example, 0.5 mm×0.5 mm×0.5 mm) to the ref3D. This process would be repeated for each image set (B, C, D) to generate voxel metadata for the singular pt3Dvol MIBA file 155.

Although FIG. 7 shows a rigid registration mechanism, in some embodiments, it may be desirable to use a non-rigid registration technique. For example, a non-rigid registration technique may be used to map image slices from any orientation into a warped plane in an x-, y-, or z-plane.

Figure 8:
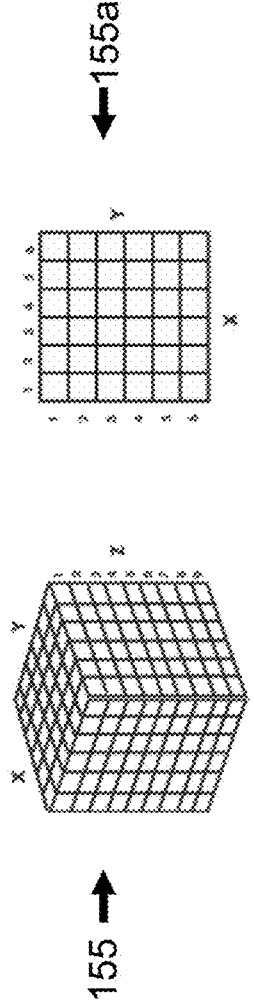
FIG. 8 illustrates extracting voxel data from the output of the secondary registration and entering into a MIBA database for creating the MIBA master file, in accordance with some embodiments of the present disclosure.

FIG. 8 displays how voxel source image data to the registered ref3D or prior MIBA file is entered into a MIBA file 155 associated with a MIBA creation system. The MIBA file can take the form of a 3D file 155, or organized in a spreadsheet format showing collated and coded data for each voxel in the MIBA file 155. An example spreadsheet format 225 of a portion of the MIBA database includes a variety of information pertaining to the registered image data. For example, the format 225 includes voxels labelled and organized by rows. For example, voxel code 1,1,1 is the voxel in the X=1, Y=1, and Z=1 position within the 3D volume. Voxel values are entered in locations where registration of source images led to a new registered voxel value in the registered MIBA file 3D volume. Column headings are entered as common data elements (CDE), such as those provided by the NIH (https://www.nlm.nih.gov/cde/summary\_table\_1.html) or other desired standard or created codes. In this example, a column header code for the source data from image acquisition A for T1 images is labelled, "A_SoD_T1" and voxel data is entered in corresponding voxels at the corresponding database location coded to the MIBA file 3D volume. It is to be understood that the format 225 is only an example. In other embodiments, additional, fewer, or different information may be included in the format 225.

Figure 9:
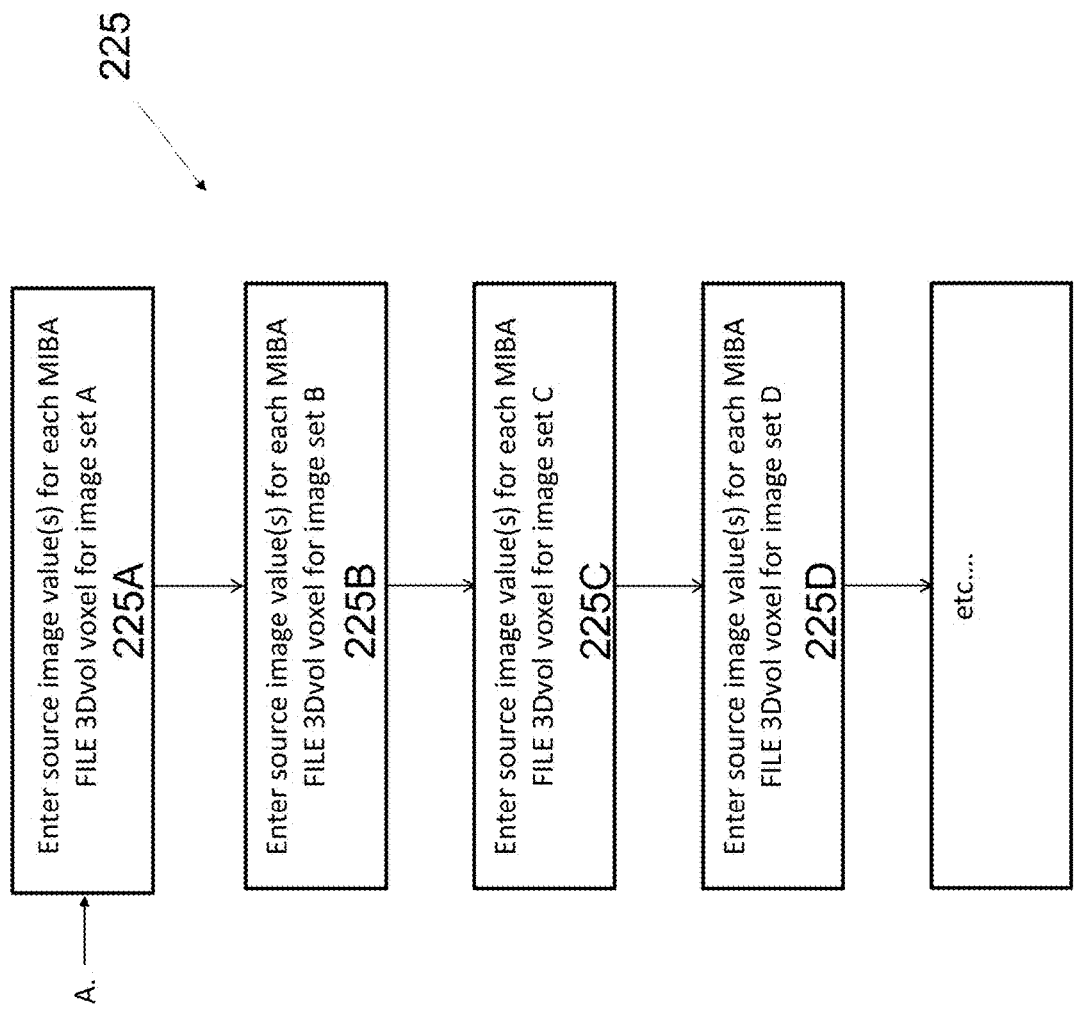
FIG. 9 is an example flowchart outlining operations for entering the voxel data in the MIBA database for creating the MIBA master file, in accordance with some embodiments of the present disclosure.

FIG. 9 shows a flowchart outlining a process 225 for source image voxel data entry for MIBA file 3D volume. Data entry into the MIBA spreadsheet database is similar for all potential image datasets registered to the ref3D or prior MIBA file. For example, for the image sets 211 (e.g., the image sets A, B, C, and D) of FIG. 7, information that is shown in the format 225 of FIG. 8 is extracted from each of the image sets and entered into the MIBA database. Thus, the MIBA database includes a compilation of data or records from the image sets 211 and each of the records may be in the format 225. In some embodiments, each of the records 225 in the MIBA database for the image sets 211 may have formats (e.g., the format 225) that are somewhat different. For example, based upon the information that is extracted from the image sets 211, the corresponding format 211 of those image sets may vary as well. Thus, as shown in the process 225, at operation 225A, a record for the image set A of the image sets 211 is created and added to the MIBA spreadsheet database, at operation 225B, a record for the image set B is created and added to the MIBA spreadsheet database, and at operations 225C and 225D, records for image sets C and Disclosure, respectively, are created and added to the MIBA spreadsheet database. Standard registration technique methods are used to determine the specific voxel values in the MIBA file grid from registered inputted data. FIG. 10 shows source data entry into the MIBA database as depicted in FIG. 9.

Referring back to FIG. 4A, after source data is entered into the MIBA file at operation 225, analytics steps are initiated. At operation 220, a Volume-of-Interest (VOI) is selected from the MIBA file either by user selection of image display or via a computer software algorithm. At operation 230, moving window (MW) algorithms are initiated.

For example, a slice of a MIBA file may be chosen and displayed in axial orientation, slice thickness of 1 mm, and in-plane resolution of 1 mm×1 mm. The source data is then chosen for display; example would include T1 values or parameter map values, such as K from DCE-MRI data. The Volume-of-Interest (VOI) for running MW algorithms is selected from the displayed images.

FIG. 10 provides an overview of MW matrix data entry into the MIBA spreadsheet file. Moving window parameters are chosen which include MW size, shape, point of origin, step size, and path. Selected MW is run across the images and a matrix of data is created. The process is repeated for each desired source data input and data is collated into the 3D matrix where each column holds data for matching MW coordinates and parameters for the various types of source data. For example, a single column of the 3D matrix may have data for the same MW including T1, T2, DWI, ADC, and K values at matching anatomical locations. The resultant MW 3D matrix file can be entered as an embedded metadata file into a selected corresponding cell of the MIBA spreadsheet database. Details are further described below.

Figure 11C:
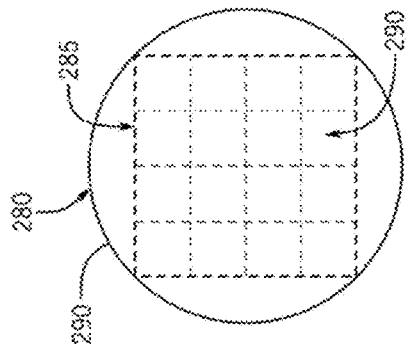
FIGS. 11A, 11B, and 11C depict example moving window configurations used for creating the MBA master file, in accordance with some embodiments of the present disclosure.
Figure 11B:
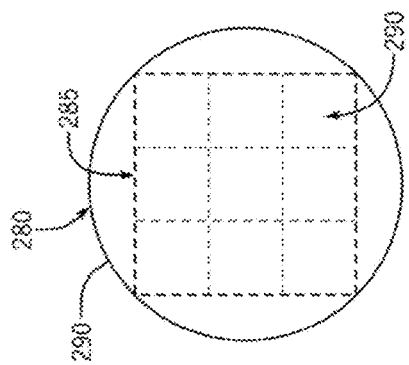
Figure 11A:
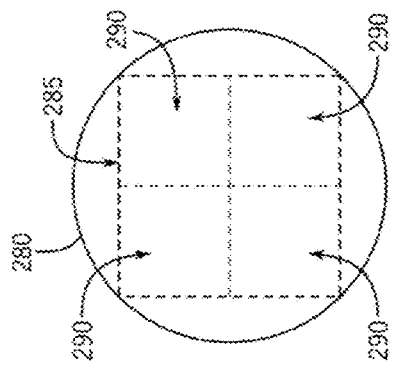

FIGS. 11A-11C show defining of a MW. Upon registration of the images, one or more moving windows are defined and the defined moving windows are used for analyzing the registered images. As used herein, a "moving window" is a "window" or "box" of a specific shape and size that is moved over the registered images in a series of steps or stops, and data within the "window" or "box" at each step is statistically summarized. The step size of the moving window may also vary. In some embodiments, the step size may be equal to the width of the moving window. In other embodiments, other step sizes may be used. Further, a direction in which the moving window moves over the data may vary from one embodiment to another. These aspects of the moving window are described in greater detail below.

The moving window is used to successively analyze discrete portions of each image within the selected image datasets to measure aspects of the selected parameters. For example, in some embodiments, the moving window may be used to successively analyze one or more voxels in the image data. In other embodiments, other features may be analyzed using the moving window. Based upon the features that are desired to be analyzed, the shape, size, step-size, and direction of the moving window may be varied. By changing one or more attributes (e.g., the shape, size, step size, and direction), multiple moving windows may be defined, and the data collected by each of the defined moving windows may be varied.

As an example and in some embodiments, the moving window may be defined to encompass any number or configuration of voxels at one time. Based upon the number and configuration of voxels that are to be analyzed at one time, the size, shape, step size, and direction of the moving window may be defined. Moving window volume may be selected to match the volumes of corresponding biomarker data within a volume-coded population database. Further, in some embodiments, the moving window may be divided into a grid having two or more adjacent subsections.

In some embodiments, the moving window may have a circular shape with a grid disposed therein defining a plurality of smaller squares. FIGS. 11A, 11B, and 11C depict various example moving window configurations having a circular shape with a square grid, in accordance with some embodiments. FIGS. 11A, 11B, and 11C each include a moving window 280 having a grid 285 and a plurality of square subsections 290. For example, FIG. 11A has four of the subsections 290, FIG. 11B has nine of the subsections, and FIG. 11C has sixteen of the subsections. It is to be understood that the configurations shown in FIGS. 11A, 11B, and 11C are only an example. In other embodiments, the moving window 280 may assume other shapes and sizes such as square, rectangular, triangle, hexagon, or any other suitable shape. Likewise, in other embodiments, the grid 285 and the subsections 290 may assume other shapes and sizes.

Thus, FIGS. 11A, 11B, and 11C shows various possible configurations where the moving window encompasses 4, 9, or 16 full voxels within the source images and a single moving window read measures the mean and variance of the 4, 9, and 12 voxels respectively. Further, the grid 285 and the subsections 290 need not always have the same shape. Additionally, while it may be desirable to have all of the subsections 290 be of the same (or similar) size, in some embodiments, one or more of the subsections may be of different shapes and sizes. In some embodiments, each moving window may include multiple grids, with each grid having one or more subsections, which may be configured as discussed above. In the embodiments of FIGS. 11A, 11B, and 11C, the shape and size of each of the subsections 290 may correspond to the shape and size of one MIBA master file output voxel in the MIBA file output voxel grid (defined as discussed above by the ref3D or prior MIBA file).

The step size of the moving window in the x, y, and z directions determines the output matrix dimensions in the x, y, and z directions, respectively. The specific shape(s), size(s), starting point(s), etc. of the applied moving windows determines the exact size of the matrix output grid. Furthermore, the moving window may be either two-dimensional or three-dimensional. The moving window 280 shown in FIGS. 11A, 11B, and 11C is two-dimensional. When the moving window 280 is three-dimensional, the moving window may assume three-dimensional shapes, such as a sphere, cube, etc.

Similarly, the size of the moving window 280 may vary from one embodiment to another. Generally speaking, the moving window 280 is configured to be no smaller than the size of the largest single input image voxel in the image dataset, such that the edges of the moving window encompass at least one complete voxel within its borders. Further, the size of the moving window 280 may depend upon the shape of the moving window. For example, for a circular moving window, the size of the moving window 280 may be defined in terms of radius, diameter, area, etc. Likewise, if the moving window 280 has a square or rectangular shape, the size of the moving window may be defined in terms of length and width, area, volume, etc.

Furthermore, a step size of the moving window 280 may also be defined. The step size defines how far the moving window 280 is moved across an image between measurements. In general, each of the subsections 290 corresponds to one source image voxel. Thus, if the moving window 280 is defined as having a step size of a half voxel, the moving window 280 is moved by a distance of one half of each of the subsections 290 in each step. The resulting matrix from a half voxel step size has a number of readings equal to the number of steps taken. Thus, based upon the desired specificity desired in the matrix data, the step size of the moving window 280 and the size and dimensions of each output matrix may be varied.

In addition, the step size of the moving window 280 determines a size (e.g., the number of columns, rows) of intermediary matrices into which the moving window output values are placed into the MBA master file, as described below. Thus, the size of the intermediary matrices may be determined before application of the moving window 280, and the moving window may be used to fill the intermediary matrices in any way based on any direction or random movement. Such a configuration allows for much greater flexibility in the application of the moving window 280.

Figure 12A:
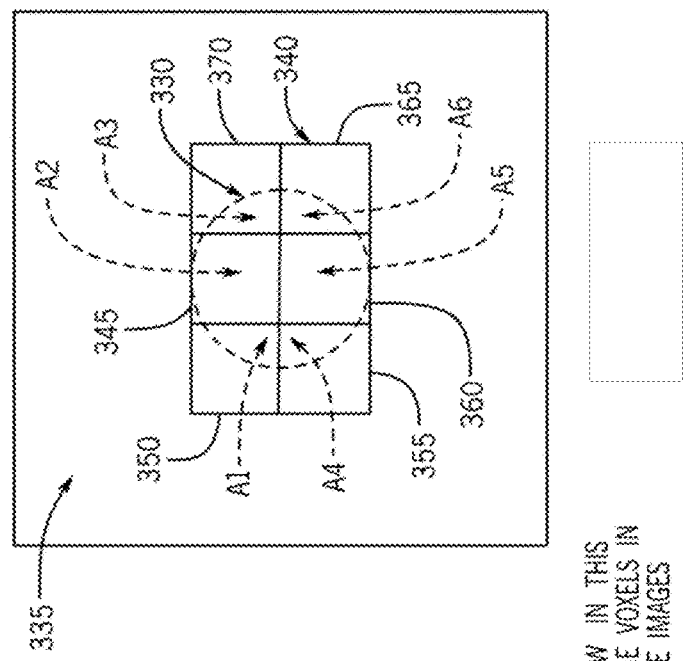
FIG. 12A is an example moving window and an output value defined within the moving window, in accordance with some embodiments of the present disclosure.
Figure 12B:
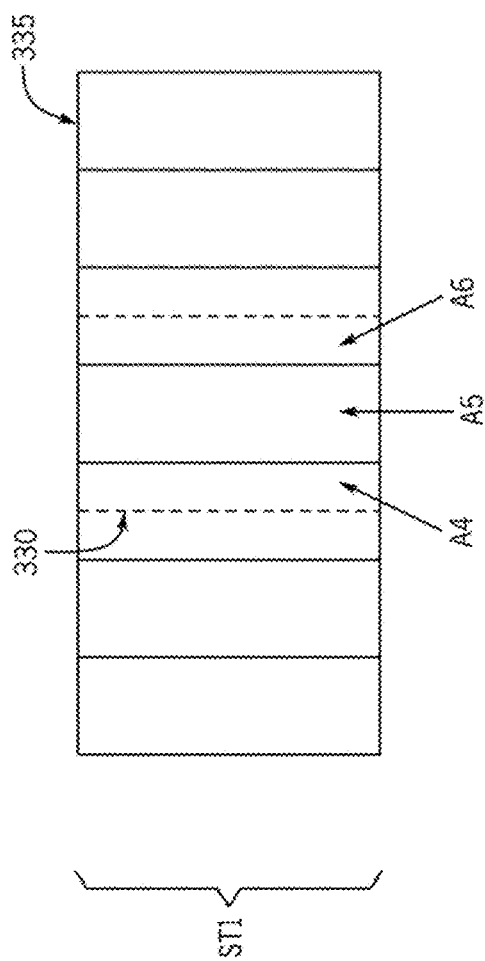
FIG. 12B is a cross-sectional view of the image from FIG. 11A in which the moving window has a cylindrical shape, in accordance with some embodiments of the present disclosure.
Figure 12C:
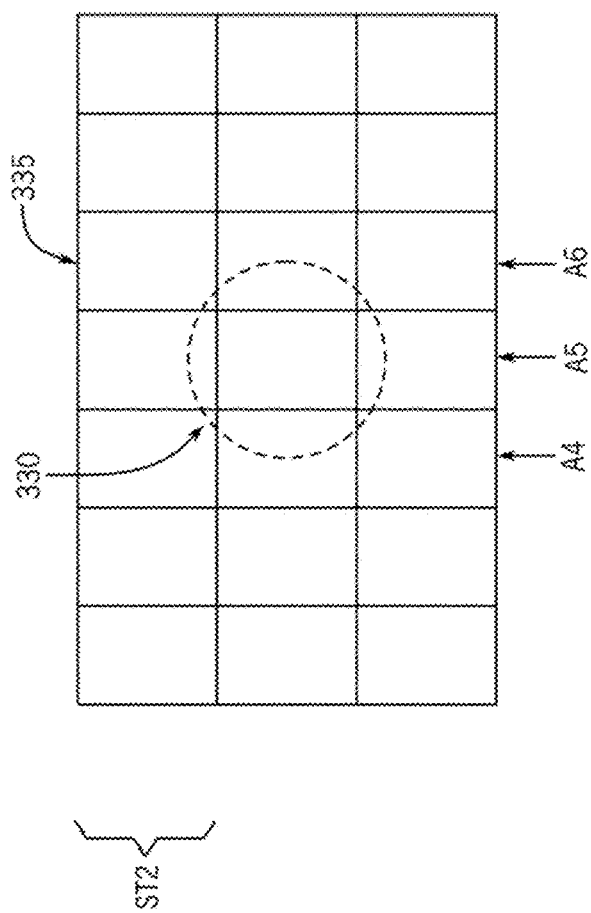
FIG. 12C is a cross-sectional view of the image of FIG. 11A in which the moving window has a spherical shape, in accordance with some embodiments of the present disclosure.

FIGS. 12A-12C show an example where the moving window read inputs all voxels fully or partially within the boundary of the moving window and calculates a read as the weighted average by volume with standard deviation. Specifically, FIG. 12A shows various examples of defining an output value within a moving window 330 in an image 335 at one step. As shown in 12A, the moving window 330 defines a grid 340 covering source image voxels and divided into multiple subsections 345, 350, 355, 360, 365, and 370. Further, as discussed above, each of the subsections 345-370 corresponds to one voxel in the source image. In some embodiments, the output value of the moving window 330 may be an average (or some other function) of those subsections 345-370 (or voxels) of the grid 340 that are fully or substantially fully encompassed within the moving window. For example, in FIG. 12A, the moving window 330 cuts off the subsections 350, 355, 365, and 370 such that only a portion of these subsections are contained within the moving window. In contrast, the subsections 345 and 360 are substantially fully contained within the moving window 330. Thus, the output value of the moving window 330 at the shown step may be the average of values in the subsections 345 and 360.

In other embodiments, a weighted average may be used to determine the output value of the moving window 330 at each step. When the values are weighted, the weight may be for percent area or volume of the subsection contained within the moving window 330. For example, in FIG. 12A, if a weighted average is used, the output value of the moving window 330 at the given step may be an average of all subsections 345-370 weighted for their respective areas A1, A2, A3, A4, A5, and A6 within the moving window. In some embodiments, the weighted average may include a Gaussian weighted average.

In other embodiments, other statistical functions may be used to compute the output value at each step of the moving window 330. Further, in some embodiments, the output value at each step may be adjusted to account for various factors, such as noise. Thus, the output value at each step may be an average value +/−noise. Noise may be undesirable readings from adjacent voxels. In some embodiments, the output value from each step may be a binary output value. For example, in those embodiments where a binary output value is used, the output probability value at each step may be a probability value of either 0 or 1, where 0 corresponds to a "yes" and 1 corresponds to a "no," or vice-versa based upon features meeting certain characteristics of any established biomarker. In this case, once 0 and 1 moving window probability reads are collated. Similarly, in the case where the convolution algorithm uses a parameter map function, such as pharmacokinetic equations, to output parameter measures, the values within the moving windows would be collated in lieu of probability values, but the same final output voxel solution may otherwise be implemented.

It is to be understood that the output values of the moving window 330 at each step may vary based upon the size and shape of the moving window. For example, FIG. 12B shows a cross-sectional view of the image 335 from FIG. 12A in which the moving window 330 has a cylindrical shape. FIG. 12C shows another cross-sectional view of the image 335 in which the moving window 330 has a spherical shape. In addition, the image 335 shown in FIG. 12B has a slice thickness, ST1, that is larger than a slice thickness, ST2, of the image shown in FIG. 12C. Specifically, the image of FIG. 12B is depicted as having only a single slice, and the image of FIG. 12C is depicted as having three slices. In the embodiment of FIG. 12C, the diameter of the spherically-shaped moving window 330 is at least as large as a width (or thickness) of the slice. Thus, the shape and size of the moving window 330 may vary with slice thickness as well.

Furthermore, variations in how the moving window 330 is defined are contemplated and considered within the scope of the present disclosure. For example, in some embodiments, the moving window 330 may be a combination of multiple different shapes and sizes of moving windows to better identify particular features of the image 335. Competing interests may call for using different sizes/shapes of the moving window 330. For example, due to the general shape of a spiculated tumor, a star-shaped moving window may be preferred, but circular or square-shaped moving windows may offer simplified processing. Larger moving windows also provide improved contrast to noise ratios and thus better detect small changes in tissue over time. Smaller moving windows may allow for improved edge detection in regions of heterogeneity of tissue components. Accordingly, a larger region of interest (and moving window) may be preferred for PET imaging, but a smaller region of interest (and moving window) may be preferred for CT imaging with highest resolutions. In addition, larger moving windows may be preferred for highly deformable tissues, tissues with motion artifacts, etc., such as liver. By using combinations of different shapes and sizes of moving windows, these competing interests may be accommodated, thereby reducing errors across time-points. In addition, different size and shaped moving windows (e.g., the moving window 330) also allow for size matching to data (e.g., biomarkers) within a precision database, e.g., where biopsy sizes may be different. Thus, based upon the features that are desired to be enhanced, the size and shape of the moving window 330 may be defined.

Further, in some embodiments, the size (e.g., dimensions, volume, area, etc.) and the shape of the moving window 330 may be defined in accordance with a data sample match from the precision database. Such a data sample match may include a biopsy sample or other confirmed test data for a specific tissue sample that is stored in a database. For example, the shape and volume of the moving window 330 may be defined so as to match the shape and volume of a specific biopsy sample for which one or more measured parameter values are known and have been stored in the precision database. Similarly, the shape and volume of the moving window 330 may be defined so as to match a region of interest (ROI) of tumor imaging data for a known tumor that has been stored in the precision database. In additional embodiments, the shape and volume of the moving window 330 may be chosen based on a small sample training set to create more robust images for more general pathology detection. In still further embodiments, the shape and volume of the moving window 330 may be chosen based on whole tumor pathology data and combined with biopsy data or other data associated with a volume of a portion of the tissue associated with the whole tumor.

Figure 13:
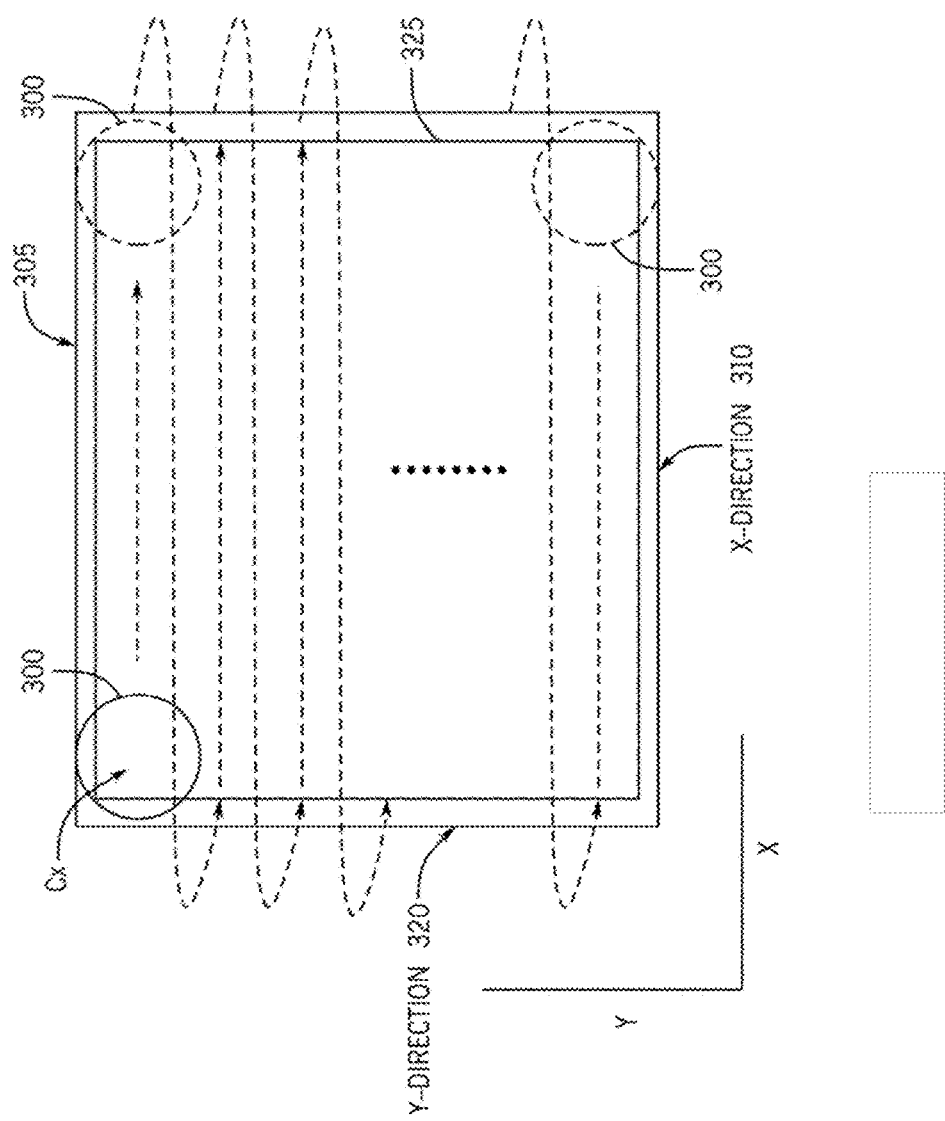
FIG. 13 is an example moving window and how the moving window is moved along x and y directions, in accordance with some embodiments of the present disclosure.

In addition to defining the size, shape, and step size of the moving window 280, the direction of the moving window may be defined. The direction of the moving window 280 indicates how the moving window moves through the various voxels of the image data. FIG. 15 depicts an example direction of movement of a moving window 300 in a region-of-interest 305 in an x direction 310 and a y direction 320, in accordance with an illustrative embodiment. As shown in FIG. 13, the movement direction of the moving window 300 is defined such that the moving window is configured to move across a computation region 325 of the image 305 at regular step sizes or intervals of a fixed distance in the x direction 310 and the y direction 320. Specifically, the moving window 300 may be configured to move along a row in the x direction 310 until reaching an end of the row. Upon reaching the end of the row, the moving window 300 moves down a row in the y direction 320 and then proceeds across the row in the x direction 310 until again reaching the end of the row. This pattern is repeated until the moving window 300 reaches the end of the image 305. In other embodiments, the moving window 300 may be configured to move in different directions. For example, the moving window 300 may be configured to move first down a row the y direction 320 until reaching then end of the row and then proceed to a next row in the x direction 310 before repeating its movement down this next row in the y direction. In another alternative embodiment, the moving window 300 may be configured to move randomly throughout the computation region 325.

Further, as noted above, the step size of the moving window 300 may be a fixed (e.g., regular) distance. In some embodiments, the fixed distance in the x direction 310 and the y direction 320 may be substantially equal to a width of a subsection of the grid (not shown in FIG. 13) of the moving window 300. In other embodiments, the step size may vary in either or both the x direction 310 and the y direction 320.

Additionally, each movement of the moving window 300 by the step size corresponds to one step or stop. At each step, the moving window 300 measures certain data values (also referred to as output values). For example, in some embodiments, the moving window 300 may measure specific MRI parameters at each step. The measured data values may be measured in any of variety of ways. For example, in some embodiments, the data values may be mean values, while in other embodiments, the data values may be a weighted mean value of the data within the moving window 300. In other embodiments, other statistical analysis methods may be used for the data within the moving window 300 at each step.

The moving window, upon defining, is applied at operation 231 of FIG. 4B. Specifically, the defined moving window (e.g., the moving window 330) is applied to a computation region (e.g., the computation region 325) of each image (e.g., the image 335) within each of the selected image datasets such that an output value and variance (such as a standard deviation) is determined for each image at each step of the moving window in the computation region. Each output value is recorded and associated with a specific coordinate on the corresponding computation region of the image. In some embodiments, the coordinate is an x-y coordinate. In other embodiments, y-z, x-z, or a three dimensional coordinate may be used. By collecting the output values from the computation region (e.g., the computation region 325), a matrix of moving window output values is created and associated with respective coordinates of the analyzed image (e.g., the image 335).

In some cases, the moving window reading may obtain source data from the imaging equipment prior to reconstruction. For example, magnetic resonance fingerprinting source signal data is reconstructed from a magnetic resonance fingerprinting library to reconstruct standard images, such as T1 and T2 images. Source MR Fingerprinting, other magnetic resonance original signal data or data from other machines, may be obtained directly and compared to the volume-coded population database in order to similarly develop a MLCA to identify biomarkers from the original source signal data.

More specifically, in some embodiments, the operation 231 of FIG. 4B involves moving the moving window 330 across the computation region 325 of the image 335 at the defined step sizes and measuring the output value of the selected matching parameters at each step of the moving window. It is to be understood that same or similar parameters of the moving window are used for each image (e.g., the image 335) and each of the selected image datasets. Further, at each step, an area of the computation region 325 encompassed by the moving window 330 may overlap with at least a portion of an area of the computation region encompassed at another step. Further, where image slices are involved and the moving window 330 is moved across an image (e.g., the image 335) corresponding to an MRI slice, the moving window is moved within only a single slice plane until each region of the slice plane is measured. In this way, the moving window is moved within the single slice plane without jumping between different slice planes.

The output values of the moving window 330 from the various steps are aggregated into a 3D matrix according to the x-y-z coordinates associated with each respective moving window output value. In some embodiments, the x-y coordinates associated with each output value of the moving window 330 correspond to the x-y coordinate on a 2D slice of the original image (e.g., the image 335), and various images and parameter map data is aggregated along the z-axis (e.g., as shown in FIG. 7).

Figure 14B:
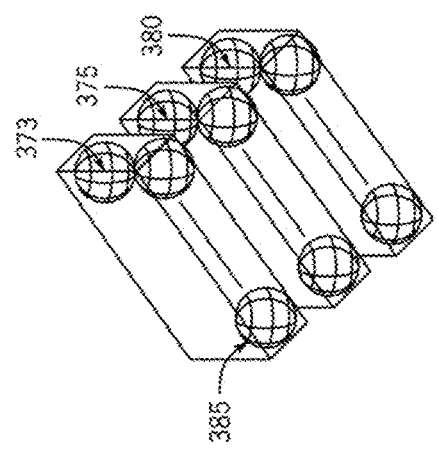
FIG. 14B is an end view of multiple slice planes and their corresponding moving windows, in accordance with some embodiments of the present disclosure.
Figure 14A:
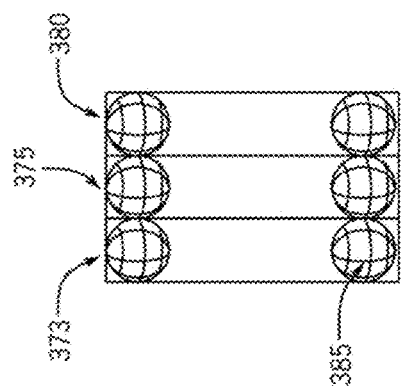
FIG. 14A is a perspective view of multiple slice planes and moving windows in those slice planes, in accordance with some embodiments of the present disclosure.

FIG. 14A depicts a perspective view of multiple 2D slice planes 373, 375, and 380 in accordance with an illustrative embodiment. A spherical moving window 385 is moved within each respective slice planes 373, 375, and 380. FIG. 14B depicts an end view of slice planes 373, 375, and 380. Again, the spherical moving window 385 is moved within the respective slice planes 373, 375, and 380 but without moving across the different slice planes. In this way, moving window values may be created and put into a matrix associated with a specific MRI slice and values between different MRI slices do not become confused (e.g., the moving window moving within the slices for each corresponding image and parameter map in the dataset).

Figure 14C:
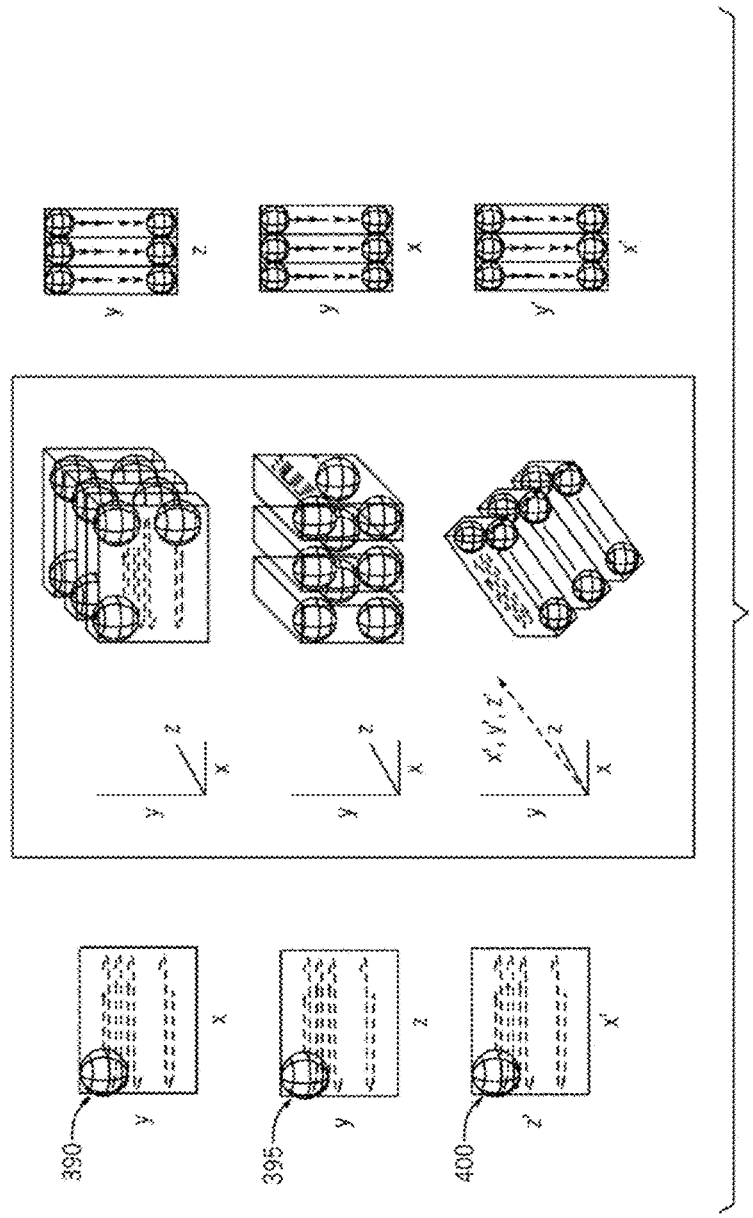
FIG. 14C is an example in which image slices for the sample are taken at multiple different angles, in accordance with some embodiments of the present disclosure.

FIG. 14C depicts an embodiment in which MRI imaging slices for a given tissue sample are taken at multiple different angles. The different angled imaging slices may be analyzed using a moving window (e.g., the moving window 385) and corresponding matrices of the moving window output values may be independently entered into the MIBA file. The use of multiple imaging slices having different angled slice planes allows for improved sub-voxel characterization, better resolution in the output image, reduced partial volume errors, and better edge detection. For example, slice 390 extends along the y-x plane and the moving window 385 moves within the slice plane along the y-x plane. Slice 395 extends along the y-z plane and the moving window 385 moves within the slice plane along the y-z plane. Slice 400 extends along the z'-x' plane and the moving window 385 moves within the slice plane along the z'-x' plane. Movement of the moving window 385 along all chosen slice planes preferably has a common step size to facilitate comparison of the various moving window output values. When combined, the slices 390-400 provide image slices extending at three different angles.

Figure 14D:
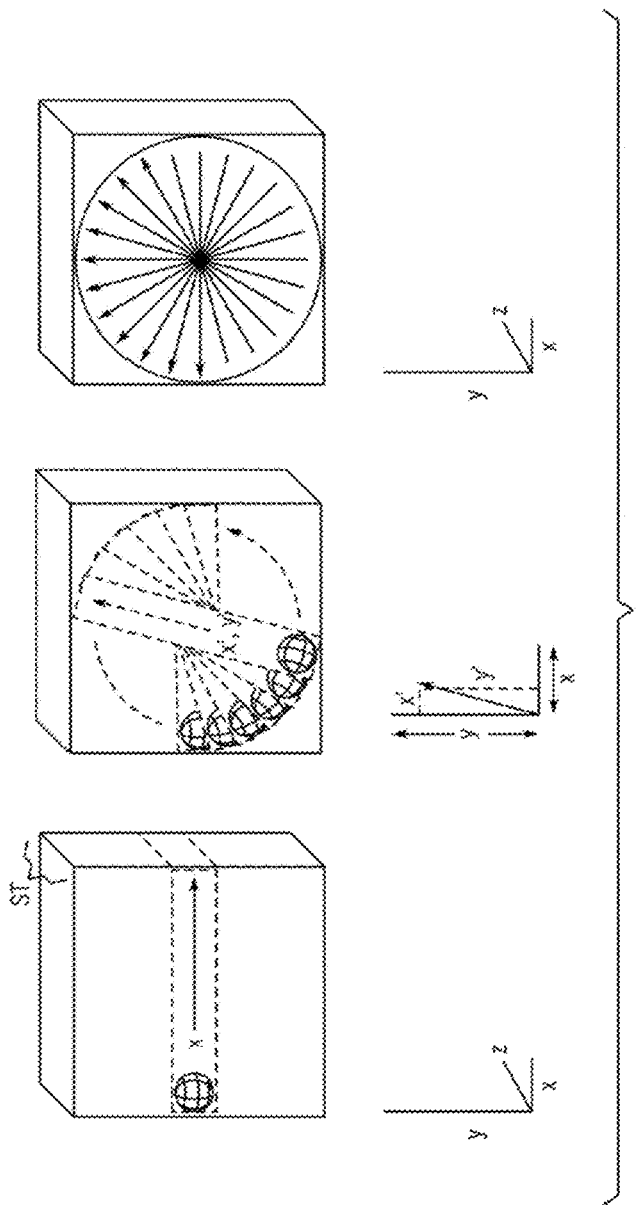
FIG. 14D is an example in which the image slices are taken at additional multiple different angles in a radial pattern, in accordance with some embodiments of the present disclosure.

FIG. 14D depicts an additional embodiment in which MRI imaging slices for a given tissue sample are taken at additional multiple different angles. In the embodiment of FIG. 14D, multiple imaging slices are taken at different angles radially about an axis in the z-plane. In other words, the image slice plane is rotated about an axis in the z-plane to obtain a large number of image slices. Each image slice has a different angle rotated slightly from an adjusted image slice angle.

Figure 15A:
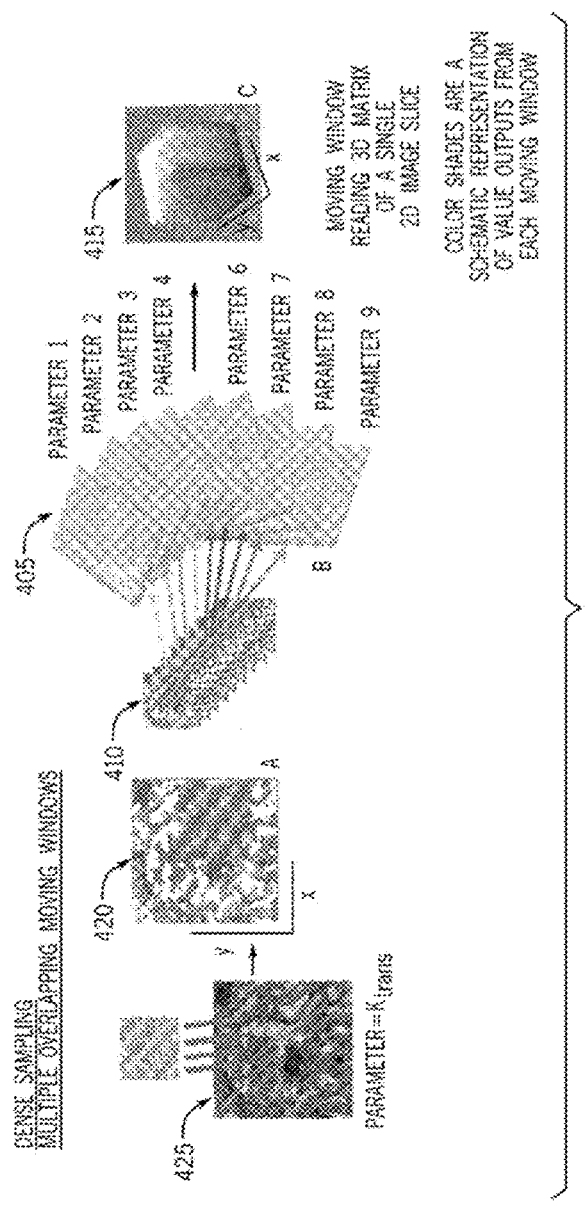
FIG. 15A shows assembling multiple two-dimensional ("2D") image slices into a 3D matrix, in accordance with some embodiments of the present disclosure.

Further, in some embodiments, moving window data for 2D slices is collated with all selected parameter maps and images registered to the 2D slice that are stacked to form the 3D matrix. FIG. 15A shows an example assembly of moving window output values 405 for a single 2D slice 410 being transformed into a 3D matrix 415 containing data across nine parameter maps, with parameter data aligned along the z-axis. Specifically, dense sampling using multiple overlapping moving windows may be used to create a 3D array of parameter measures (e.g., the moving window output values 405) from a 2D slice 425 of a human, animal, etc. Sampling is used to generate a two-dimensional (2D) matrix for each parameter map, represented by the moving window output values 405. The 2D matrices for each parameter map are assembled to form the multi-parameter 3D matrix 415, also referred to herein as a data array. In some embodiments, the 3D matrix 415 may be created for each individual slice of the 2D slice 425 by aggregating moving window output values for the individual slice for each of a plurality of parameters. According to such an embodiment, each layer of the 3D matrix 415 may correspond to a 2D matrix created for a specific parameter as applied to the specific individual slice.

The parameter set (e.g., the moving window output values 405) for each step of a moving window (e.g., the moving window 385) may include measures for some specific selected matching parameters (e.g., T1 mapping, T2 mapping, delta Ktrans, tau, Dt IVIM, fp IVIM, and R*), values of average Ktrans (obtained by averaging Ktrans from TM, Ktrans from ETM, and Ktrans from SSM), and average Ve (obtained by averaging Ve from TM and Ve from SSM). Datasets may also include source data, such as a series of T1 images during contrast injection, such as for Dynamic Contrast Enhanced MRI (DCE-MRI). In an embodiment, T2 raw signal, ADC (high b-values), high b-values, and nADC may be excluded from the parameter set because these parameters are not determined to be conditionally independent. In contrast, T1 mapping, T2 mapping, delta Ktrans, tau, Dt IVIM, fp IVIM, and R* parameters may be included in the parameter set because these parameters are determined to be conditionally independent. Further, a 3D matrix (e.g., the 3D matrix 415) is created for each image in each image dataset.

Figure 15B:
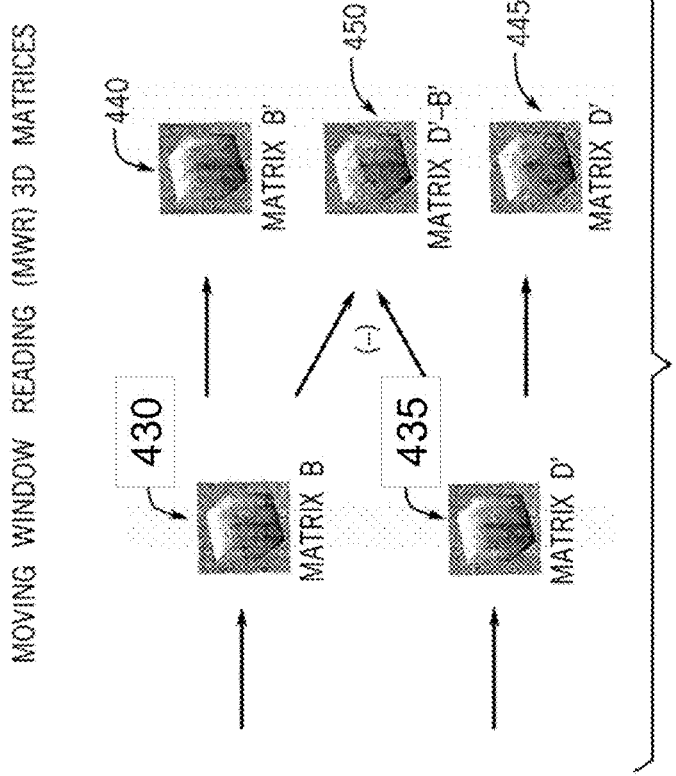
FIG. 15B shows an example matrix operation applied to 3D matrices, in accordance with some embodiments of the present disclosure.

Returning back to FIGS. 4A and 4B, the 3D matrices are refined at an operation 233. Refining a 3D matrix may include dimensionality reduction, aggregation, and/or subset selection processes. Other types of refinement operations may also be applied to each of the 3D matrices obtained at the operation 233. Further, in some embodiments, the same refinement operation may be applied to each of the 3D matrices, although in other embodiments, different refinement operations may be applied to different 3D matrices as well. Refining the 3D matrices may reduce parameter noise, create new parameters, and assure conditional independence needed for future classifications. As an example, FIG. 15B shows the 3D matrices 430 and 435 being refined into matrices 440 and 445, respectively. The matrices 440 and 445, which are refined, are also 3D matrices.

On the refined matrices (e.g., the matrices 440 and 445), one or more matrix operations are applied at operation 234 of FIG. 4B. The matrix operations generate a population of matrices for use in analyzing the sample. FIG. 15B shows an example of a matrix operation being applied to the matrices 440 and 445, in accordance with some embodiments of the present disclosure. Specifically, a matrix subtraction operation is applied on the matrices 440 and 445 to obtain a matrix 450. By performing the matrix subtraction, a difference in parameter values across all parameter maps at each stop of the moving window (e.g., the moving window 385) from each of the matrices 440 and 445 may be obtained. In other embodiments, other matrix operations may be performed on the matrices 440 and 445 as well. For example, in some embodiments, matrix operations may include matrix addition, subtraction, multiplication, division, exponentiation, transposition, or any other suitable and useful matrix operation. Various matrix operations may be selected as needed for later advanced big data analytics. Further, such matrix operations may be used in a specific Bayesian belief network to define a specific biomarker that may help answer a question regarding the tissue being analyzed, e.g., "Did the tumor respond to treatment?"

Figure 16:
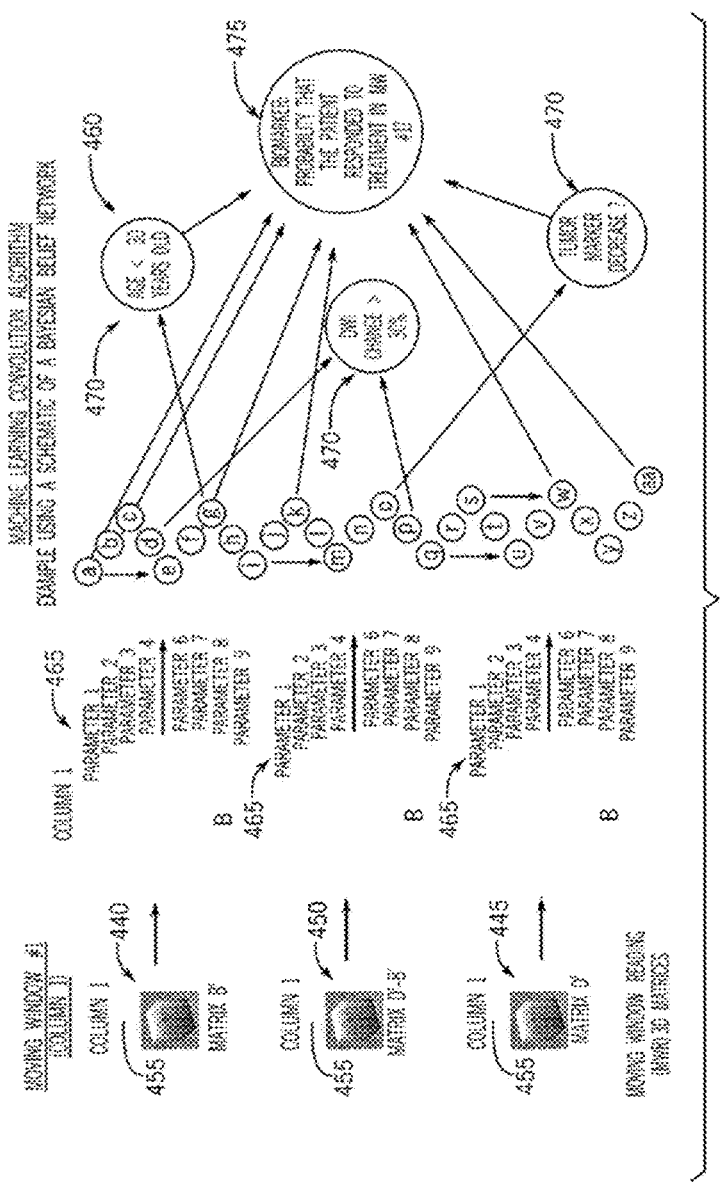
FIG. 16 shows selecting corresponding matrix columns from various 3D matrices and applying the MLCA on the matrix columns, in accordance with some embodiments of the present disclosure.

Columns from each 3D matrix (e.g., the matrices 440, 445, and 450) are selected for comparison and analysis 235 in FIG. 4. In this way, subsets of the various matrices (e.g., the matrices 440, 445, and 450) that correspond to the same small areas of the tissue sample may be compared and analyzed. FIG. 16 shows the selection of a corresponding matrix column 455 in the matrices 440-450. As shown, the matrix column 455 that is selected corresponds to the first column (e.g., Column 1) of each of the matrices 440-450. The matrix column 455 in each of the matrices 440-450 corresponds to the same small area of the sample. It is to be understood that the selection of Column 1 as the matrix column 455 is only an example. In other embodiments, depending upon the area of the sample desired to be analyzed, other columns from each of the matrices 440-450 may be selected. Additionally, in some embodiments, multiple columns from each of the matrices 440-450 may be selected to analyze and compare multiple areas of the sample. When multiple column selections are used, in some embodiments, all of the desired columns may be selected simultaneously and analyzed together as a group. In other embodiments, when multiple column selections are made, columns may be selected one at a time such that each selected column (e.g., the matrix column 455) is analyzed before selecting the next column.

Figure 15C:
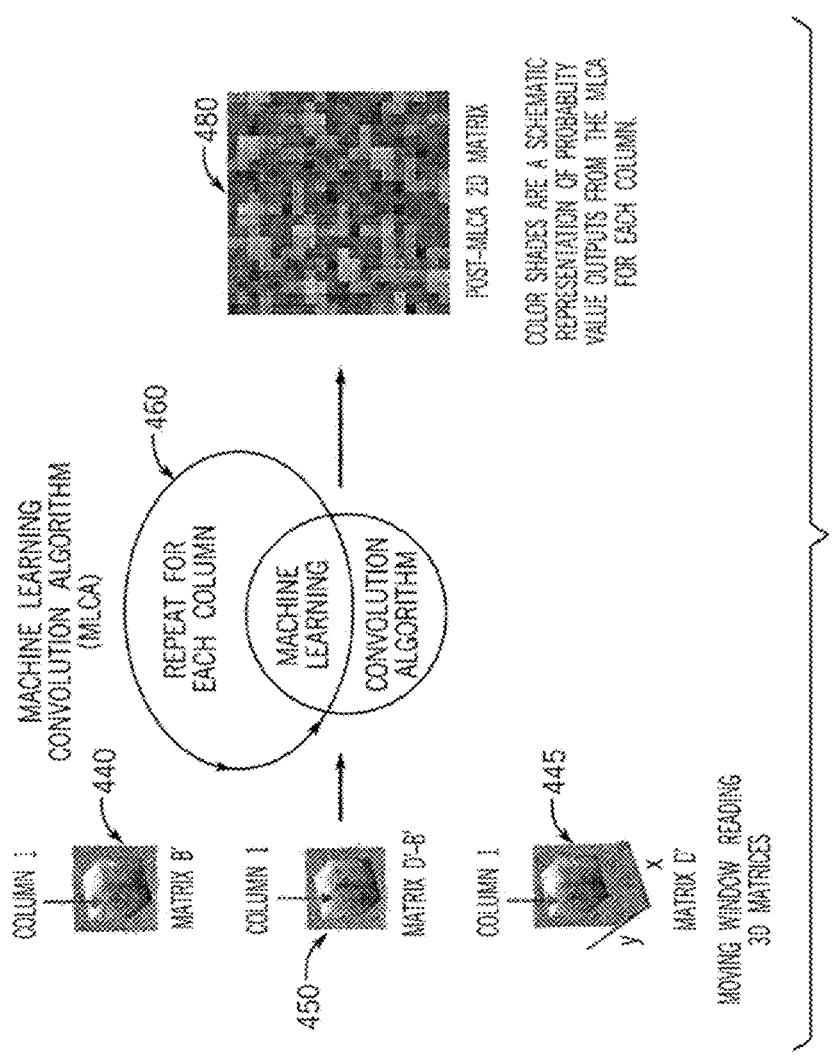
FIG. 15C shows a 2D matrix obtained by applying a machine learning convolution algorithm ("MLCA") to a 3D matrix, in accordance with some embodiments of the present disclosure.

The matrix columns selected at the operation 245 of FIGS. 4A and 4B are subject to a machine learning convolution algorithm ("MLCA") and a 2D Matrix (also referred to herein as a convoluted graph) is output from the MLCA. In some embodiments and as shown in FIGS. 15C and 16A, the MLCA 460 may be a Bayesian belief network that is applied to the selected columns (e.g., the matrix column 455) of the matrices 440-450. The Bayesian belief network is a probabilistic model that represents probabilistic relationships between the selected columns of the matrices 440-450 having various parameter measures or maps 465. The Bayesian belief network also takes into account several other pieces of information, such as clinical data 470. The clinical data 470 may be obtained from patient's medical records and matching data in the precision database and/or the volume-coded precision database are used as training datasets. Further, depending upon the embodiment, the clinical data 470 may correspond to the patient whose sample (e.g., the sample 170) is being analyzed, the clinical data of other similar patients, or a combination of both. Also, the clinical data 470 that is used may be selected based upon a variety of factors that may be deemed relevant. The Bayesian belief network combines the information from the parameter measures or maps 465 with the clinical data 470 in a variety of probabilistic relationships to provide a biomarker probability 475. Thus, the biomarker probability 475 is determined from the MLCA which inputs the parameter value data (e.g., the parameter measures or maps 465) and other desired imaging data in the dataset within each selected column (e.g., the matrix column 455) of the matrices 440-1220, the weighting determined by the Bayesian belief network, and determines the output probability based on the analysis of training datasets (e.g., matching imaging and the clinical data 470) stored in the precision database.

Thus, by varying the selection of the columns (e.g., the matrix column 455) providing varying imaging measures and using a biomarker specific MLCA (with the same corresponding clinical data 470), the biomarker probability 475 varies across moving window reads. The biomarker probability 475 may provide an answer to a clinical question. A biomarker probability (e.g., the biomarker probability 475) is determined for each (or some) column(s) of the matrices 440-450, which are then combined to produce a 2D matrix. As an example, FIG. 15C shows a 2D matrix 480 produced by applying the MLCA 460 to the matrices 440-450. Similar to the biomarker probability 475, the 2D Matrix 480 corresponds to a biomarker probability and answers a specific clinical question regarding the sample 165. For example, the 2D matrix 480 may answer clinical questions such as "Is cancer present?," "Do tissue changes after treatment correlate to expression of a given biomarker?," "Did the tumor respond to treatment?," or any other desired questions. The 2D matrix 480, thus, corresponds to a probability density function for a particular biomarker. Therefore, biomarker probabilities (e.g., the biomarker probability 475) determined from the matrices 440-450 are combined to produce the 2D matrix 480, represented by a probability density function.

Although Bayesian belief network has been used as the MLCA 460 in the present embodiment, in other embodiments, other types of MLCA such as a convolutional neural network or other classifiers or machine learning algorithms may be used instead or in addition to the Bayesian belief network. In addition to answering certain clinical questions, the 2D matrix 480 may be viewed directly or converted to a 3D graph for viewing by an interpreting physician to gain an overview of the biomarker probability data. For example, the 2D matrix 480 may be reviewed by a radiologist, oncologist, computer program, or other qualified reviewer to identify unhelpful data prior to completion of full image reconstruction, as detailed below. If the 2D matrix 480 provides no or vague indication of large enough probabilities to support a meaningful image reconstruction or biomarker determination, the image data analysis (e.g., the 2D matrix 480) may be discarded.

Alternatively or additionally, modifications may be made to the image data analysis parameters (e.g., modifications in the selected columns of the matrices 440-1220, the clinical data 470, etc.) and the MLCA 460 may be reapplied and another 2D matrix obtained. In some embodiments, the moving window size, shape, and/or other parameter may be modified and operations of FIGS. 4A and 4B re-applied. By redefining the moving window, different 2D matrices (e.g., the 2D matrix 480) may be obtained. An example collection of data from moving windows of different shapes and sizes is shown in FIG. 17. Specifically, FIG. 17 shows a collection of data using a circular moving window 485, a square moving window 490, and a triangular moving window 495. From each of the moving windows 485-495, a corresponding 3D matrix 500-510 is obtained. On each of the 3D matrix 500-510, MLCA is applied to obtain a respective 2D matrix 515-525. Thus, by refining the moving window, multiple 2D matrices (e.g., the 2D matrices 515-525) may be created for a particular region of interest. Although FIG. 17 shows variation in the shape of the moving window, in other embodiments, other aspects, such as size, step size, and direction may additionally or alternatively be varied to obtain each of the 2D matrix 515-525. Likewise, in some embodiments, different angled slice planes may be used to produce the different instances of the 2D matrix 515-525. The data collected from each moving window in the 2D matrix 515-525 is entered into first and second matrices and is combined into a combined matrix using a matrix addition operation, as discussed below.

Additionally, in some embodiments, different convolution algorithms may be used to produce parameter maps and/or parameter change maps. For example, a 2D matrix map may be created from a 3D matrix input using such a convolution algorithm. Examples of such convolution algorithms may include pharmacokinetic equations for Ktrans maps or signal decay slope analysis used to calculated various diffusion-weighted imaging calculations, such as ADC. Such algorithms may be particularly useful in creating final images with parameter values instead of probability values.

Figure 18A:
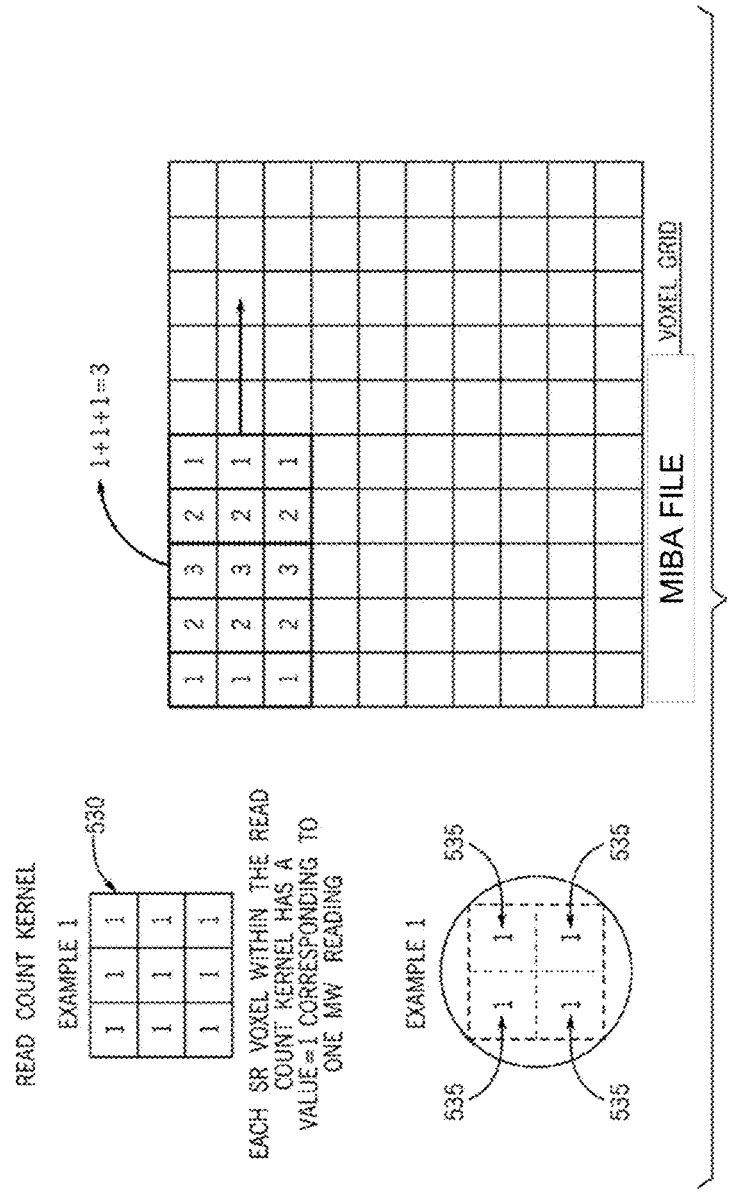
FIG. 18A shows an example "read count kernel" for determining a number of moving window reads per voxel, in accordance with some embodiments of the present disclosure.
Figure 18B:
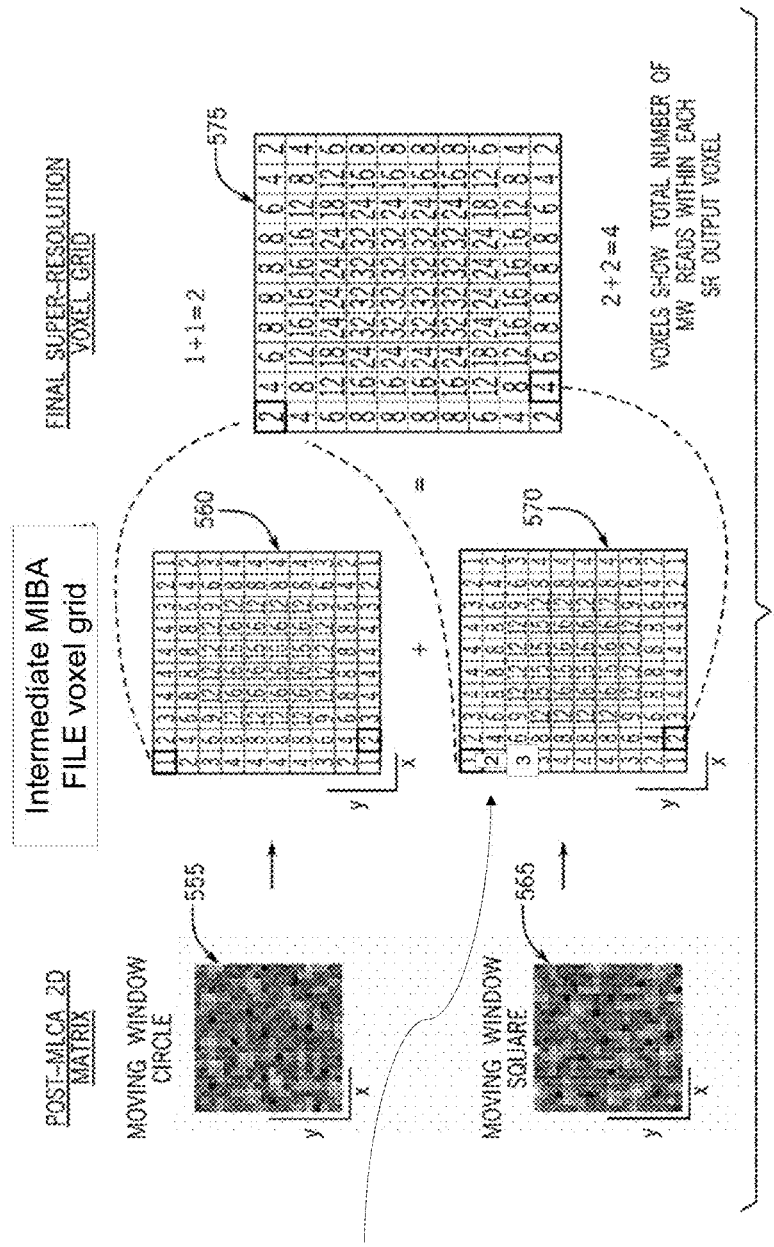
FIG. 18B shows a reconstruction example in which a 2D final voxel grid is produced from various intermediate 2D matrices, in accordance with some embodiments of the present disclosure.

Referring still to FIGS. 4A and 4B, at operation 246, a super-resolution reconstruction algorithm is applied to the 2D matrix (e.g., the 2D matrix 480 and/or the 2D matrices 515-525) to produce an output solution value at a defined voxel within the MIBA file for each desired biomarker and for the specific case in which voxels within the MW (290 in FIG. 11A-C) correspond to the size and shape of the MIBA file output voxel. In this case, multiple MW reads will be available in the MIBA file for a given voxel for a specific biomarker, and the size and shape of the voxel in the MIBA file will meet the criteria described in FIG. 11A-C 290. Specifically, the super-resolution algorithm produces a final super-resolution voxel output value from a combination of the 2D matrices 555-565, as depicted in FIGS. 18A and 18B, which provide the multiple MW reads for each voxel for input into the super-resolution algorithm. More specifically, the super-resolution algorithm converts each 2D matrix 555-565 into an output grid, as shown in FIGS. 18A-18B, which are then combined to form a final super-resolution output voxel grid, as shown in 18B. This final super-resolution output voxel grid corresponds to the MIBA file output voxel grid in the MIBA file 3D volume and for coded entry into the MIBA spreadsheet format.

Referring specifically to FIG. 18A, a read count kernel 530 may be used to determine the number of moving window reads within each voxel of the defined final super-resolution output voxel grid which matches the MIBA FILE output voxel grid. A defined threshold is set to determine which voxels receive a reading as a voxel fully enclosed within the moving window, or at a set threshold, such as 98% enclosed. Each of these voxels within the read count kernel 530 has a value of 1 within the read count kernel. The read count kernel 530 moves across the output grid at step size matching the size of the super resolution voxels and otherwise matches the shape, size, and movement of the corresponding specified moving window defined during creation the 3D matrices. Moving window readings are mapped to voxels that are fully contained within the moving window, such as the four voxels labeled with reference numeral 535. Alternatively, moving window read voxel may be defined as those having a certain percentage enclosed in the moving window, such as 98%.

Further, values from moving window reads (e.g., A+/−sd, B+/−sd, C+/−sd) are mapped to the location on the final super-resolution output voxel grid which matches the MIBA FILE output voxel grid and the corresponding values is assigned to each full voxel contained within the moving window (or partially contained at a desired threshold, such as 98% contained). For example, the post-MLCA 2D matrix contains the moving window reads for each moving window, corresponding to the values in the first three columns of the first row. Each of the 9 full final super-resolution output voxel grid which matches the MIBA FILE output voxels within the first moving window (MW 1) receives a value of A+/−sd, each of the 9 full output SR voxels within the second moving window (MW 2) receives a value of B+/−sd, and each of the 9 full output SR voxels within the third moving window (MW 3) receives a value of C+/−sd.

Figure 18C:
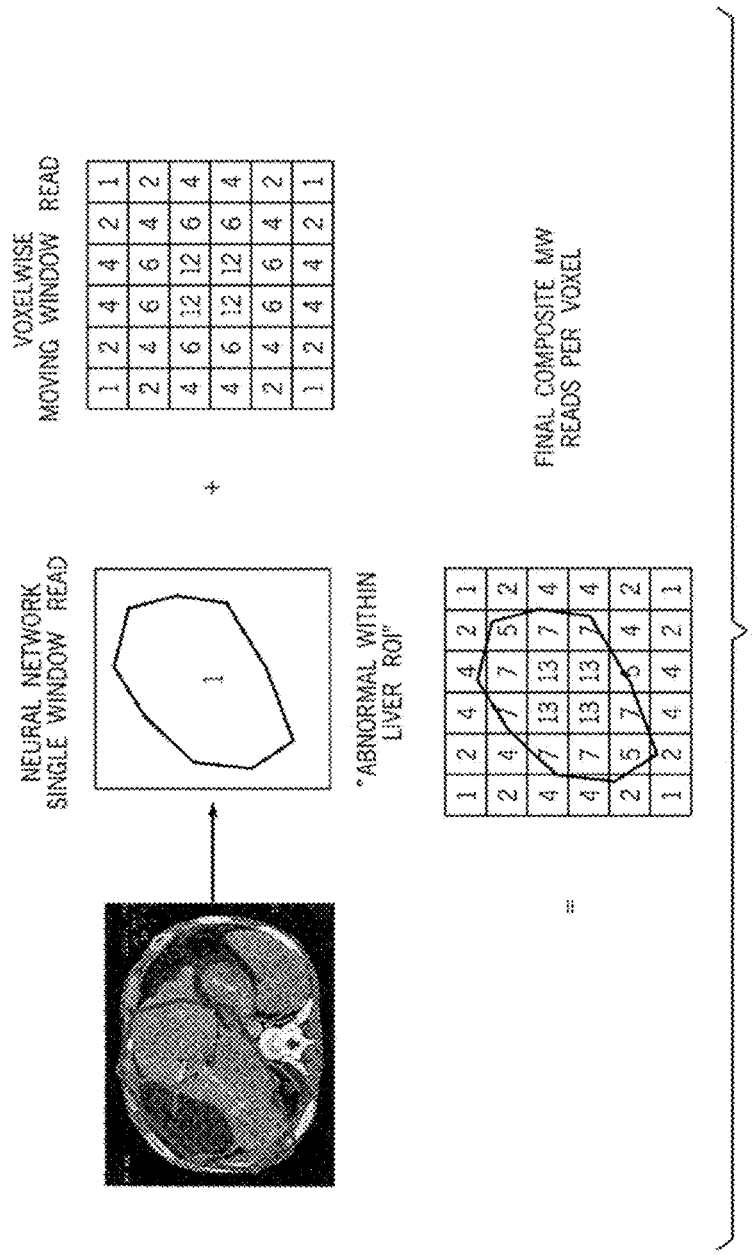
FIG. 18C is another example of obtaining the 2D final voxel grid, in accordance with some embodiments of the present disclosure.

FIG. 18C depicts another embodiment of obtaining an output MIBA FILE output voxels grid. Specifically, neural network methods may be deployed such that full image or full organ neural network read may return a single moving window read per entire image or organ region of interest. Such a read may represent a probability that a tissue is normal or abnormal as binary "0" or "1" or a probability, or the odds of a specific diagnosis, depending on type of input labelled data inputted into the neural networks. Moving window reads may be added as for other reads, discussed above, and only voxels contained with organ ROI may be added with this notation into the MIBA file.

Alternately, standard classifier methods, such as vector machines, can be used to solve for a probability of a given biomarker with a segmented region, such as a tumor. Similarly, all voxels values for voxels meeting volume criteria (for example, 98% inclusion within output voxel) are entered into the MIBA file.

Examples of simplified existing clinical imaging tumor biomarkers that are based on standard whole tumor ROI and standard classifiers include, but are not limited to, multi-parameter MRI for detection of prostate tumors using the PI-RADS system (using scoring with T2, DWI, and DCE-MRI sequences), liver tumor detection with LI-RADS system (using scoring with T1 post contrast, T2, and DWI sequences), and PET uptake changes after GIST treatment with Gleevac. Additional parameters may include, but are not limited to, DCE-MRI, ADC, DWI, T1, T2, and tau parameters. Additional example parameters are included in the charts depicted in FIG. 30A-K. The possible parameters may be obtained from different modalities including, but not limited to, MRI, PET, SPECT, CT, fluoroscopy, ultrasound imaging, BLO imaging, micro-PET, nano-MRI, micro-SPECT, and Raman imaging. Accordingly, the matching parameters may include any of the types of MRI parameters depicted in FIGS. 30A-K, one or more types of PET parameters depicted, one or more types of heterogeneity features depicted, and other parameters depicted in FIGS. 30A-K. In the simplest embodiment of the convolution algorithm, the biomarker may be defined as a set of defined thresholds for various image data or parameters (for example, T1>500, T2<2000, and DWI>2000) and the algorithm would return a simple "yes" or "no" solution of the MW data fits the defined biomarker thresholds. This most simplified version of the convolution algorithm (MLCA) would be most similar to established clinical biomarkers that define probabilities of cancer, such as Li-RADS. New and more complex imaging biomarkers may be discovered in the future and could be similarly applied to the described method. In a specific embodiment, a set of biomarkers provides a reliable prediction of whether a given voxel contains normal or abnormal anatomy.

Thus, as shown in FIG. 18B, a first 2D matrix 555 is converted into a first MIBA file intermediate voxel grid 560 and a second 2D matrix 565 is converted into a second output intermediate voxel grid 570. The output intermediate voxel grid 560 and the output intermediate voxel grid 570 are then combined according to a super-resolution algorithm (e.g., addition algorithm) to obtain a final super-resolution output grid matching the final MIBA file voxel output grid 575. FIGS. 18A-18B provide examples where the output intermediate voxel grids and the final MIBA file voxel grid are both represented as 2D matrices. In some embodiments, the final super-resolution output grid matching the final MIBA file voxel grid may be a represented as a 3D matrix.

Returning back to FIGS. 4A and 4B, upon generating a final MIBA file voxel grid at the operation 246, it is determined whether any additional biomarkers remain to be analyzed for the given set of 3D matrices. If there are additional biomarkers or features or areas of interest to be analyzed for the given set of 3D matrices, the operations 220-246 are repeated for each additional biomarker. In the case of each newly selected biomarker, a new MLCA is selected based on the specific training population database data for the new biomarker in the volume-code population database. In embodiments where multiple biomarkers are identified in a single voxel, the separate biomarkers may be entered as separate values in the specific designated region, such as a column, for a given voxel (collated voxel data contained in a given row) in the MIBA spreadsheet file.

FIG. 18C shows that a moving window ("MW") may equal a single segmentation, such as a segmentation of the liver (LIV_SEG). All voxels with the LIV_SEG are labelled as "liver." This single segmentation of the liver can be created by a human user or by automated techniques, such as using data-driven neural networks.

Figure 19:
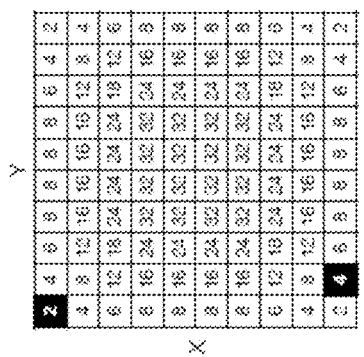
FIG. 19 shows an updated MIBA database including data from the 2D final voxel grid, in accordance with some embodiments of the present disclosure.

FIG. 19 depicts the mapping of convoluted graph data back to the MIBA file output voxel grid. Data cells in the post-MLCA 2D matrix are mapped to the MIBA file output voxel grid such that any voxel fully or almost fully (for a defined percentage; for example, greater than 90%) within the borders of the original MW is mapped as a MW reads for the corresponding pt3Dvol voxel MIBA file output voxel grid. In this example, the top edge voxels for each convoluted graph have one MW read each, while the center top row voxels have four MW reads each. When two mapping grids are combined, the resulting grid has two MW reads at top edges, and eight MW reads at the central top row. FIG. 19 shows entry of the final mapped grid MW data into the MIBA database in corresponding labelled rows.

Figure 20:
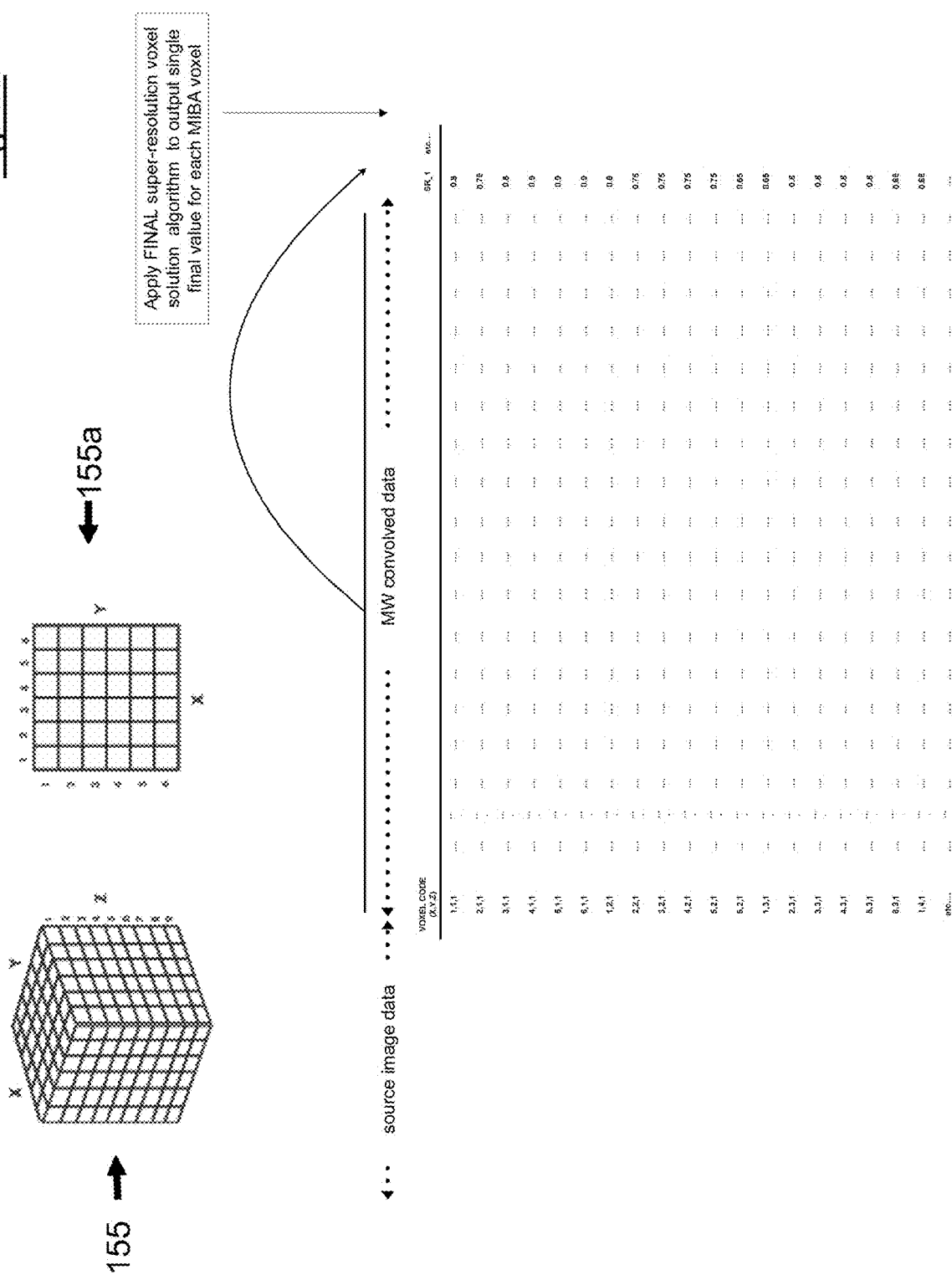
FIG. 20 shows an example of the MIBA master file including MIBA voxel data, in accordance with some embodiments of the present disclosure.

FIG. 20 describes entry of FINAL super-resolution voxel solutions from the collated multiple MW reads for each designated voxel with MIBA file output grid. A set of MW reads is selected, for example, eight MW reads in row 4,1,1 are selected. A FINAL super-resolution voxel solution algorithm is selected and applied to obtain FINAL output MIBA file voxel values. In general, the FINAL super-resolution voxel solution takes the multiple input MW reads which may be discrete values, probabilities, and binary solutions (yes or no) and outputs a solution aimed at finding the "true" solution. In the simplest embodiment, the FINAL voxel super-resolution solution algorithm could be a simple calculation, such as the simple average of all MW reads. If the input MW reads are binary answers (such as yes and no), the super-resolution algorithm could return the most common solution (e.g. yes MW reads>no MW reads.) The specific super-resolution voxel solution algorithm alternately be chosen from various types which could include general families of frequency domain (wavelet and fourier) and probabilistic (maximum likelihood and Maximum a priori (MAP) algorithms which include markov random fields, total variation, and bimodality priori, as well as single image techniques such as neural network techniques, principal component analysis, and tensor techniques, as well as others.

After the FINAL voxel solution algorithm is chosen and applied, in FIG. 20, output final super-resolution MIBA file voxel values are entered at corresponding locations within the MIBA file spreadsheet format.

Figure 21:
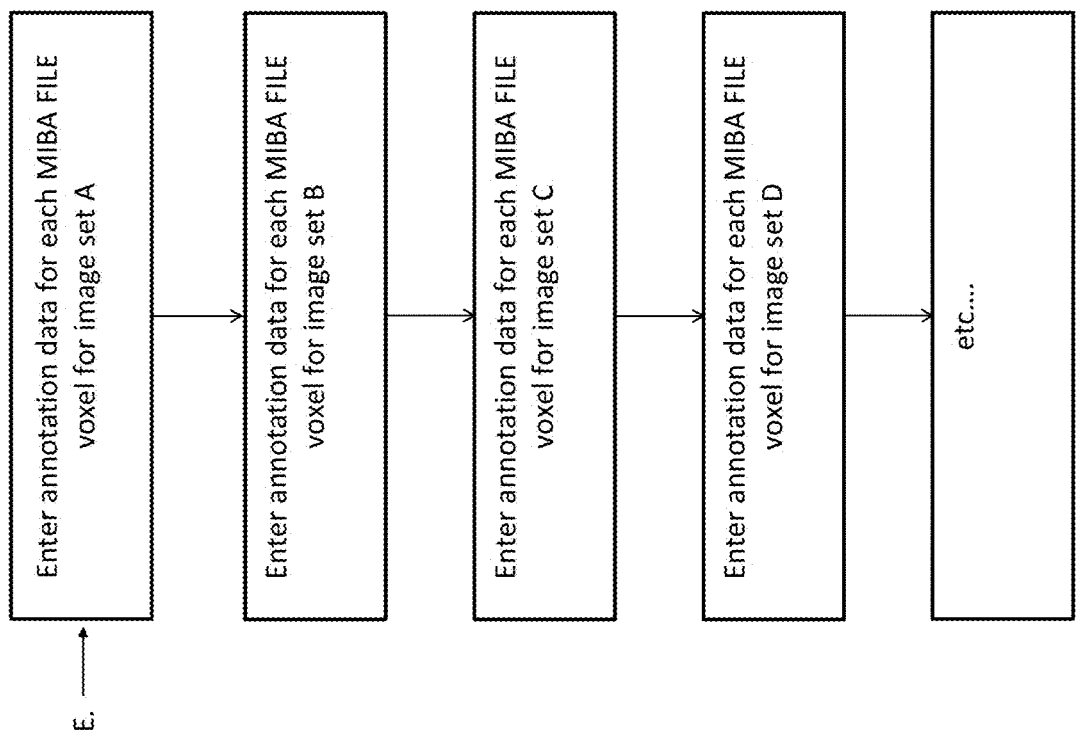
FIG. 21 is an example flowchart outlining operations for entering annotation data in the MIBA master file, in in accordance with some embodiments of the present disclosure.

FIG. 21 describes the last type of data for entry into the MIBA database, namely annotation data. Annotation data can take many forms, and is simply not primary medical imaging data. For example, it can include physician notations, genetics data corresponding to a biopsy segmentation, anatomically mapped data from digital health record. Annotation data imprinted from a user, such as a physician, is collected from all images in the original dataset or the image sets 211 (see FIG. 7) generated from the image processor and output display unit. Annotation data from annotations added directly to images by people, such as Radiologists and other physicians, is entered into the MIBA database as metadata within a single cell, or entered in each corresponding voxel location.

FIG. 22 shows that the annotations from FIG. 21 are entered into the MIBA file database. Annotation can be hand-drawn regions-of-interest (hd-ROI) or computer generated segmentations on any image type or parameter map and notations are made in the MIBA database to indicate whether a given voxel is contained within the ROI. Alternately, metadata such as a DICOM header for an original image may be embedded in a single corresponding cell in the MIBA database. Metadata entry could also include lines in reports for specific ROI of lesions, as well as follow-up recommendations or differential diagnoses by the Radiologist. Annotations can also mark the data for potential upload to the volume-coded population database. Additionally, annotations may include biopsy data obtained from the selected image datasets 210 and may be labelled as biopsy for all voxels contained in the segmentation of the biopsy sample. In some embodiments, any pathology or genetics related information gleaned from the biopsy data may also be added to the MIBA master file as an annotation. In other embodiments, other relevant notes may be added to the MIBA master file as annotations.

FIG. 23 describes an overview of how successive imaging data collected at later time points would be incorporated into a prior MIBA file 150 and updated into a new MIBA file 155 using the process outlined in FIG. 4A-B. A matching process would be followed as previously described, but specifically using the prior MIBA file 150 instead of the reference 3D volume (ref3D) using rigid of affine registration. Any possible image data contained in both the prior MIBA and new dataset 211 could be used for registration, including data showing "yes" voxel data for normal anatomy, allowing great potential power in registering a new MIBA file to a prior MIBA file. Additional of multiple time points would also allow for assessing changes in MW reads across time points. Data would be compressed as a last step to deleted or otherwise compress unneeded data, such as redundant normal tissue data. Further, registration data may be saved such that original source DICOM images may be recovered from post-registration data.

FIG. 23 describes how successive MIBA files are created across time points. Data compression allows decrease of memory demands, such as deletion of redundant normal anatomy imaging data. FIG. 24 shows a schematic of a final MIBA spreadsheet file at time point 5. Similar MIBA database files may exist for other time points shown in FIG. 23.

Figure 25:
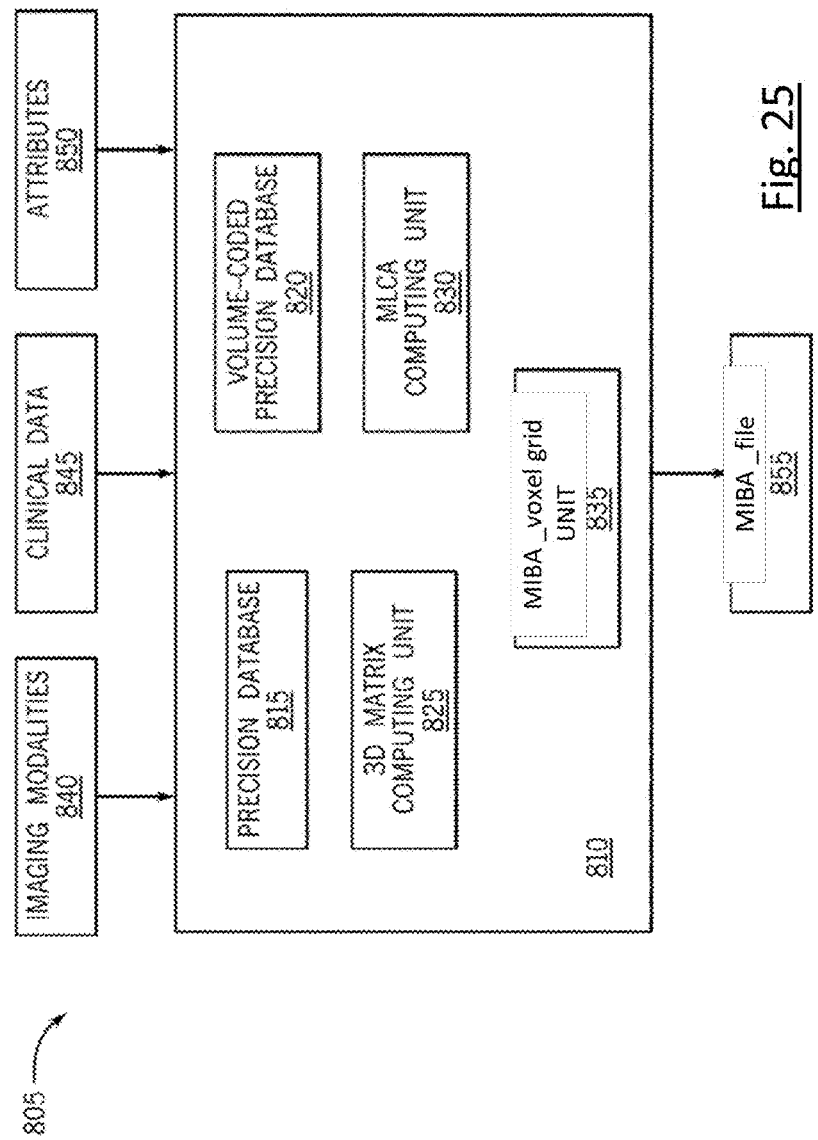
FIG. 25 is an example block diagram of a MIBA creation unit of a MIBA system, in accordance with some embodiments of the present disclosure.

FIG. 25 shows an example block diagram of a portion of a MIBA system 805 that may be used to create a MIBA master file, as discussed above. The MIBA system 805 may be used for generating the MIBA master file, as discussed above. The MIBA system 805 includes a MIBA creation unit 810 having a precision database 815, a volume-coded precision database 820, a 3D matrix computing unit 825, an MLCA computing unit 830, and a MIBA voxel grid unit 835. In alternative embodiments, the specific sub-units and databases of image computing unit 810 may be separate devices or components that are communicatively coupled. The precision database 815 and the volume-coded precision database 820 are configured to store image data, as discussed above. To that end, the MIBA creation unit 810 may be connected to one more imaging modalities 840 to receive image data corresponding to those modalities. The imaging modalities 840 may also provide image data for the sample that is to be analyzed and for which the MIBA master file is to be generated. In some embodiments, instead of receiving image data directly from the imaging modalities 840, the MIBA creation unit 810 may be connected to another computing unit, which receives the image data from the imaging modalities, and provides that data to the image computing unit.

As also discussed above, the precision database 815 and the volume-coded precision database 820 stores clinical data 845 as well. The clinical data 845 may be input into the MIBA creation unit 810 by a user. In addition, various attributes 850 (e.g., parameters and parameter maps of interest, moving window parameters, various thresholds, and any other user defined settings) are also input into the MIBA creation unit 810. The MIBA creation unit 810 may also include the 3D matrix computing unit 825 that is configured to compute 3D matrices, the MLCA computing unit 830, which transforms the 3D matrices into 2D matrices, and a MIBA voxel grid unit 835 to convert the 2D matrices into the MIBA master file, as discussed above. The MIBA creation unit 810 may output a MIBA master file 855 upon creation. The MIBA master file 855 may be stored within a database associated with the MIBA system 805 and may be used by a query system (described in FIG. 29) to provide a variety of relevant information.

The MIBA creation unit 810 and the units therein may include one or more processing units configured to execute instructions. The instructions may be carried out by a special purpose computer, logic circuits, or hardware circuits. The processing units may be implemented in hardware, firmware, software, or any combination thereof. The term "execution" is, for example, the process of running an application or the carrying out of the operation called for by an instruction. The instructions may be written using one or more programming language, scripting language, assembly language, etc. The image computing unit 810 and the units therein, thus, execute an instruction, meaning that they perform the operations called for by that instruction.

The processing units may be operably coupled to the precision database 815 and the volume-coded precision database 820 to receive, send, and process information for generating the MIBA master file 855. The MIBA creation unit 810 and the units therein may retrieve a set of instructions from a memory unit and may include a permanent memory device like a read only memory (ROM) device. The MIBA creation unit 810 and the units therein copy the instructions in an executable form to a temporary memory device that is generally some form of random access memory (RAM). Further, the MIBA creation unit 810 and the units therein may include a single stand-alone processing unit, or a plurality of processing units that use the same or different processing technology.

With respect to the precision database 815 and the volume-coded precision database 820, those databases may be configured as one or more storage units having a variety of types of memory devices. For example, in some embodiments, one or both of the precision database 815 and the volume-coded precision database 820 may include, but not limited to, any type of RAM, ROM, flash memory, magnetic storage devices (e.g., hard disk, floppy disk, magnetic strips, etc.), optical disks (e.g., compact disk (CD), digital versatile disk (DVD), etc.), smart cards, solid state devices, etc. The MIBA master file 855 may be provided on an output unit, which may be any of a variety of output interfaces, such as printer, color display, a cathode-ray tube (CRT), a liquid crystal display (LCD), a plasma display, an organic light-emitting diode (OLED) display, etc. Likewise, information may be entered into the image computing unit 810 using any of a variety of unit mechanisms including, for example, keyboard, joystick, mouse, voice, etc.

Furthermore, only certain aspects and components of the MIBA system 805 are shown herein. In other embodiments, additional, fewer, or different components may be provided within the MIBA system 805. Thus, the present disclosure provides a system and method that includes identifying aggregates of features using classifiers to identify biomarkers within tissues, including cancer tissues, using a precision database having volume-coded imaging-to-tissue data. The method involves the application of a super-resolution algorithm specially adapted for use in medical images, and specifically magnetic resonance imaging (MRI), which minimizes the impact of partial volume errors. The method determines probability values for each relevant super-resolution voxel for each desired biomarker, as well as each desired parameter measure or original signal. In this way, innumerable points of output metadata (up to 10, 1000, 10000 data points) can be collated for each individual voxel within the MIBA master file.

Figure 26:
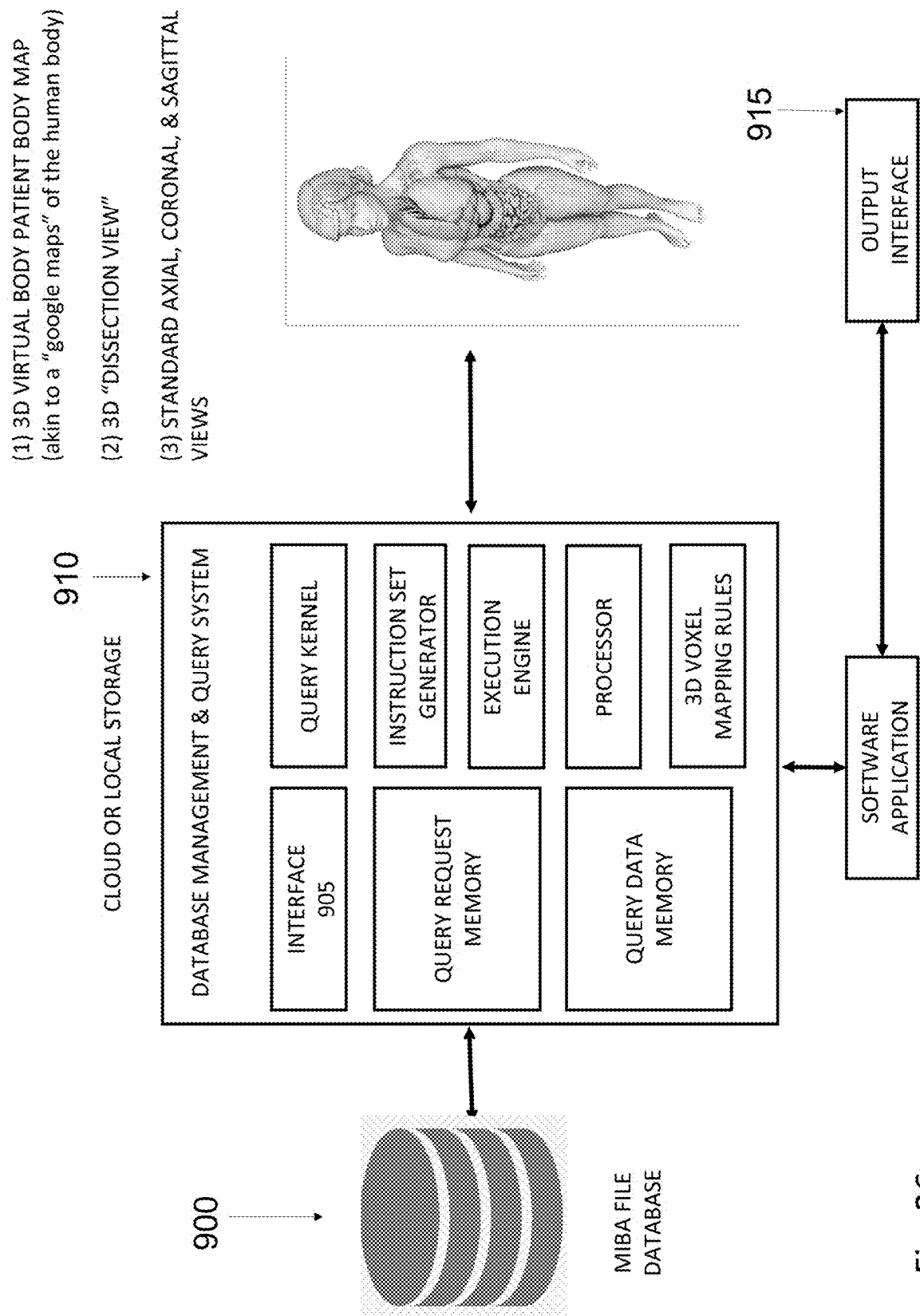
FIG. 26 is an example block diagram of a MIBA query system of the MIBA system, in accordance with some embodiments of the present disclosure.

FIG. 26 is another block diagram of a portion of the MIBA system depicting use of the MIBA master file upon creation. The MIBA master file from MIBA database 900 is entered into an input interface 905 of a MIBA query system 910. The MIBA query system 910 collects inputs from a user which is processed by an image processor which outputs the results as an image or image/data display on an output interface 915. For example, a sample query to the query system 910 may ask to return all rows from the MIBA master File where MIBA voxels show high probability of vessel. The database management and query system includes an interface for a user or computer software program, query request memory, memory for holding results of a query, a query kernel, an instruction set generator, an execution engine, a processor, and 3D voxel mapping rules. A software application, with its own user interface, can be used to act on these various components. It is to be understood that the MIBA system 26 is intended to include various components similar to the MIBA system 805, including, for example, processors, memory systems, interfaces, etc. An output interface 915 is used to display the MIBA file in 3D which can be (1) via mapping of query data to specific anatomical locations in a virtual display of the patient body (akin to a "google maps" of the human body), (2) a 3D dissection view where the user can define view of the actual MIBA output voxel grids and the contained metadata within the MIBA voxels, such as viewing all vessel data, all T1 images, or all voxels showing a specific biomarker, and (3) standard images can be outputted matching standard DICOM images in axial, coronal, and sagittal planes.

It is also to be understood that only some components of the MIBA system 805 have been shown and described in FIGS. 25 and 26. Nevertheless, other components that are desired or considered necessary to perform the functions described herein are contemplated and considered within the scope of the present disclosure.

Figure 27:
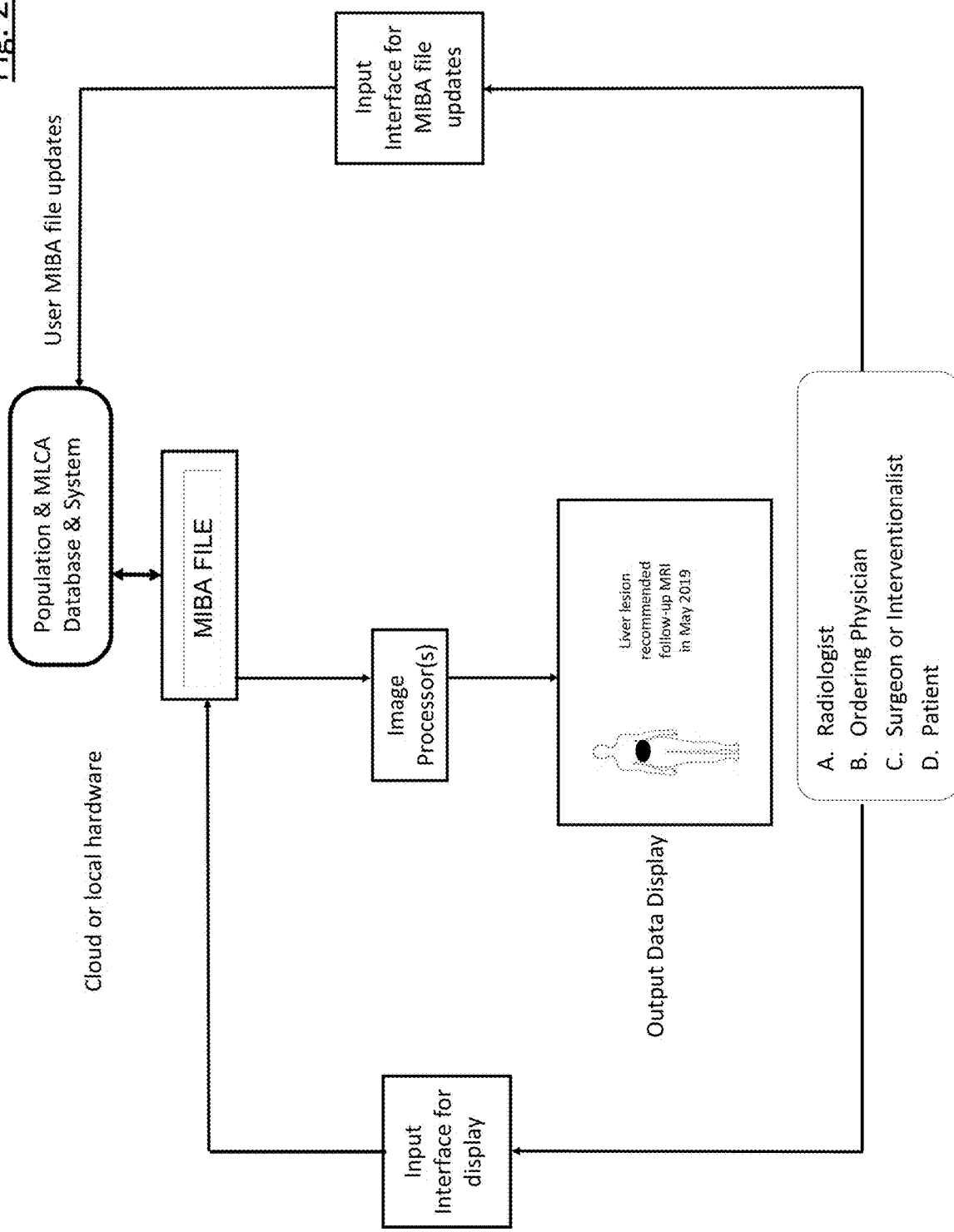
FIG. 27 illustrates creating and using the MIBA master file, in accordance with some embodiments of the present disclosure.

FIG. 27 describes an example of an application for using the MIBA master file system for querying the MIBA file to identify datasets, such as all voxels labelled as "liver tumor" and for user annotation. An image processor allows a user to select a display of a patient's liver lesion for which a doctor or other person can add an annotation that is entered back into the MIBA file for the specific region-of-interest. The MIBA file can be stored and executed from cloud or local storage. Data can also be uploaded to a population database. The image display unit could specific colors for image voxel display characteristics. Images could be displayed on apps for smartphones, iPads, and iPhones, etc. MIBA could also be used for input data during scanning or during an intervention.

Figure 28:
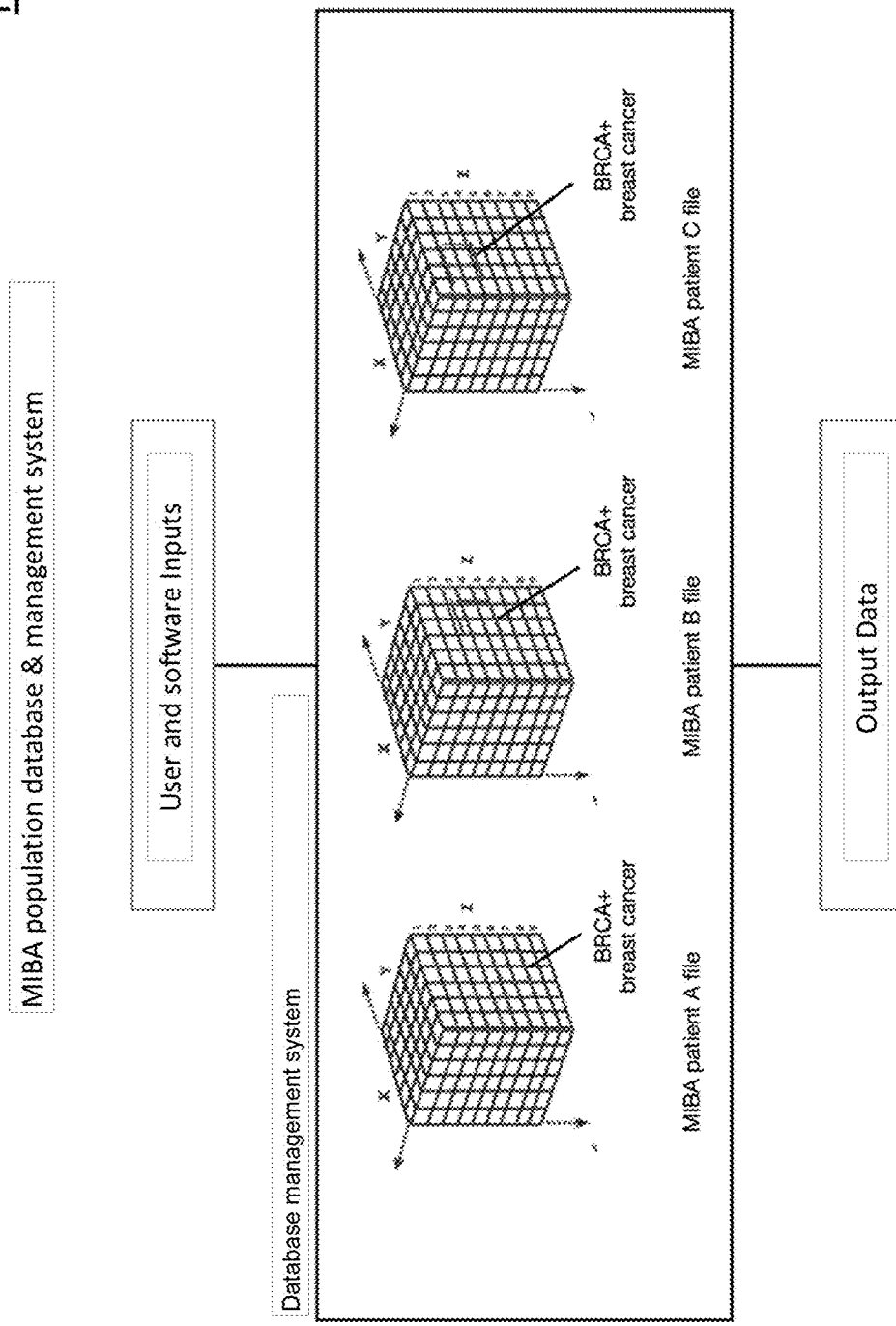
FIG. 28 shows an example of using a population database along with the MIBA master file, in accordance with some embodiments of the present disclosure.

FIG. 28 describes how multiple MIBA files could be storage in a single system, such as the cloud or blockchain, and users can query for data across multiple patients, such as all biopsy imaging data for all breast cancer patients that showed BRCA+ genetics. As described, multiple MIBA files are held in the database management system and a user can enter a query to allow selection of specific data, for example, all imaging and related data contained within region-of-interest for BRCA+ breast cancer lesions. The collated data could be outputted for future use.

Provided in the above description is a means to label anatomy within the MIBA file. As such, this process can be repeated in any fashion to fit to a given desired anatomical topological mapping of the human body. For example, in FIG. 29A, the skin surfaces of the human body are mapped and correspond to topological human body segments that can be matched across a population of human bodies. In FIGS. 29B-C, this topological mapping can be applied to human heads, and various configurations can be used to describe tissue around the eyes. In FIG. 29C, such mapping can also align with defined anatomy, such as the various Couinaud segments of a liver. In FIG. 29E, the smoothness of the anatomical segment edges are a function of the underlying resolution of the MIBA file voxel output voxel grid. A finer MIBA file voxel grid will create a more smooth output anatomical segment edge. As depicted in FIG. 29A-D, topological maps require that the edges between segments are fully aligned with no spaces in between anatomical segments.

It is to be understood that although the present disclosure has been discussed with respect to cancer imaging, the present disclosure may be applied for obtaining imaging for other diseases as well. Likewise, the present disclosure may be applicable to non-medical applications, particularly where detailed super-resolution imagery is needed or desired to be obtained.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (for example—"a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method comprising:
receiving, by a medical imaging bioinformatics annotated ("MIBA") system, image data from a sample;
registering, by the MIBA system, the image data to a three-dimensional (3D) model selected from a population database for obtaining source data;
receiving selection, by the MIBA system, of a volume of interest;
extracting, by the MIBA system, a portion of the source data corresponding to the volume of interest;
defining, by the MIBA system, a moving window;
applying, by the MIBA system, the moving window to the portion of the source data for obtaining a dataset;
applying, by the MIBA system, a convolution algorithm to the dataset for obtaining convoluted data;
creating, by the MIBA system, a MIBA master file from the convoluted data; and
determining, by the MIBA system, a probability of a biomarker from the MIBA master file.

2. The method of claim 1, wherein the sample is a body tissue of a patient, and wherein the 3D model is of another patient sharing at least one attribute with the patient.

3. The method of claim 1, wherein the image data comprises images from a plurality of image modalities.

4. The method of claim 3, further comprising:
combining, by the MIBA system, the images from the plurality of image modalities based on an in-slice registration for obtaining in-slice registered data.

5. The method of claim 4, further comprising:
mapping, by the MIBA system, the in-slice registered data to the 3D model for obtaining the source data;
extracting, by the MIBA system, voxel data from the source data; and
entering, by the MIBA system, the voxel data into a MIBA database.

6. The method of claim 1, further comprising receiving parameters for defining the moving window, wherein the parameters include at least one of a size, a shape, a type of output value, a step size, and a direction of movement for the moving window.

7. The method of claim 1, wherein applying the moving window further comprises:
creating, by the MIBA system, a 3D matrix from the portion of the source data;
refining, by the MIBA system, the 3D matrix;

applying, by the MIBA system, one or more matrix operations to the refined 3D matrix; and receiving, by the MIBA system, selection of a matrix column from the 3D matrix for forming the dataset.

8. The method of claim 7, wherein refining the 3D matrix comprises at least one of dimensionality reduction, aggregation, and subset selection processes.

9. The method of claim 7, wherein the one or more operations comprises at least one of matrix addition, matrix subtraction, matrix multiplication, matrix division, matrix exponentiation, and matrix transposition.

10. The method of claim 1, wherein the convolution algorithm comprises a Bayesian belief network algorithm.

11. The method of claim 1, further comprising:
mapping, by the MIBA system, the convoluted data to the 3D model;
extracting, by the MIBA system, MIBA voxels from the mapping; and
creating, by the MIBA system, the MIBA master file with the MIBA voxels.

12. The method of claim 1, further comprising:
receiving, by the MIBA system, annotation data; and
updating, by the MIBA system, the MIBA master file to include the annotation data.

13. A medical imaging bioinformatics annotated ("MIBA") system, comprising:
a database configured to store a MIBA master file; and
a MIBA creation unit configured to:
receive image data from a sample;
register the image data to a three-dimensional (3D) model selected from a population database for obtaining source data;
extract voxel data from the source data and enter the voxel data into the database;
receive selection of a volume of interest;
extract a portion of the voxel data from the database corresponding to the volume of interest;
create the MIBA master file from the portion of the voxel data, wherein to create the MIBA master file the MIBA creation unit is further configured to:
create a 3D matrix from the portion of the voxel data;
refine the 3D matrix;
apply one or more matrix operations to the refined 3D matrix;
receive selection of a matrix column from the 3D matrix for forming the dataset:
apply a convolution algorithm to the selected matrix column to obtain convoluted data;
map the convoluted data to the 3D model;
extract MIBA voxel data from the mapped convoluted data; and
create the MIBA master file with the MIBA voxel data; and
store the MIBA master file in the database; and a MIBA query system configured to:
receive the MIBA master file from the database;
extract data from the MIBA master file in response to the query; and
present the extracted data on an output interface.

14. The MIBA system of claim 13, wherein the MIBA creation unit is further configured to:
receive annotation data; and
update the MIBA master file to incorporate the annotation data.

15. The MIBA system of claim 13, wherein the MIBA creation unit is further configured to:
receive parameters to define a moving window; and
apply the moving window to the portion of the voxel data for creating the 3D matrix.

16. The MIBA system of claim 13, wherein the image data comprises images obtained from a plurality of imaging modalities.

17. A method comprising:
creating, by a medical imaging bioinformatics annotated ("MIBA") system, a MIBA master file, wherein creating the MIBA master File comprises:
receiving, by the MIBA system, image data from a sample;
performing, by the MIBA system, a first registration on the image data for obtaining in-slice registered data;
performing, by the MIBA system, a second registration comprising registering the in-slice registered data to a three-dimensional (3D) model selected from a population database for obtaining source data;
extracting, by the MIBA system, voxel data from the source data and storing the voxel data in a MIBA database;
receiving, by the MIBA system, selection of a volume of interest;
extracting, by the MIBA system, a portion of the voxel data corresponding to the volume of interest;
creating, by the MIBA system, the MIBA master file from the portion of the voxel data, wherein creating the MIBA master file comprises:
applying, by the MIBA system, a moving window to the portion of the voxel data;
applying, by the MIBA system, a convoluted algorithm to an output of the moving window for obtaining convoluted data; and
mapping, by the MIBA system, the convoluted data to the 3D model for creating the MIBA master file; and
storing, by the MIBA system, the MIBA master file in the MIBA database; and
receiving, by the MIBA system, a query;
extracting, by the MIBA system, data from the MIBA master file in response to the query; and
presenting, by the MIBA system, the extracted data on an output interface.

18. The method of claim 17, further comprising:
receiving, by the MIBA system, annotated data; and
updating, by the MIBA system, the MIBA master file with the annotated data.

* * * * *